(12) United States Patent
Eger et al.

(10) Patent No.: US 8,415,268 B2
(45) Date of Patent: Apr. 9, 2013

(54) PROCESS FOR PRODUCING A RINGLIKE OXIDIC SHAPED BODY

(75) Inventors: Knut Eger, Limburgerhof (DE); Jens Uwe Faust, Speyer (DE); Holger Borchert, Offstein (DE); Ralf Streibert, Hochdorf-Assenheim (DE); Klaus Joachim Mueller-Engel, Stutensee (DE); Andreas Raichle, Dresden (DE)

(73) Assignee: BASF SE, Ludwigshafen (DE)

( * ) Notice: Subject to any disclaimer, the term of this patent is extended or adjusted under 35 U.S.C. 154(b) by 687 days.

(21) Appl. No.: 12/494,991

(22) Filed: Jun. 30, 2009

(65) Prior Publication Data

US 2010/0010238 A1 Jan. 14, 2010

Related U.S. Application Data

(60) Provisional application No. 61/077,638, filed on Jul. 2, 2008, provisional application No. 61/077,601, filed on Jul. 2, 2008.

(30) Foreign Application Priority Data

Jul. 2, 2008 (DE) .......... 10 2008 040 093
Jul. 2, 2008 (DE) .......... 10 2008 040 094

(51) Int. Cl.
*B01J 21/04* (2006.01)
*B01J 23/00* (2006.01)
*B01J 23/02* (2006.01)
*B01J 23/10* (2006.01)
*B01J 23/40* (2006.01)
*B01J 23/42* (2006.01)
*B01J 23/58* (2006.01)
*B01J 23/70* (2006.01)
*B01J 23/72* (2006.01)
*B01J 27/00* (2006.01)
*B01J 27/198* (2006.01)
*B01J 27/188* (2006.01)
*B01J 27/19* (2006.01)
*B01J 27/192* (2006.01)
*B01J 27/185* (2006.01)
*B01J 27/182* (2006.01)
*B28B 1/00* (2006.01)
*B28B 3/00* (2006.01)
*B28B 5/00* (2006.01)
*B28B 11/00* (2006.01)
*B28B 21/00* (2006.01)
*B28B 21/72* (2006.01)
*B28B 23/08* (2006.01)
*C04B 33/32* (2006.01)
*C04B 33/36* (2006.01)
*C04B 35/64* (2006.01)
*B29D 22/00* (2006.01)
*B29D 23/00* (2006.01)
*B31B 1/08* (2006.01)
*B31B 45/00* (2006.01)
*A47G 19/22* (2006.01)
*B32B 1/08* (2006.01)
*F16L 9/10* (2006.01)

(52) U.S. Cl. ........ 502/300; 502/304; 502/305; 502/308; 502/311; 502/312; 502/314; 502/315; 502/316; 502/317; 502/318; 502/319; 502/321; 502/326; 502/330; 502/331; 502/345; 502/208; 502/209; 502/210; 502/211; 502/212; 502/213; 502/214; 502/439; 264/603; 264/632; 264/671; 264/673; 264/681; 428/34.1; 428/34.4

(58) Field of Classification Search .................. 502/300, 502/439, 208–214, 304, 305, 314–319, 311, 502/312, 321, 326, 330, 331, 345; 264/603, 264/632, 671, 673, 681; 428/34.1, 34.4
See application file for complete search history.

(56) References Cited

U.S. PATENT DOCUMENTS

| | | | | |
|---|---|---|---|---|
| 2,077,519 | A | * | 4/1937 | Frayer .............................. 470/25 |
| 5,885,925 | A | * | 3/1999 | DeFilippi et al. ............. 502/427 |
| 8,119,554 | B2 | * | 2/2012 | Kashani-Shirazi et al. .. 502/159 |

OTHER PUBLICATIONS

U.S. Appl. No. 12/557,021, filed Sep. 10, 2009, Raichle, et al.

*Primary Examiner* — Patricia L Hailey
(74) *Attorney, Agent, or Firm* — Oblon, Spivak, McClelland, Maier & Neustadt, L.L.P.

(57) ABSTRACT

A process for producing a ringlike oxidic shaped body by mechanically compacting a pulverulent aggregate introduced into the fill chamber of a die, wherein the outer face of the resulting compact corresponds to that of a frustocone.

67 Claims, 10 Drawing Sheets

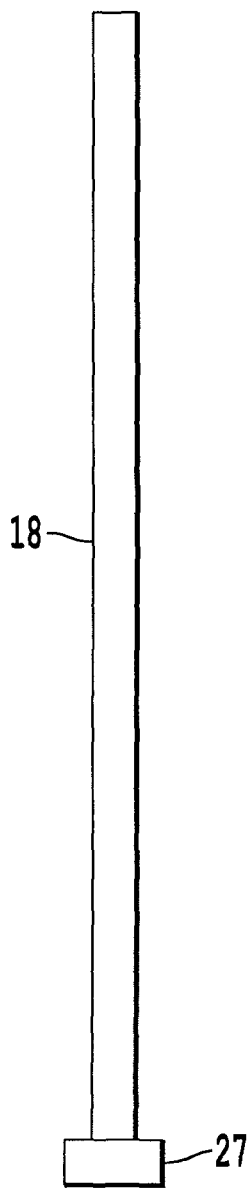 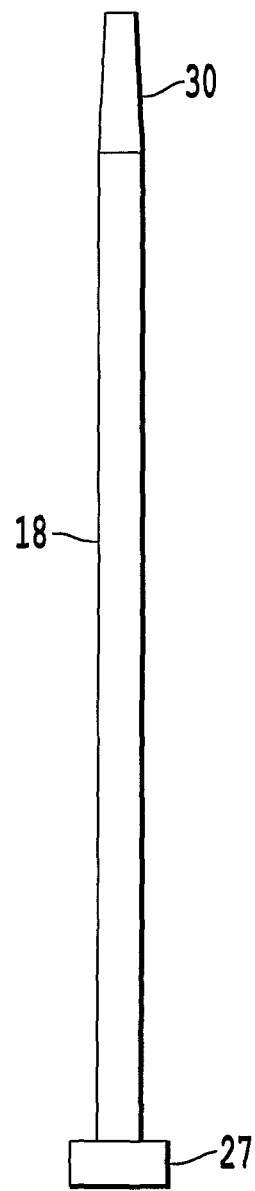
*Fig. 7*  *Fig. 8*

PROCESS FOR PRODUCING A RINGLIKE OXIDIC SHAPED BODY

BRIEF DESCRIPTION OF THE DRAWINGS

FIG. 7 shows a longitudinal section through a center pin which has, from the bottom upward, exclusively the geometric shape of a circular cylinder.

FIG. 8 shows a longitudinal section through a center pin which, from the bottom upward, first has the geometry of a circular cylinder and then narrows conically up to its upper end.

FIG. 1 and FIG. 6 center pin may be adjoined by a widened cross section which eases the fixing of the center pin.

FIGS. 2a and 2b longitudinal section through dies.

FIGS. 3a and 3b longitudinal section through dies with congruent double frustocone.

FIGS. 4a, 4b, 4c and 4d show longitudinal section through appropriate upper puncher provided with at least one outlet.

FIG. 5a longitudinal section through a lower punch.

FIG. 5b longitudinal section through a lower punch in which the center bore is configured with constant cylindrical cross section over the entire length of the lower punch.

FIGS. 5c, 5d, and 5e three lower inlay punches in which the upper end of the lower punch is not planar.

FIG. 6 longitudinal section through the die table.

FIG. 7 longitudinal section through the center pin MF.

FIG. 8 longitudinal section through a center.

Figure 1:
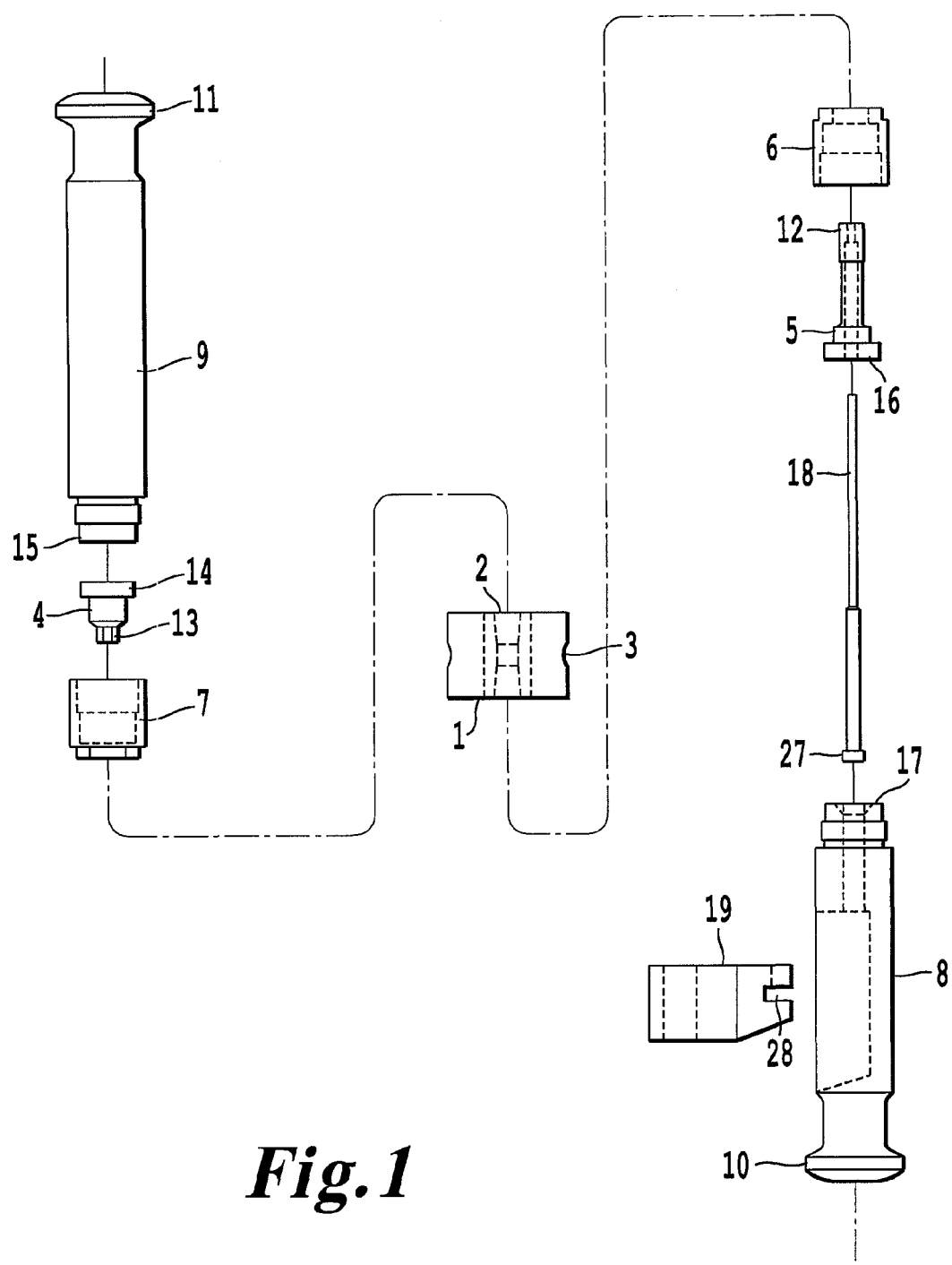
FIG. 1 shows the configuration of a mold in a kind of explosion diagram.

The present invention relates to a process for producing a ringlike oxidic shaped body comprising the mechanical compaction of a pulverulent aggregate which has been introduced into the fill chamber of a die and is composed of constituents which comprise at least one metal compound which can be converted to a metal oxide by thermal treatment at a temperature of $\geq 100°$ C., or at least one metal oxide, or at least one metal oxide and at least one such metal compound, to give a ringlike shaped precursor body, in which the fill chamber is disposed in a die bore conducted through the die material from the top downward with a vertical bore axis B and is delimited by the inner wall of the die bore, the upper end face of a lower punch introduced from below along the bore axis B into the die bore so as to be liftable and lowerable, on which the pulverulent aggregate introduced into the fill chamber rests, the louver end face, disposed along the bore axis B at an axial starting distance A above the upper end face of the lower punch, of an upper punch mounted so as to be liftable and lowerable along the bore axis B, whose lower end face is in contact with the pulverulent aggregate introduced into the fill chamber from above, and the outer face of a center pin MF conducted from the bottom upward in the die bore along the bore axis B from the geometric center of the upper end face of the lower punch, said center pin MF extending at least up to the geometric center of the lower end face of the upper punch, by reducing the axial starting distance A of the two end faces along the bore axis B to an axial end distance E predefined for the compaction by lowering the upper punch while maintaining the position of the lower punch or additionally lifting the lower punch, where the geometric shape of the outer face of the lower punch corresponds to that of the outer face of a circular cylinder I;

the geometric shape of the outer face of the upper punch corresponds to that of the outer face of a circular cylinder II;

in the geometric center of the upper end face of the lower punch, a center bore $MB^U$ conducted through the lower punch from the top downward is formed;

at the starting distance A of the two end faces, the center pin MF projects from below through the center bore $MB^U$ at least up to the geometric center of the lower end face of the upper punch;

the center pin MF, from the bottom upward, has the geometric shape of a circular cylinder Z with a circular cylindrical outer face MZ;

the length of the outline of the circular cylinder Z is less than the length of the outline of the circular cylinder I and less than the length of the outline of the circular cylinder II;

the position of the center pin MF and the position of the die including the die bore along the bore axis B are fixed relative to one another during the process;

in the geometric center of the lower end face of the upper punch, a center bore $MB^O$ which is conducted into the upper punch and is connected to at least one outlet from the upper punch (gas-permeable) is formed, said center bore $MB^O$ being capable of accommodating the center pin MF to the necessary degree in the event of reduction of the starting distance A to the end distance E, and the center pin MF being able to project into it even at the starting distance A;

the axes of symmetry of the die bore, of the circular cylinder I, of the circular cylinder II, of the center bore $MB^O$, of the center pin MF and of the center bore $MB^U$ are on a common straight line L running vertically through the die bore;

the die bore, along its bore axis, has a longitudinal section I over whose length I the geometric shape of the inner wall of the die bore corresponds to that of the outer face of a circular cylinder KZ, and which is adjoined at its upper end directly by a longitudinal section II of the die bore which is directed upward and has the length II;

the dimensions of the longitudinal section I of the die bore and of the circular cylinder I are such that the lower punch, during the process, is always conducted in each case sliding into the die bore at least for part of the length of the longitudinal section I with its outer face on the inner wall of the die bore; and the dimensions of the center bore $MB^U$ and of the circular cylinder Z are such that the lower punch, during the process, is always conducted sliding into the die bore at least in the region of the entrance of its center bore $MB^U$ into its upper end face with the inner wall of the center bore $MB^U$ on the circular cylindrical outer face MZ of the center pin MF; and on completion of compaction, the upper punch is lifted from the ringlike shaped precursor body formed and the ringlike shaped precursor body is removed from the die bore by lifting the lower punch, and a subsequent process for thermal treatment of the ringlike shaped precursor body Cit a temperature of $\geqq 100°$ C., in which at least a portion of its constituents is decomposed and/or converted chemically to form at least one gaseous compound and the ringlike oxidic shaped body forms.

In this document, the term "lower (upper) end face" of a punch means the surface of the end of the punch at its lower (upper) end. When the punch is, for example, a circular ring cylinder, both its lower end face and its upper end face are a circular ring.

In this document, the term "circular cylinder" always means a "right circular cylinder". When the end points of parallel radii of two circles of equal size lying in parallel planes are connected to one another by lines, this gives rise to a circular cylinder. The connecting lines are known as surface lines of the cylinder. When they are at right angles to the parallel circular planes, the cylinder is referred to as "right" or a rotational cylinder. The connecting line of the circle centers is the axis of symmetry of the right circular cylinder (frequently also referred to simply as "circular cylinder axis" or "axis of the circular cylinder"). The entirety of all surface lines forms the outer face of the cylinder.

In an analogous manner, the term "frustocone" in this document means another specific rotational figure. This figure (the frustocone) is formed by cutting off a smaller right cone parallel to the base surface from a right circular cone. The larger of the two parallel circular faces formed by cutting it off is also referred to in this document as the bottom face and the smaller as the top face. The separation of bottom face and top face is referred to as the height of the frustocone. The third of the faces delimiting a frustocone is referred to as the outer face thereof. The line connecting the centers of bottom face and top face forms the axis of symmetry of the frustocone (frequently also referred to simply as "axis of the frustocone"). A cone is understood to mean a figure which is determined by a circle (base circle) and a point outside the plane of the circle (tip of the cone) and arises by connecting the points on the outline of the circle with the one point outside the plane of the circle. When the line connecting the tip of the cone to the center of the base circle of the cone is at right angles to the base plane, the cone is a right circular cone or rotational cone.

In this document, the term "circular ring" means the area between two concentric circles, i.e. between two circles with a common center.

When the particular end points of parallel radii on the two outer circles and the particular end points of parallel radii on the two inner circles in two congruent circular rings lying in parallel planes (the bottom circular ring and the top circular ring) are connected by lines, this gives rise to a circular ring cylinder. The lines connecting the end points on the two inner circles are known as inner surface lines of the circular ring cylinder (their entirety forms the inner face of the circular ring cylinder) and the lines connecting the end points on the two outer circles are known as outer surface lines of the circular ring cylinder (their entirety forms the outer surface of the circular ring cylinder). When the surface lines are at right angles to the two circular rings, the circular ring cylinder is referred to as right or not irregular. In this document, the term "circular ring cylinder" should always refer to the right circular ring cylinder. The line connecting the circular ring centers is known as the axis of the circular ring cylinder.

In this document, the term "bore" shall not be understood such that the orifice in question must have been generated with the aid of drills by drilling. Instead, the orifice may also have been obtained in another way (for example with the aid of a laser, of a milling cutter or of a cutting torch). The symmetry of the orifice should, however, be such as if it had been generated by drilling with the aid of a drill (or several drills) (of course, it may actually have been generated in this way).

The outer face refers to the surface of a geometric shaped body without a base (bottom face) and lid (top face).

The feature "the outer face of a circular cylinder slides over the inner wall of a bore" (or vice versa) should be understood in this document such that, unless stated otherwise, the outer wall of the circular cylinder corresponding to the outer face, over the region of the sliding zone (i.e. over the sliding region) rests on the inner wall of the bore in a homogeneous but gas-permeable and axially mobile manner.

Processes for producing an annular (circular cylindrical) oxidic shaped body using procedures similar to the procedure detailed in the preamble of this document are known (cf., for example, EP-A 184 790, US 2005/0263926 and JP-A 10/29097).

They are typically employed in order to generate, from pulverulent mixtures (aggregates) of metal oxides and/or of those metal compounds (e.g. salts) which can be converted to metal oxides by heating (thermal treatment) (at least by thermal treatment in the presence of gaseous molecular oxygen and/or of gaseous oxygen-releasing components), circular cylindrical or, for short, "annular" shaped precursor bodies which, after subsequently performed thermal treatment (generally at temperatures of $\geqq 100°$ C.) can be used as catalysts (in which case reference is made to annular unsupported catalysts) or as shaped support bodies (also referred to for short just as "support bodies") for catalytic active compositions (for example for annular coated catalysts (comprise the catalytic active composition applied to the outer surface of the shaped support body) or for annular impregnated catalysts (the catalytically active composition is introduced (for example by impregnation) into the interior of the shaped support body)). The term "oxidic shaped body" expresses the fact that the shaped body comprises at least one metal oxide, frequently at least one multimetal oxide (it comprises, as well as oxygen, at least two different metals; semimetals such as phosphorus, antimony, arsenic and silicon shall also be included among the metals in this document).

Instead of the term "impregnated catalysts", the term "supported catalysts" is also frequently used. The catalytic active compositions in this case are frequently multimetal oxides. Annular shaped catalyst bodies are used, for example, to charge (if appropriate diluted with inert shaped bodies) the interior of the reaction tubes of a tube bundle reactor with a fixed catalyst bed. Useful inert shaped bodies for dilution also include annular support bodies. Such a fixed catalyst bed is suitable, inter alia, for performing heterogeneously catalyzed gas phase reactions (for example partial oxidations of organic compounds).

The appropriate reaction gas mixture flows through the fixed catalyst bed and, during the residence time over the catalyst surface, effects the desired reaction. In this connection, one advantage of annular shaped catalyst bodies is that the pressure drop that the reaction gas mixture undergoes as it passes through annular shaped catalyst bodies is particularly low (cf., for example, EP-A 184 790).

A disadvantage of shaped bodies obtained by mechanical compaction of a pulverulent aggregate is quite generally that the integrity of the powder grains in the resulting shaped body is essentially not accomplished by intramolecular chemical bonds but rather by residual interparticulate bonds. Although particle deformations and fracture operations in the compaction operation generally result in an increase in the total interparticulate contact area, the magnitude of the interparticulate binding forces generated by the compaction is comparatively limited.

According to intensive studies by the applicant, the above facts are especially of relevance in i:he production of annular shaped precursor bodies, since the walls of annular shaped precursor bodies, owing to the inner cavity which passes through them, are more fragile than those of corresponding solid cylindrical shaped precursor bodies. As a consequence, when practicing the processes according to the prior art cited in the preamble of this document, there is some formation of visually barely perceptible cracks in the resulting annular shaped precursor bodies. A subsequent thermal treatment of such annular shaped precursor bodies, in the course of which gases are additionally released in the annular shaped precursor body (normally, the compressed material comprises constituents (e.g. pore formers) which decompose and/or are converted thermally in the course of thermal treatment to form gaseous substances), causes crack formation which is already present generally to increase quite obviously and possibly to develop up to fracture. In some cases, crack formation present (which, as already stated, is frequently barely visible) also develops to the undesired fracture only when filled into the, for example, reaction tubes and/or in the course of performance of the catalytic gas phase reaction. In many cases, the thermal treatment of the shaped precursor bodies is also undertaken actually in the reactor (for example reaction tube) (for example by passing correspondingly heated gases through the already charged reaction tubes). Fragments present in the catalyst bed, however, result in compaction thereof and ultimately cause an increase in the pressure drop suffered as the reaction gas mixture flowing through it flows through it. In other words, fragments present in the fixed catalyst bed diminish exactly the advantage for whose achievement annular shaped catalyst bodies are normally used.

A countermeasure which can be taken to reduce the above-described symptoms consists, for example, before the introduction of oxidic annular shaped bodies, in screening off fragments formed in the course of production thereof (cf., for example, U.S. Pat. No. 7,147,011 and German application 102007028332.8). In the course of such a screening, those rings which previously exhibited merely marked crack formation generally also break up, and so fracture formation in the course of filling of the reaction tubes with the screen residue is generally only minimal.

However, a disadvantage of such a procedure is that the raw material costs for an industrial scale catalyst production are not inconsiderable, which is why the material which passes through the screen in the course of screening means a not inconsiderable material loss.

It was therefore an object of the present invention to provide an improved process for producing an annular oxidic shaped body which still has the disadvantages described to a reduced degree at worst.

Detailed studies have led to the result that the desired improvement can be achieved by modifying the geometry of the shaped precursor body such that the geometric shape of its outer surface no longer corresponds to that of a circular cylinder but rather (at least partly) to that of a frustocone. In this way, the end result is that only a ringlike oxidic shaped body is produced, but this impairs the desired pressure drop advantage insignificantly at worst. The significant reduction in fracture achieved by the inventive procedure is attributed to the fact that, owing to the altered geometric conditions in the removal of the shaped precursor body formed from the die bore by lifting the lower punch, the rollering friction between the inner wall of the die bore and the outer surface of the shaped precursor body can essentially be eliminated.

Accordingly, the present patent application provides a process for producing a ringlike oxidic shaped body comprising the mechanical compaction of a pulverulent aggregate which has been introduced into the fill chamber of a die and is composed of constituents which comprise at least one metal compound which can be converted to a metal oxide by thermal treatment at a temperature of $\geqq 100°$ C., or at least one metal oxide, or at least one metal oxide and at least one such metal compound, to give a ringlike shaped precursor body, in which the fill chamber is disposed in a die bore conducted through the die material (through the die) from the top downward with a vertical bore axis B and is delimited by the inner wall of the die bore, the upper end face of a lower punch introduced from below along the bore axis B into the die bore so as to be liftable and lowerable, on which the pulverulent aggregate introduced into the fill chamber rests, the lower end face, disposed along the bore axis B at an axial starting distance A above the upper end face of the lower punch, of an upper punch mounted so as to be liftable and lowerable along the bore axis B, whose lower end face is in contact with the pulverulent aggregate introduced into the fill chamber from above, and the outer face of a center pin MF conducted from the bottom upward in the die bore along the bore axis B from the geometric center of the upper end face of the lower punch, said center pin MF extending at least up to the geometric center of the lower end face of the upper punch, by reducing the axial starting distance A of the two end faces along the bore axis B to an axial end distance E predefined for the compaction by lowering the upper punch while maintaining the position of the lower punch or additionally lifting the lower punch, where the geometric shape of the outer face of the lower punch corresponds to that of the outer face of a circular cylinder I;

the geometric shape of the outer face of the upper punch corresponds to that of the outer face of a circular cylinder II;

in the geometric center of the upper end face of the lower punch, a center bore $MB^U$ conducted through the lower punch from the top downward is formed;

at the starting distance A of the two end faces, the center pin MF projects from below through the center bore $MB^U$ at least up to the geometric center of the lower end face of the upper punch;

the center pin MF, from the bottom upward, has the geometric shape of a circular cylinder Z with a circular cylindrical outer face MZ;

the length of the outline of the circular cylinder Z is less than the length of the outline of the circular cylinder I and less than the length of the outline of the circular cylinder II;

the position of the center pin MF and the position of the die including the die bore along the bore axis B are fixed relative to one another during the process;

in the geometric center of the lower end face of the upper punch, a center bore $MB^O$ which is conducted into the upper punch and is connected to at least one outlet from the upper punch (gas-permeable) is formed, said center bore $MB^O$ being capable of accommodating the center pin MF to the necessary degree in the event of reduction of the starting distance A to the end distance E, and the center pin MF being able to project into it even at the starting distance A;

the axes of symmetry of the die bore, of the circular cylinder I, of the circular cylinder II, of the center bore $MB^O$, of the center pin MF and of the center bore $MB^U$ are on a common straight line L running vertically through the die bore;

the die bore, along its bore axis, has a longitudinal section I over whose length I the geometric shape of the inner wall of the die bore corresponds to that of the outer face of a circular cylinder KZ, and which is adjoined at its upper end directly by a longitudinal section II of the die bore which is directed upward and has the length II;

the dimensions of the longitudinal section I of the die bore and of the circular cylinder I are such that the lower punch, during the process (the reduction of the starting distance A to the end distance E), is always conducted in each case sliding into the die bore at least for part of the length (preferably for a length of at least 10%, or of at least 20%, or of at least 30% (but generally $\leqq 90\%$, or $\leqq 80\%$) of the length I) of the longitudinal section I with its outer face on the inner wall of the die bore;

the dimensions of the center bore $MB^U$ and of the circular cylinder Z are such that the lower punch, during the process (the reduction of the starting distance A to the end distance E), is always conducted sliding into the die bore at least in the region of the entrance of its center bore $MB^U$ into its upper end face with the inner wall of the center bore $MB^U$ on the circular cylindrical outer face MZ of the center pin MF; and on completion of compaction, the upper punch is lifted from the ringlike shaped precursor body formed and the ringlike shaped precursor body is removed from the die bore by lifting the lower punch, and a subsequent process for thermal treatment of the ringlike shaped precursor body at a temperature of $\geqq 100°$ C. in which at least a portion of its constituents is decomposed and/or converted chemically to form at least one gaseous compound and the ringlike oxidic shaped body forms, wherein the geometric shape of the inner wall of the die bore, over the length II of the longitudinal section II, from the bottom upward, corresponds to that of the outer face of a frustocone KS which widens from the bottom upward, whose cross-sectional area, at its lower end, corresponds to the cross-sectional area of the circular cylinder KZ at its upper end, with the proviso that, on attainment of the end distance E, the lower end face of the upper punch is in the longitudinal section II and the upper end face of the lower punch is not below the longitudinal section I, such that the ringlike shaped precursor body formed by the mechanical compaction of the pulverulent aggregate between the two end faces is at least partly in the longitudinal section II on attainment of the end distance E. In other words, in the process according to the invention, on attainment of the end distance E between the upper end face of the lower punch and the lower end face of the upper punch, at least part of the distance between the two end faces is in the longitudinal section II.

Advantageously in accordance with the invention, on attainment of the end distance E between the upper end face of the lower punch and the lower end face of the upper punch, at least 20% or at least 30%, preferably at least 40% or at least 50%, more preferably at least 60% or at least 70% and even more preferably at least 80% or at least 90% of the distance (or 100% of the distance, i.e. the entire distance between the upper end face of the lower punch and the lower end face of the upper punch on attainment of the end distance E) between the two end faces is within the longitudinal section II of the die bore. Full use is made of the advantage of the process according to the invention when, on attainment of the end distance E, both the lower end face of the upper punch and the upper end face of the lower punch are in the longitudinal section II of the die bore, such that all of the ringlike shaped precursor body formed by the mechanical compaction of the pulverulent aggregate between the two end faces is within the longitudinal section II on attainment of the end distance E. In the aforementioned case, it is found to be favorable when, as early as in the state of the starting distance A, both the lower end face of the upper punch and the upper end face of the lower punch are within the longitudinal section II.

The outline of the circular cylinder II in the process according to the invention, appropriately in application terms, is normally longer than or is equal in length to the outline of the circular cylinder I. In general, the two aforementioned outlines are of equal length.

Furthermore, the upper end face of the lower punch and the lower end face of the upper punch, advantageously in accordance with the invention, are in planes parallel to one another, to which the bore axis B is at right angles.

The thermal treatment of the ringlike shaped precursor bodies in the process according to the invention can be undertaken in principle either in a specific apparatus configured therefor (for example in a belt calciner) or not until within the reactor in which it is to be employed (for example in the reaction tubes of a tube bundle reactor). In the latter case, hot gases will appropriately be passed through the reaction tubes.

The compacting process according to the invention is especially of interest for the production of those ringlike shaped precursor bodies in which the end distance E (any curvature of the end faces shall not be taken into account in the determination of the distances A and E; in other words, what is meant is always the distance of the upper/lower outlines of the cylindrical outer face of the punches) is from 2 to 10 mm, or from 2 to 8 mm, or from 3 to 8 mm, or from 3 to 7 mm. In this document, they shall all be referred to specifically as ringlike shaped precursor bodies F.

Frequently, the quotient Q of the length of the outline of the circular cylinder Z (numerator) and the length of the outline of the circular cylinder I (denominator) is from 0.3 to 0.7 or from 0.4 to 0.6.

In other words, the difference formed by subtracting the radius of the outline of the circular cylinder Z from the radius of the outline of the circular cylinder I in the case of ringlike shaped bodies F is in many cases from 1 to 3 mm, or from 1 to 2 mm, or from 1.5 to 2 mm, or from 1 to 1.5 mm. The diameter of the outline of the circular cylinder I in the case of ringlike shaped bodies F is in many cases likewise from 2 to 10 mm, or from 2 to 8 mm, or from 4 to 8 mm, or from 5 to 7 mm.

In contrast to the circular cylinder, the cross-sectional area of a frustocone is not constant over the height of the frustocone, but rather increases from the top face down to the bottom face. This of course also applies to the frustocone KS which can be inscribed into the die bore over the length of the longitudinal section II in the process according to the invention and whose cross-sectional area increases from the bottom upward ("upturned frustocone").

When H is the height of the frustocone KS, it is advantageous for the process according to the invention when the widening of the frustocone KS from the bottom (from the top face) upward (to the bottom face) is such that the following relationship between the diameter DD of the top face, the diameter DG of the bottom face and the height H of the frustocone KS is satisfied:

$$0.003 \cdot H \leq DG - DD \leq 0.050 \cdot H \tag{I}.$$

Preferably, in the process according to the invention, $$0.005 \cdot H \leq DG - DD \leq 0.025 \cdot H \tag{II}.$$

More preferably, in the process according to the invention, $$0.007 \cdot H \leq DG - DD \leq 0.015 \cdot H \tag{III}.$$

The aforementioned is especially true in the case of an inventive preparation of ringlike shaped precursor bodies F.

Normally, in the process according to the invention, both the upper end face (accessible to the pulverulent aggregate) of the lower punch and the lower end face (accessible to the pulverulent aggregate) of the upper punch have the geometric shape of the end face of a circular ring cylinder. In other words, both end faces are normally circular rings which are preferably congruent. For various reasons (cf., for example, EP-A 184 790), it may, however, be appropriate to configure one or both of the aforementioned end faces (at the same time, the two outer and the two inner circles preferably remain congruent), for example, in a concave manner (i.e. the circular ring is curved inward into the interior of the punch). In this case, the corresponding face of the particular punch has the geometric shape of a circular channel (36) (=a circular depression; in the case of production of ringlike shaped precursor bodies F, the channel depth is generally≦2 mm). The end face of the ringlike shaped precursor body produced in accordance with the invention which results therefrom in each case is then correspondingly not planar, but rather curved outward (convex). Such a configuration is found to be advantageous especially in the case of shaped support bodies produced in accordance with the invention. As a result of the curved end faces, the production of supported or coated catalysts resulting therefrom gives rise to a minor degree of formation of undesired pairs or triplets of the resulting shaped catalyst bodies. The radius of such a curvature is generally from 0.4 to 5 times the external diameter of the circular cylinder I. Otherwise, the statements made in EP-A 184 790 regarding the advantage of curved end faces of hollow cylinders apply correspondingly.

In principle, the profile of the upper face of the lower punch and/or the profile of the lower face of the upper punch in the process according to the invention can, however, also be configured in any other manner known for tablets (especially pharmaceutical tablets). For example, one or both of the abovementioned end faces can also be configured in a convex manner. It is also possible for one of the two end faces to be configured in a concave mariner and the other in a convex manner. In the case of production of ringlike unsupported catalysts, both end faces are, however, preferably configured in a planar manner.

The external diameter of the lower punch in the process according to the invention is typically marginally less than the internal diameter of the die bore in the longitudinal section I, such that the lower punch can be introduced into the die bore sliding axially with its outer wall on the inner wall of longitudinal section I of the die bore. Since, on attainment of the end distance E, furthermore, not only the lower end face of the upper punch but preferably also the upper end face of the lower punch is in the longitudinal section II of the die bore, the external diameter of the lower punch in the process according to the invention is thus regularly less than the internal diameter of the die bore at the level of the upper end face of the lower punch on attainment of the end distance E. Correspondingly, in the process according to the invention, the external diameter of the upper punch is, appropriately in application terms, normally somewhat smaller than the internal diameter of the die bore at the level of the lower end face of the upper punch on attainment of the end distance E. In the aforementioned manner, it is ensured that both the lower punch and the upper punch can move comparatively freely within the relevant longitudinal sections of the die bore within the scope required in accordance with the invention.

Furthermore, the annular gaps which thus exist between the lower (and upper) outline of the upper punch (and lower punch) and the inner wall of the die bore, at the state of the starting distance A and at the state of the end distance E, form outlets for the gas phase (normally air or nitrogen) compressed by reducing the die fill chamber in the course of the compaction operation (compression operation). In order to ensure a very homogeneous annular gap, it is possible, for example, to proceed as described in DE-A 197 14 430 with regard to the production of circular cylindrical shaped bodies by tableting pulverulent aggregate. The sliding of the lower punch on the inner wall of the die bore of longitudinal section I is found to be a significant advantage of the inventive procedure in this connection.

However, the above-described annular gaps are also the cause of the fact that, on the pressing produced in accordance with the invention, a burr can form to a minor degree both in the region of the bottom face and in the region of the top face. The compaction of the pulverulent aggregate within a burr is less marked than in the bulk of the compact obtained in accordance with the invention. The removal of the burr from the ringlike shaped precursor body is therefore possible comparatively easily later in the processing thereof. In general, the burrs break off of their own accord, for example in the course of fracture screening to be performed as described in German application 102007028332.8, and are removed.

Otherwise, the width of the above-described annular gaps has to be guided by factors including the granularity of the pulverulent aggregate to be compacted in accordance with the invention. In other words, the width of the annular gaps should generally be limited such that it is not greater than twice (better is not greater than) the longest dimension of the powder grain which occurs most frequently in the pulverulent aggregate to be compacted (the longest dimension of a powder grain is the longest direct straight line connecting two points on the surface of the powder grain; when the pulverulent aggregate consists of secondary grain obtained by agglomeration of primary grain, it is generally appropriate to judge the annular gap width which is still tolerable by referring to the longest dimension of the primary grain). In the context of the inventive production of ringlike shaped precursor bodies F, the aforementioned annular gap widths are generally a few (normally less than ten, usually less than five) hundreds of millimeters, and this is also true when both end faces are in the longitudinal section II on attainment of the end distance E. In this case too, the outline of the circular cylinder II is preferably of equal length to the outline of the circular cylinder I. In principle, the die bore in the process according to the invention may consist only of longitudinal sections I (31) and II (32) (may have only the longitudinal sections I and II).

Dies with such die bores shall be referred to in this document as "dies with a simple frustocone". A longitudinal section through dies of this type is shown by way of example by FIGS. 2a and 2b of this document (at its upper end and at its lower end, the die bore is slightly rounded appropriately in application terms, in order to minimize the risk of injury by sharp edges; generally, FIGS. 1 to 8 of this document, in the detail of their drawings, follow the specifications in "Tabellenbuch Metall", Verlag Europa Lehrmittel, 41st edition, 1999 (D-42731-Haan Gruiten); for reasons of clarity, in FIG. 6, not all sections have been shown fully; reference is therefore made in this respect to the individual drawings). It will be appreciated that the longitudinal sections I and II of the die bore of a die may be adjoined directly either in the upward or downward direction by further longitudinal sections.

What is essential to the invention is merely that the lower punch (the upper punch) can be introduced into the longitudinal section I (into the longitudinal section II) through any further longitudinal sections which adjoin the longitudinal section I (the longitudinal section II) of the die bore in the downward (upward) direction.

For economic reasons in particular, it is particularly advantageous in the process according to the invention to use dies whose die bore is such that its longitudinal section I is not only adjoined at its upper end directly by a longitudinal section II directed upward, but also at its lower end by a longitudinal section directed downward (referred to in this document as longitudinal section II* (33)), in which the geometric shape of the inner wall of the die bore, over the length II* of the longitudinal section II*, likewise corresponds to the outer face of a frustocone whose cross-sectional area at its upper end corresponds to the cross-sectional area of the circular cylinder KZ at its lower end (referred to in this document as frustocone KS*), but with a cross section widening in the downward direction (the diameter of the top face, the diameter of the bottom face and the height of the frustocone KS* preferably also satisfy at least one of the relationships (I), (II) or (III)). Dies with die bores which have only the longitudinal sections II*, I and II are referred to in this document as "dies with a double frustocone" (of course, the longitudinal sections II and II* may in principle also be adjoined directly by further longitudinal sections, provided that the particular punch can be introduced into them).

Advantageously in accordance with the invention, the geometric dimensions of longitudinal section II* correspond to those of longitudinal section II. Dies of the aforementioned type are particularly advantageous in that the inventive compaction can be carried out, for example, initially in the upper half of longitudinal section I and/or in longitudinal section II of the die bore. When the inner wall of the die bore in the aforementioned region is worn therein owing to repeated performance of the process, the die can simply be upturned (rotated by 180° about an axis at right angles to the die bore) and the inventive compaction can subsequently be carried out in the other half of longitudinal section I and/or in longitudinal section II* of the die bore. For the process according to the invention, it is very particularly advantageous to perform it with dies whose die bore consists only of a longitudinal section I and a longitudinal section II which adjoins it directly at its upper end, and a longitudinal section II* which adjoins it directly at its lower end and wherein the geometry of longitudinal section II of the die bore is congruent to the geometry of longitudinal section II* of the die bore (="die with congruent double frustocone").

In addition, it is expedient in application terms when the length II (height) of the longitudinal section II (and the length II* of the longitudinal section II*) of the die bore of the die used to perform the process according to the invention (i.e. the height H of the frustocone KS (and of the frustocone KS*)) is up to four times, preferably up to three times or up to twice or one and a half times, the axial end distance E.

In other words, processes advantageous in accordance with the invention are those processes according to the invention for which:

$$4 \cdot \text{end distance } E \geq H \geq 1 \cdot \text{end distance } E \qquad (IV);$$

or $$3 \cdot \text{end distance } E \geq H \geq 1 \cdot \text{end distance } E \qquad (V);$$

or $$1.5 \cdot \text{end distance } E \geq H \geq 1 \cdot \text{end distance } E \qquad (VI);$$

or $$3 \cdot \text{end distance } E \geq H \geq 1.5 \cdot \text{end distance } E \qquad (VII);$$

or $$2 \cdot \text{end distance } E \geq H \geq 1.5 \cdot \text{end distance } E \qquad (VIII).$$

In general, in the process according to the invention, the length I of longitudinal section I will be greater than the length II of longitudinal section II (and greater than the length II* of longitudinal section II*). However, the length I of longitudinal section I may also be less than the length II of longitudinal section II (and less than the length II* of longitudinal section II*).

Typically, the length I will, however, not be more than three times the length II (than three times the length II*).

Frequently, the length I is not more than twice (or not more than) the length II (than twice (or not more than) the length II*).

Normally, the length I is not less than 0.1 times (or not less than 0.2 times) the length II (than 0.1 times or 0.2 times the length II*).

In many cases, the length I is from 0.1 to 1 times or from 0.5 to 1 times the length II (or the length II*).

All of the above applies, as is also otherwise the case in this document, especially to the case of an inventive production of ringlike shaped precursor bodies F.

In particular, all statements in this document apply to an inventive production of ringlike shaped precursor bodies F in the course of whose preparation, on attainment of the end distance E, both the upper end face of the lower punch and the lower end face of the upper punch are within longitudinal section II (or within longitudinal section II*) of the die bore. Such a production of ringlike shaped precursor bodies F is referred to in this document, in the narrower sense, as a production of ringlike shaped precursor bodies $F^{LII}$ (irrespective of the quantitative dimensions of the ringlike shaped precursor bodies produced in accordance with the invention, those in the course of whose production, on attainment of the end distance E, both the upper end face of the lower punch and the lower end face of the upper punch are within longitudinal section II (or within longitudinal section II*) of the die bore shall be referred to in this document as "ringlike shaped precursor bodies LII").

One reason for the advantageousness of processes according to the invention to which at least one of relationships (IV) to (VII) apply is that, especially in the course of production of a relatively large batch of ringlike shaped precursor bodies LII, the inventive compaction can initially commence in the upper part of the longitudinal section II (i.e., at the state of the starting distance A, both the upper end face of the lower punch and the lower end face of the upper punch are within the upper part of longitudinal section II; advantageously in accordance with the invention, at the start of the process, at the state of starting distance A, the lower face of the upper punch will be positioned such that it concludes flush with the upper end of longitudinal section II). With increasing wear on the inner wall of the upper part of longitudinal section II of the die bore, at the state of starting distance A, both the lower end face of the upper punch and the upper end face of the lower punch will then be shifted downward within the die bore. The ringlike shaped precursor bodies which result in the case of such a procedure (for example ringlike shaped precursor bodies LII or ringlike shaped precursor bodies $F^{LII}$) are geometrically similar to one another such that they can be used equivalently to geometrically homogeneous shaped precursor bodies (for example as catalysts or catalyst supports). In particular cases (cf., for example, German application 102007017080.9), a defined variance in the shaped body geometry over a production batch may even be advantageous. In this context, it should be noted that the transition from the ringlike shaped precursor body to the oxidic shaped body by thermal treatment of the former is generally accompanied by a change in the shaped body geometry.

Figure 3A:
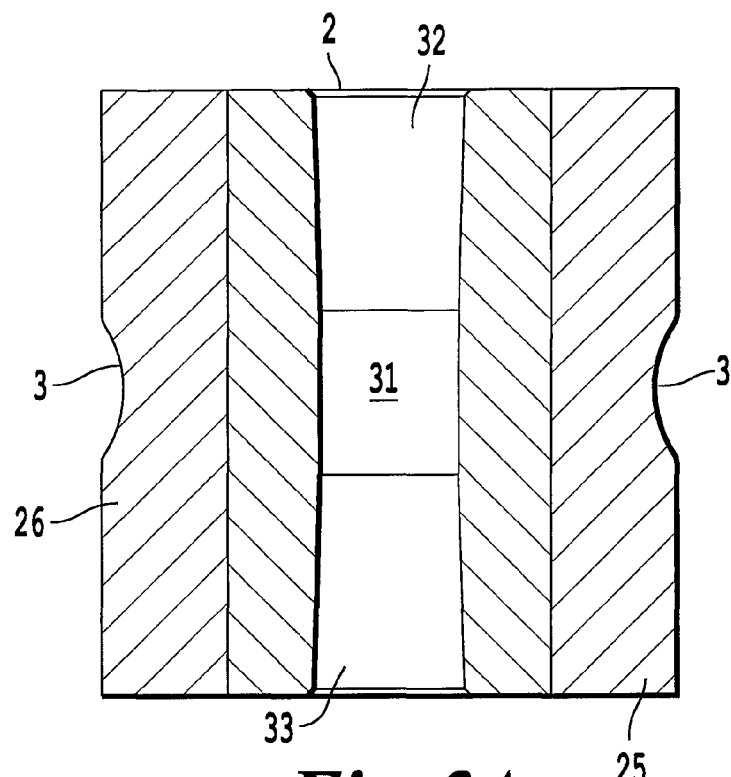
FIGS. 3a and 3b: A longitudinal section through dies with congruent double frustocone.
Figure 3B:
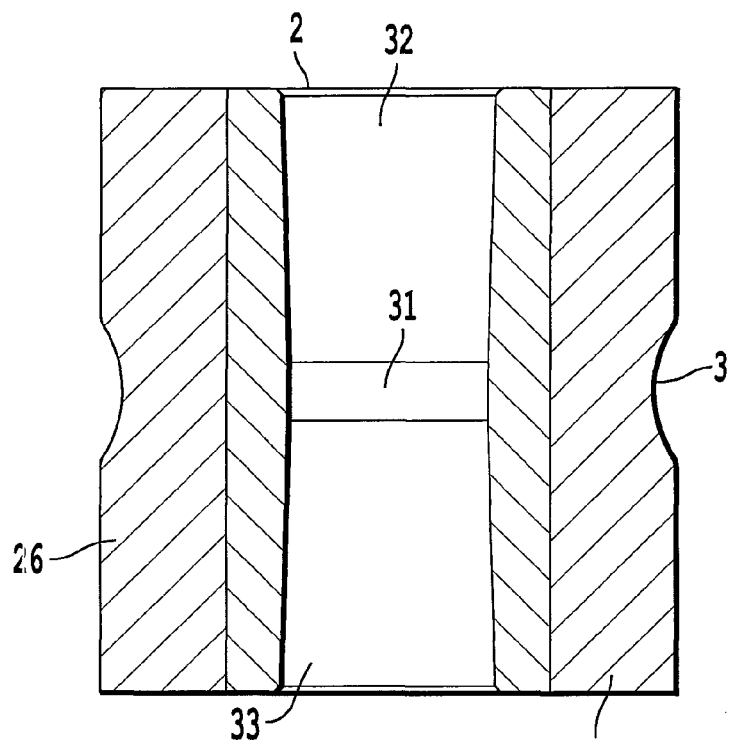

A longitudinal section through dies with congruent double frustocone which are suitable in accordance with the invention is shown by way of example by FIGS. 3a and 3b.

What is essential to the process according to the invention is that, in the geometric center of the lower end face of the upper punch, a center bore $MB^O$ which is conducted into the upper punch and is connected to at least one outlet from the upper punch is formed, said center bore $MB^O$ being capable of accommodating the center pin MF to the necessary degree in the event of reduction of the starting distance A to the end distance E, and the center pin MF being able to project into it even at the starting distance A. The center pin MF in the process according to the invention will already project into the center bore $MB^O$ at the state of the starting distance A especially when, as already described, the inner wall of the die bore is already worn in the upper part of longitudinal section II, and the inventive compaction is shifted for this reason into the part of longitudinal section II further down.

When, in the process according to the invention, the upper punch is lowered in the course of the compaction operation, the center bore $MB^O$ (35) must, however, accommodate the center pin MF: in each case to the extent to which the upper punch is lowered. Since the center bore $MB^O$ (in contrast to the center bore $MB^U$ (37) which is conducted through the lower punch) is not normally conducted through the upper punch, appropriately in application terms, at least one outlet (34) is required, to which the center bore $MB^O$ is connected and through which that gas phase that the center pin MF displaces when it is accommodated into the center bore $MB^O$ in the course of lowering of the upper punch can escape (is discharged). In general, the at least one outlet is likewise configured as a bore which runs obliquely to the center bore $MB^O$.

FIGS. 4a, 4b, 4c and 4d show longitudinal sections through appropriate upper punches provided with at least one outlet, the actual upper punch in the context of this invention meaning merely the neck which ends in circular cylindrical (or annular) form in the downward direction in these figures. The overall figure shows in each case the configuration of the inventive upper punch as a so-called upper "inlay punch", to which reference will be made later in this document.

Figure 5A:
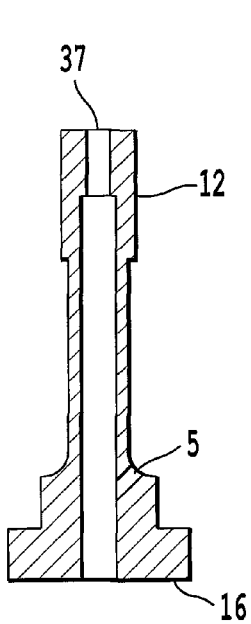
FIG. 5a shows a longitudinal section through a lower punch in which the center bore is configured with slight widening below the region of its entrance into the upper end face of the lower punch.
Figure 5B:
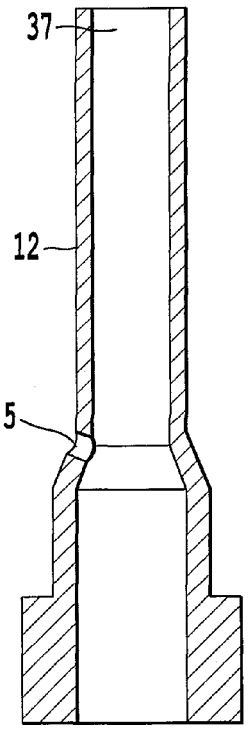
FIG. 5b shows a longitudinal section through a lower punch in which the center bore is configured with constant cylindrical cross section over the entire length of the lower punch.

The connection of the center bore $MB^O$ to at least one outlet is of particular significance especially when at least the entrance into the center bore $MB^O$ is preferably configured in circular cylindrical form such that the outer face of the circular cylinder Z (of the circular cylindrical center pin MF), when it is accommodated into the center bore $MB^O$, slides along its inner wall at least in the entrance region thereof. Preferably in accordance with the invention, the center bore $MB^O$ is configured such that the geometry of its inner wall corresponds to the outer face of a circular cylinder along its entire longitudinal axis. In this case, the dimensions of the circular cylindrical center pin MF and of the center bore $MB^O$ are preferably configured such that the outer face of the circular cylindrical center pin MF (of the circular cylinder Z) slides over the inner wall of the center bore $MB^O$ within the entire extent of its accommodation into the center bore $MB^O$. In contrast, the center bore $MB^U$ is frequently configured with slight widening below the region of its entrance into the upper end face of the lower punch, as shown, for example, in longitudinal section through a lower punch in FIG. 5a. In contrast FIG. 5b shows a longitudinal section through a lower punch in which the center bore $MB^U$ is configured with constant cylindrical cross section over the entire length of the lower punch. In FIGS. 5a and 5b too, the lower punch in the (context of this invention means merely the neck which ends in circular cylindrical (or annular) form in the upward direction in these figures. The overall figure shows in each case the configuration of the inventive lower punch as a so-called "lower inlay punch", to which reference will be made later in this document. The orifice of the center bore $MB^O$ in the upper end face of the lower punch and the orifice of the center bore $MB^O$ in the lower end face of the upper punch are normally configured congruently.

When the die is one with a congruent double frustocone, the length of a surface line of the circular cylinder I is generally not greater than the sum of the length II and 0.7 times the length I (and 0.5 times the length I). When the lower punch is configured as a lower inlay punch, it is advantageous in accordance with the invention when the cross section of the inlay punch, where it holds the lower end of the lower punch, has a smaller cross section compared to the cross section of the circular cylinder I. Such a configuration enables the discharge of Fine particles which have become caught between the wall of the die bore and the outer face of the circular cylinder I, in the course of lowering of the lower punch into longitudinal section II*.

According to the invention, the center pin MF has, from the bottom upward, the geometric shape of a circular cylinder Z with a circular cylindrical outer face MZ.

Furthermore, it is essential to the invention that the position of the center pin MF and the position of the die including the die bore are fixed relative to one another along the bore axis B during the process. The fixing of the die is in practice generally undertaken by inserting the die so as to fit exactly into a corresponding accommodating orifice within a die table.

In addition, it is normally fixed by means of a securing screw, which can lead, for example, from the die table edge horizontally to the accommodating orifice for the die. When the die table has several accommodating orifices placed, for example, equidistantly on the circumference of a circle, the additional fixing of dies inserted into them can also be effected such that the securing screw is placed on a part circle between two accommodating orifices, which fixes the two dies inserted into them with respect to one another.

For the fixing of the center pin MF, center pin holders are generally used. In order to facilitate the fixing, the center pin MF is normally equipped at its lower end with a head (27) which is accommodated by an intermediate space (28) (slot) of the center pin holder manufactured for an exact fit. In the direction toward the aforementioned head, the actual center pin may be adjoined by a widened cross section which eases the fixing of the center pin (cf., for example, in FIG. 6 and FIG. 1). The center pin holder itself is, appropriately in application terms, generally likewise screwed firmly onto the die table.

The present invention shall, however, also comprise those embodiments in which the center pin MF, from the bottom upward, first has the geometric shape of a circular cylinder Z with a circular cylindrical outer face MZ, but then narrows conically in the upward direction. This is especially true when the center pin MF which, from the bottom upward, is initially circular cylindrical narrows conically in the upward direction within the longitudinal section II of the die bore (and does not widen any further up to its upper end). In this case, the center pin MF, from the bottom upward, may have the geometry of a circular cylinder Z to which is then attached, within the longitudinal section II, a frustocone KM (30) narrowing in the upward direction (the cross section of the circular cylinder Z corresponds in this case to the cross section of the bottom face of the frustocone KM). The height of the frustocone KM may correspond to the length of longitudinal section II (which is preferred in accordance with the invention), but may also be shorter (in the latter case, the proportion of the center pin having circular cylindrical geometry extends from the bottom upward into the longitudinal section II). The reason for the advantageousness of this ending of the center pin MF in the upward direction as a frustocone KM, in a similar manner to the advantageousness of the geometry of longitudinal section II of the die bore itself, is that, owing to the conical narrowing of the center pin MF in the upward direction, when the ringlike shaped body formed is removed from the die bore by lifting the lower punch, the rollering friction between the outer wall (the outer face) of the center pin MF and the outer face of the cavity of the ringlike shaped body formed (for example over the length of longitudinal section II) can essentially be eliminated (for example in the case of production of ringlike shaped precursor bodies LII or $F^{LII}$). However, the advantage resulting from these facts is comparatively limited, since the outer face of the frustocone KM is normally significantly smaller compared to the outer face of the frustocone KS for the same height.

When H* is the height of the frustocone KM, it is advantageous when the narrowing of the frustocone KM from the bottom (from the bottom face) upward (to the top face) is such that the following relationship between the diameter DG* of the bottom face and the height H* and the diameter DD* of the top face of the frustocone KM is satisfied:

$$0.005 \cdot H^* \leq DG^* - DD^* \leq 0.015 \cdot H^* \quad \text{(IX)}.$$

Preferably:

$$0.007 \cdot H^* \leq DG^* - DD^* \leq 0.013 \cdot H^* \quad \text{(X)}.$$

More preferably:

$$0.009 \cdot H^* \leq DG^* - DD^* \leq 0.011 \cdot H^* \quad \text{(XI)}.$$

It should be noted, in the case of employment of a center pin MF which narrows, for example, conically toward its upper end, that, owing to the cross section which is not constant over the height H* of the frustocone KM, an annular gap necessarily remains when the frustocone KM is accommodated into the center bore $MB^O$ (the outer face of the frustocone KM does not slide over the inner wall of the center bore $MB^O$). The width thereof which is still tolerable again has to be guided by the particle size of the pulverulent aggregate to be compacted. Normally, the cross section of the center bore $MB^O$ in the case of a center pin MF which narrows conically in the upward direction will be such that, when its circular cylindrical section is accommodated into the center bore $MB^O$ with its circular cylindrical outer face, it would slide along the inner wall of the center bore $MB^O$ at least in the region of the entrance thereto. FIG. 7 shows, by way of example, a longitudinal section through a center pin MF which has, from the bottom upward, exclusively the geometric shape of a circular cylinder Z, while FIG. 8 shows, by way of example, a longitudinal section through a center pin MF which, from the bottom upward, first has the geometry of a circular cylinder Z and then narrows conically up to its upper end.

Quite generally, it is preferred in the process according to the invention when the upper end of longitudinal section II of the die bore, the upper (planar) end face of the center pin MF and the upper (planar) end face of the die conclude flush with one another (i.e. do not protrude).

This is true especially in the case of automatic performance of the process according to the invention, since the aforementioned arrangement facilitates (favors) the automatic introduction of the pulverulent aggregate into the fill chamber.

In general, the die has a planar upper end face. Appropriately in application terms, the lower end face of the die also has a planar configuration. The die preferably (apart from the die bore) has the shape of a circular cylinder with a planar upper end face and a planar lower end face. In the outer wall of the circular cylinder, a horizontal ring or a round depression advantageously runs at half the height. It serves to fix the die in the die table by means of one or more securing screws.

In principle, in the process according to the invention, the starting distance A can be reduced to the end distance E by actively moving both (the lower punch and the upper punch) punches toward one another. It will be appreciated, however, that it is also possible to proceed such that the lower punch maintains its position and only the upper punch is moved (lowered).

In general, it is advantageous for a very uniform surface hardness of the compact (ringlike shaped precursor body) resulting in the process according to the invention when the reduction of the starting distance A to the end distance E involves actively moving upper punch and lower punch together toward one another (the upper punch is lowered; the lower punch is lifted). In this case, the required compression pressure onto the pulverulent aggregate is exerted equally by the upper punch and by the lower punch, which causes a more homogeneous side crushing strength of the resulting compact over its height.

This also results in a shaped precursor body with a more homogeneous bulk density over its entire dimension. After the thermal treatment, the latter causes a more homogeneous pore structure and, based on the latter, improved catalyst performance.

In principle, the process according to the invention can be performed either manually or automatically. For reasons of economic viability, automatic practice of the process according to the invention is preferred. Essentially two machine types can be used for this purpose, which are distinguished from one another in the specialist literature as "eccentric press" and as "rotary press". In the eccentric press, only the upper punch exerts the actual compression force by virtue of its downward motion with the aid of the eccentric disk, while the lower punch is stationary during the compression and moves upward (is lifted) only for the final expulsion of the compact (of the ringlike shaped precursor body). In the eccentric press, the die is stationary. It is at rest in the die plate on the fixed die table. The die may have one or (successively) more die bores (and hence die fill chambers). In each die bore, a punch pair consisting of upper punch and lower punch move in the rhythm of the eccentric disk. The center pin MF is likewise stationary and is conducted through the die bore and the lower punch and is secured to the die plate with a center pin holder. According to whether the die has one or more die bores (die fill chambers), reference is made to a single-punch or multipunch die. Correspondingly, a distinction is drawn between single and multiple molds. The single mold consists of one die with a die bore and a center pin MF and an upper punch and a lower punch. A multiple mold consists correspondingly of a die having two or more die bores and with a corresponding number of center pins MF and of upper and lower punches. The decision as to whether single or multiple molds are used is made essentially on the basis of the size of the ringlike shaped precursor body and the pressure that the machine can impart. The upper limit employable in the process according to the invention is at about a fifty-bore mold. Since the die is stationary in the eccentric press, a filling funnel including filling shoe which comprises the pulverulent aggregate to be compacted in accordance with the invention normally slides forward and backward on the die table in order to ensure homogeneous filling of the fill chamber or of the fill chambers of the dies. Filling of the fill chamber, compaction (compression) and discharge of the ringlike shaped body in the eccentric press proceed in this manner in periodically repeating succession and together correspond in each case to a full eccentric rotation.

In the simplest case, the working cycle in the eccentric machine therefore proceeds as follows. The lower punch is at first in its fill position within the die bore. The filling shoe slides over the die whose upper planar end face concludes flush with the upper planar end face of the center pin MF, the filling material (the pulverulent aggregate) passing into the die bore and onto the upper end face of the lower punch. When the filling shoe slides back, the upper punch moves downward until its lower end face is in contact with the filling material. The pulverulent aggregate has thus been introduced into the fill chamber and the state of the starting distance A has been attained. Further downward motion of the upper punch (with the lower punch fixed) compacts the filling material to the ringlike shaped precursor body until the end distance E with accompanying pressure has been attained. Subsequently, the upper punch is lifted from the ringlike shaped precursor body formed and the ringlike shaped precursor body is removed from the die bore by (generally somewhat retarded) lifting of the lower punch. In general, the lower punch is lifted to such an extent that the lower side of the shaped precursor body formed just reaches the level of the upper side of the die. While the front edge of the filling shoe shifting forward now shifts the shaped precursor body from the die, the lower punch is lowered back to its filling position, and the die bore is filled again.

DESCRIPTION OF THE DRAWINGS

Figure 9:
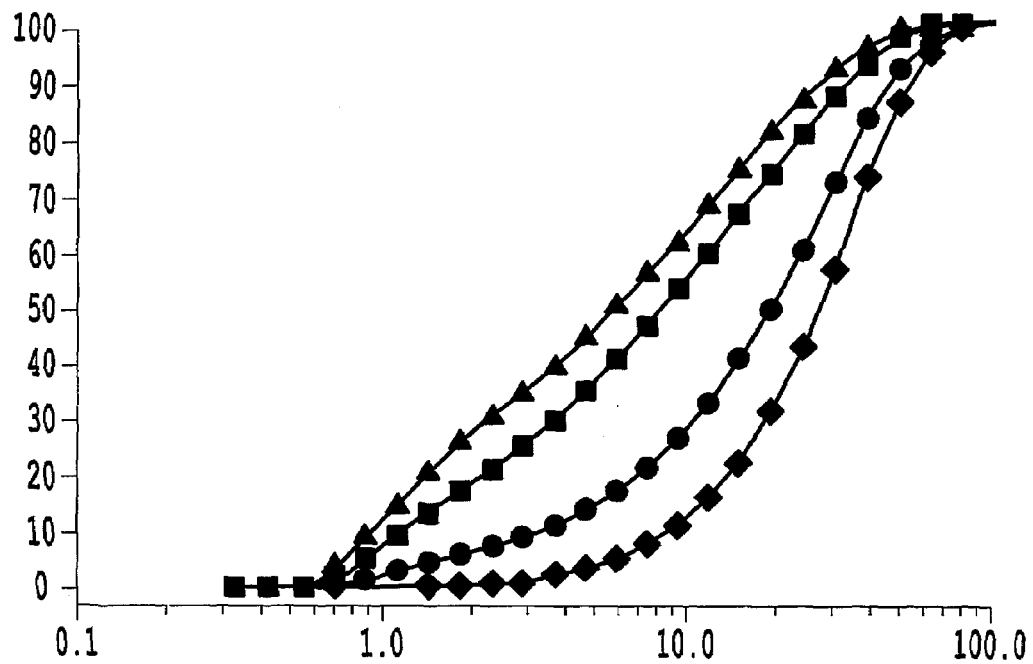
FIG. 9 shows the particle diameter distribution of the spray powder for a starting composition 1 as a function of the dispersion pressure employed.

FIG. 9 shows the particle diameter distribution of the spray powder for the starting composition 1 used in II. as a function of the dispersion pressure employed. The abscissa shows the particle diameters in a logarithmic plot in Am. The ordinate shows the proportion by volume in % of the total particle volume that has the appropriate particle diameter as a function of the dispersion pressure employed:

triangle: Dispersion pressure=2 bar abs.
square: Dispersion pressure=1.5 bar abs.
circle: Dispersion pressure=1.2 bar abs.
rhombus: Dispersion pressure=1.1 bar abs.

Figure 10:
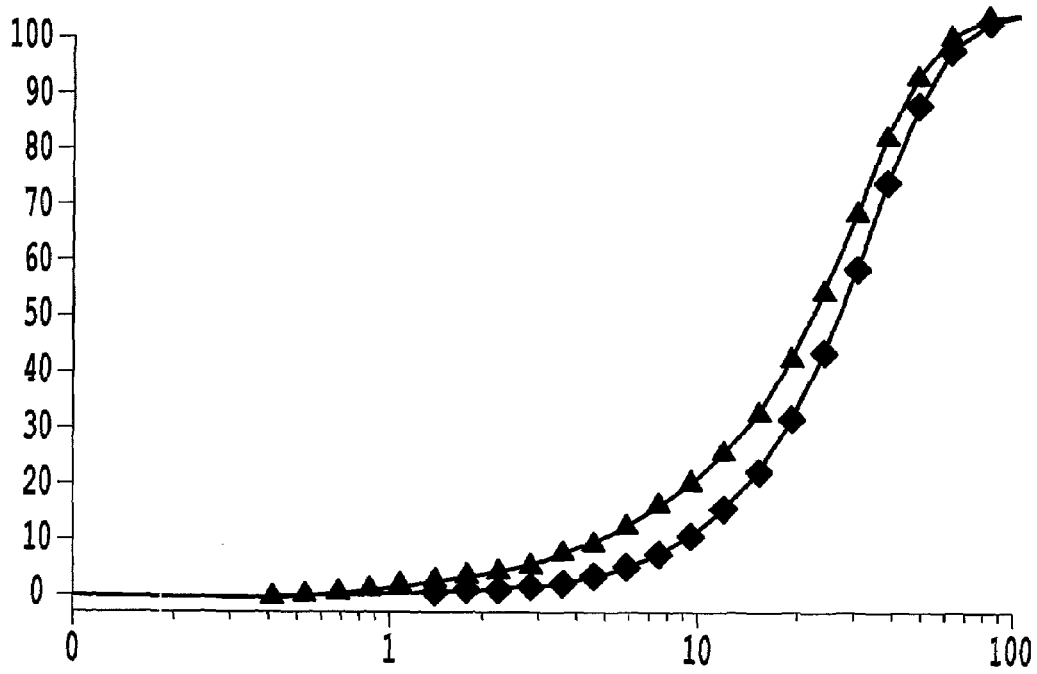
FIG. 10 shows the particle diameter distribution of the resulting spray powder for a starting composition 2 as a function of the dispersion pressure employed.

FIG. 10 shows the particle diameter distribution of the resulting spray powder for the starting composition 2 used in II. as a function of the dispersion pressure employed. The abscissa shows the particle diameters in a logarithmic plot in pm. The ordinate shows the proportion by volume in % of the total particle volume that has the appropriate particle diameter as a function of the dispersion pressure employed:

triangle: Dispersion pressure=2 bar abs.
rhombus: Dispersion pressure=1.1 bar abs.

For the other Figures the "Description" corresponds to the "Brief Description", however additionally the numerical addresses used in the individual Figure have the following meaning:

| | |
|---|---|
| 1 = | a die |
| 2 = | a die bore |
| 3 = | a horizontal ring milled out in the outer wall of a die |
| 4 = | upper inlay punch |
| 5 = | lower inlay punch |
| 6 = | lower screw cap |
| 7 = | upper screw cap |
| 8 = | lower shaft |
| 9 = | upper shaft |
| 10 = | lower shaft head of the lower shaft |
| 11 = | upper shaft head of the upper shaft |
| 12 = | actual lower punch |
| 13 = | actual upper punch |
| 14 = | base of the upper inlay punch |
| 15 = | circular pressure face of the upper shaft |
| 16 = | circular ring-shaped base of the lower inset punch |
| 17 = | circular ring-shaped pressure face of the lower shaft |
| 18 = | center pin MF |
| 19 = | center pin holder |
| 20 = | accommodating orifice of the die table |
| 21 = | the die table tongue |
| 22 = | guide bore for a shaft |
| 23 = | die table brow |
| 24 = | die table chin |
| 25 = | side of the die in contact with the die pore |
| 26 = | side of the die facing away from the die bore |
| 27 = | head of the center pin MF |
| 28 = | intermediate space of the center pin holder to accommodate the head (27) |
| 29 = | |
| 30 = | frustocone KM |
| 31 = | longitudinal section I of the die bore |
| 32 = | longitudinal section II of the die bore |
| 33 = | longitudinal section II* of the die bore |
| 34 = | outlet to which the center bore MBo is connected |
| 35 = | the center bore MBo |
| 36 = | face of a punch having the geometric shape of a circular channel |
| 37 = | the center bore MBu |

In the rotary press, in contrast, the filling funnel including filling shoe is stationary, and a die table in which the dies are at rest rotates, the die bores being moved past below the filling shoe. In the case of rotation of the die tables, the individual dies (or the die bores thereof are filled in succession. The fillings are then compressed and the resulting compacts are subsequently ejected.

One die bore is thus filled, while another die filling is compacted and, at the same time, in yet another die, a ringlike shaped precursor body (the compact) is ejected. In the case of a rotation of the die table, as many ringlike shaped precursor bodies are produced as mold sets are present—in the case of use of single-punch molds. In the case of multipunch molds, it is necessary to multiply by the number of bores per die. While the eccentric press works discontinuously, rotary presses work continuously. Moreover, in rotary presses, the compression pressure is exerted equally by the upper and lower punch with the aid of pressure rollerers.

The rotary presses available on the market for performance of the process according to the invention include models for from 10 to 100 (or 80) mold sets, and each mold set may normally have up to six punches in total. While as many compacts are pressed in a normal rotary press per die table rotation as dies (multiplied by bores in the case of multiple molds) are present, so-called double rotary presses (which possess a particularly high output performance) have two pressing stations, and—in the case of single-punch mold sets—during one die table rotation, at the same time, in each case two dies are filled, two fillings are compacted and two ringlike shaped bodies are ejected. For example, for the process according to the invention, it is possible to use the KS, KIS and K III eccentric presses from Kilian, D-50735 Cologne. However, particularly suitable for the process according to the invention are rotary presses from Kilian (for example of the T series, the R series, the S series and the X series).

Particularly suitable for the process according to the invention is the Kilian RX 73 double rotary press, and also the Kilian Synthesis 700-77 A rotary press.

Also suitable for the process according to the invention are the rotary presses from Korsch AG, D-13509 Berlin, for example the Korsch PH800 and PH865 rotary presses.

The individual configuration of the upper punch, of the center pin MF, of the lower punch and of the die including die bore (i.e. of the mold) is the responsibility of the user. For application in a Kilian rotary press, the configuration thereof may, in a manner particularly advantageous to the process according to the invention, for example, be as follows (the numerical addresses relate (as always in this document) to the figures appended to this document).

The individual die (1) is manufactured such that it fits exactly into the accommodating orifice present in a die table. Disregarding the die bore (2), the die, appropriately in application terms, has the shape of a circular cylinder with a planar upper end face and a planar lower end face, in whose outer wall, at half the height, either a horizontal ring or a round depression (3) has been milled out. It serves to fix the die in the die table (for example by means of at least one securing screw which can lead, for example, from the die table edge horizontally to the accommodating orifice for the die or run over part of the circle of a die to the die adjacent thereto).

Appropriately in accordance with the invention, the upper punch (corresponding to this die) is manufactured as an upper inlay punch (4), and the lower punch (corresponding to this die) as a lower inlay punch (5). The lower inlay punch (the upper inlay punch) can be screwed by means of a lower screw cap (6) (by means of an upper screw cap (7)), into which the lower inlay punch (the upper inlay punch) can be placed, centered onto a lower shaft (8) (onto an upper shaft (9)). The lower shaft (the upper shaft) ends in a lower shaft head (10) (ends in an upper shaft head (11)), which slides in the guide rails of the rotary press. The lower inlay punch (the upper inlay punch) ends in the actual lower punch (12) (in the actual upper punch (13)) (i.e. the punch relevant in accordance with the invention is in both cases the neck in which the particular inlay punch ends).

The base (14) of the upper inlay punch (also referred to as "inset punch") rests, in the screwed-in slate, on the circular pressure face (15) of the upper shaft. The configuration as an inlay punch gives rise to high flexibility when the same shafts are used.

The circular ring-shaped base (16) of the lower inset punch rests, in the screwed-in state, on the circular ring-shaped pressure face (17) of the lower shaft. The circular ring orifice of the pressure face (17) is continued into the lower shaft as a cylindrical cavity. It can accommodate the continuation of the center pin MF (18). A lateral orifice (a groove) in the lower shaft allows the center pin MF to be positioned by means of a center pin holder (19) (fixed along the bore axis B relative to the die and the die bore thereof).

Figure 2A:
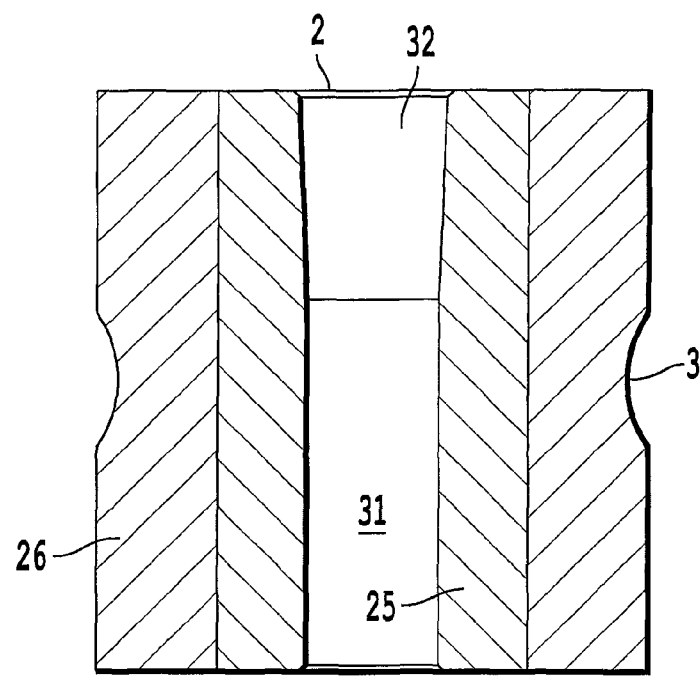
FIGS. 2a and 2b show a longitudinal section through dies with a simple frustocone.
Figure 2B:
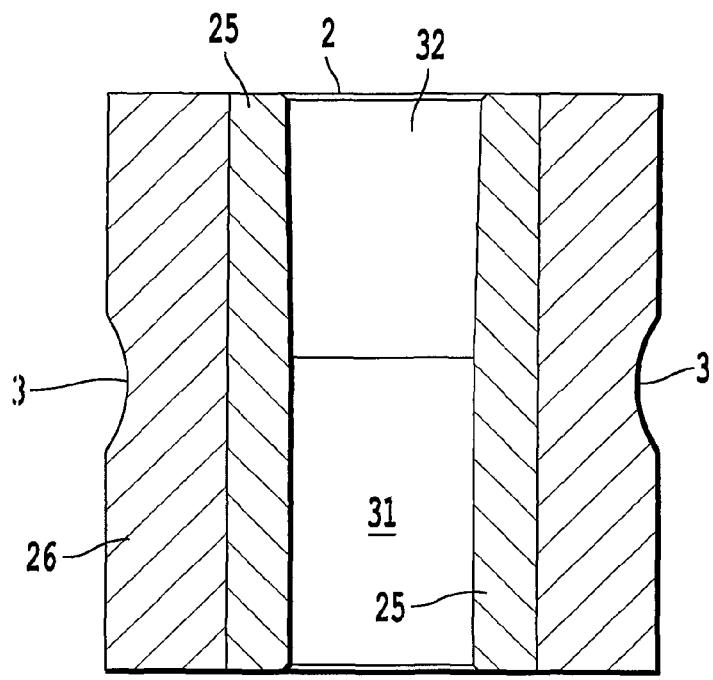

The center pin holder itself is secured on the die table by means of a screw. FIG. 1 shows, in a kind of explosion diagram, the individual elements detailed above in longitudinal section.

Figure 6:
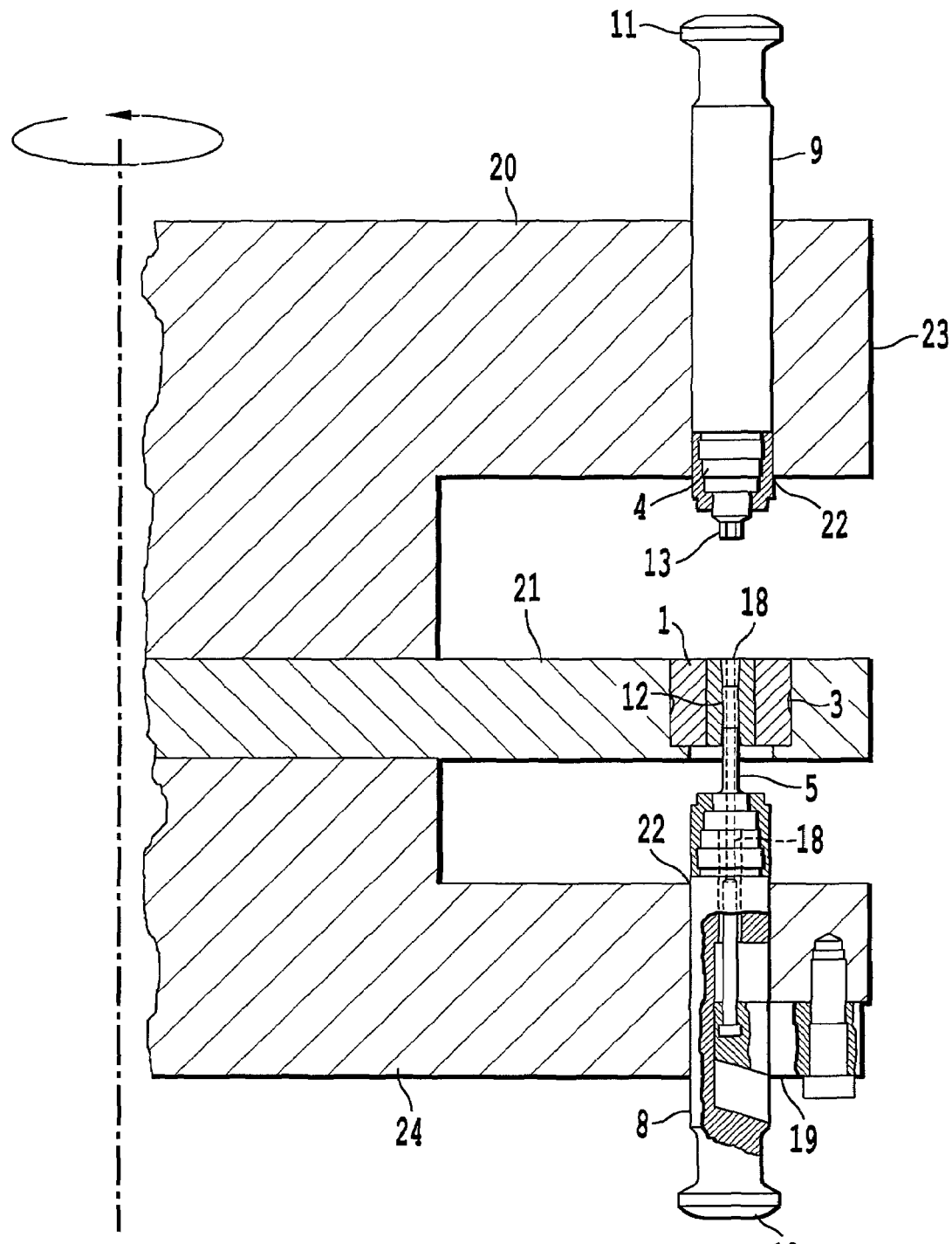
FIG. 6 shows a detail of a longitudinal section through a die table.

FIG. 6 shows a detail of a longitudinal section through the die table. It shows the die (1) inserted into the accommodating orifice of the die table (20), and the horizontal ring (3) for the fixing thereof by means of a securing screw. The portion of the die table in whose accommodating orifices the dies (1) are inserted shall also be referred to in this document as the die table tongue (21). In addition, FIG. 6 shows the guide bores (22) for shafts (8) and (9) machined in the die table above and below the accommodating orifice for the die (1). Sliding vertically by its outer face on the inner wall of the particular guide bore (22), the lower shaft (8) or the upper shaft (9) can be lifted or lowered. The portion of the die tables which comprises the guide bores for the upper shafts shall also be referred to in this document as die table brow (23). The portion of the die table which comprises the guide bores fir the lower shafts shall also be referred to in this document as die table chin (24). The center pin holder (19) is screwed to the die table (20) from below in FIG. 6. The center pin MF (18) which ends with a wider cross section in the direction toward its head leads, held by the center pin holder (19), conducted through the lower shaft and the lower inset punch, up to the planar end face of the die (1), with which the planar face of the center pin MF (18) concludes flush. Especially when multiple molds are used, the shafts should not rotate in the guide bore (22). This is achieved by means of keyways in the shaft and keys along the inner wall of the guide bore. The upper shaft head (11) and the lower shaft head (10) reside, respectively, in a stationary "upper punch guide rail" and "lower punch guide rail" which are not shown by FIG. 6. The inserted die (1) is a die with congruent double frustocone.

The mode of operation of the rotary press is now shown schematically as follows (this principle of operation is essentially the same in all rotary presses).

The die table which is driven, for example, by a screw or a toothed wheel rotates about its axis in the horizontal plane. The shafts which reside with their respective shaft head in fixed guide rails (generally stainless steel or plastic rails) follow, as the die table rotates, the height profile of the respective guide rails sliding therein. The lower shaft which bears the lower punch slides, in the course of the rotary motion of the die table, along its sliding path first up to the filling shoe, where it and hence also the lower punch are drawn downward, such that the upper end face of the lower punch is at its fill height in the die bore. Later in the rotary motion, the free space of the die bore present above the upper end face of the lower punch is filled with the fine aggregate to be compacted in accordance with the invention (the filling material) from the filling shoe. As the die table rotates further, the lower shaft and with it the lower punch are lifted, such that the upper end face of the lower punch is at its fill level height in the die bore. Excess filling material is forced upward and rounded off later in the rotary motion. The lower shaft and with it the lower punch are then drawn down again, such that the upper end face of the lower punch in the die bore is at that height to which the starting distance A relates (also referred to here as "press height"). During the filling, the upper punch is suspended above the filling shoe and then slides downward according to the course of the guide rails for the upper shaft, until its lower end face comes into contact with the fine aggregate present in the die bore. The pulverulent aggregate has thus been introduced into the fill chamber and the state of the starting distance A has been attained. Both the upper shaft head and the lower shaft head, in the course of further rotation of the die table, are each run over a pressure rollerer, and hence both the upper punch and the lower punch are pressed against the filling material introduced into the fill chamber (the lower punch is raised; the upper punch is lowered further) until the end distance E has been attained. During the compaction between the pressure rollerers, as required, a distance maintenance period can be achieved, during which the distance of upper punch and lower punch is kept constant (in the case of eccentric tableting machines, there is no time interval within which the distance between upper and lower punch remains constant; the compaction is caused only by the immersion depth of the upper punch into the pulverulent aggregate).

The distance maintenance time during which the compaction pressure is approximately constant promotes time-dependent plastic deformation operations in the aggregate to be compacted. The upper shaft is then, as a result of the profile of its guide rails, raised again, in order to lift the upper punch from the ringlike shaped body obtained. The lower shaft and with it the lower punch are raised by the sliding of the lower shaft head in the liftoff path of the guide rail and the ringlike shaped precursor body present on its upper end face is conducted out of the die bore, and stripped off by a stripper (the process according to the invention advantageously enables particularly low ejection forces; when fresh dies are used, they are generally in the range from 0.15 to 1.5 kN; in the course of further practice of the process, the ejection force required generally rises; when this rise reaches approx. 700 N, the die is normally turned over or exchanged). Via a channel, the ringlike shaped precursor body then slides into a storage vessel. In the course of the further rotary motion of the die table, the upper punch is shifted up to its highest point by the sliding of the upper shaft head within its upper sliding path, until it is again above the filling shoe.

The lower punch has now been drawn back downward (lowered) by the further sliding of the lower shaft head in its lower sliding path, such that it is likewise below the filling shoe again on the lower sliding path and its upper end face is back at the fill height in the die bore. Subsequently, the operation described is repeated with the periodicity of the rotary motion of the die table.

Figure 4A:
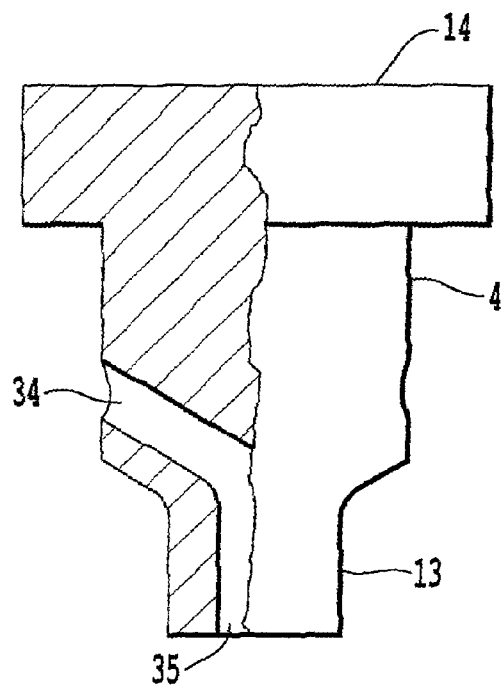
FIGS. 4a, 4b, 4c and 4d show longitudinal sections through appropriate upper punches provided with at least one outlet.
Figure 4B:
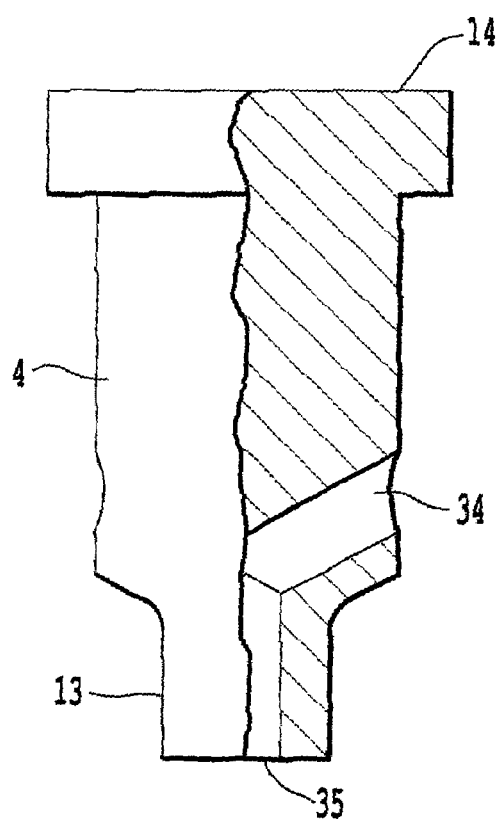
Figure 4C:
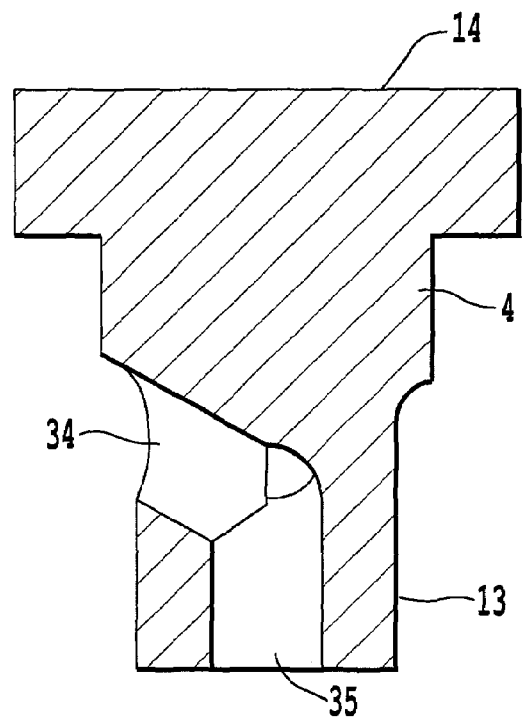
Figure 4D:
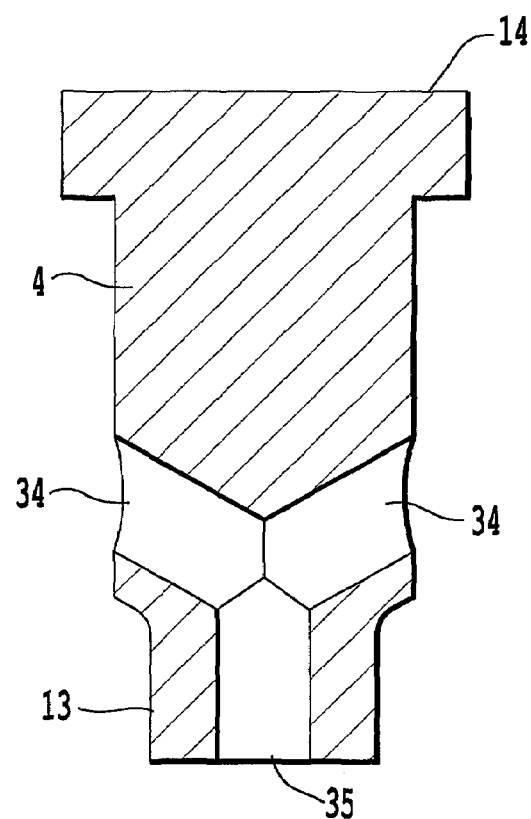
Figure 4E:
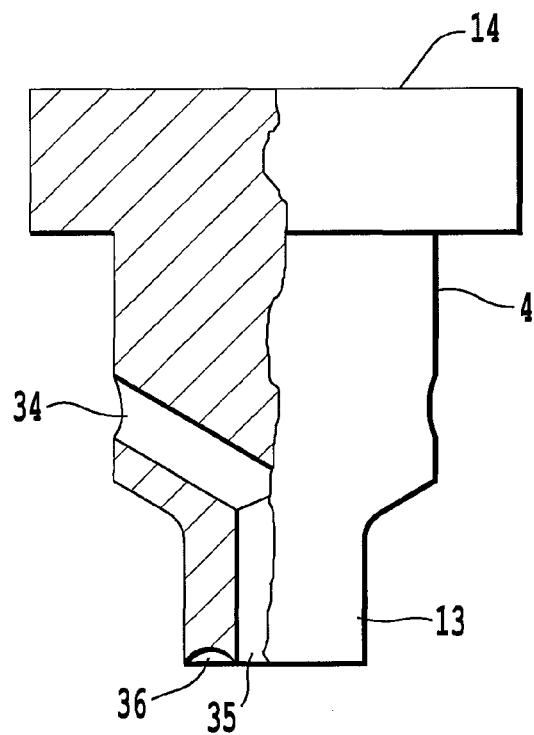
FIGS. 4e and 4f show two upper inlay punches in which the lower end face of the lower punch is not planar.
Figure 4F:
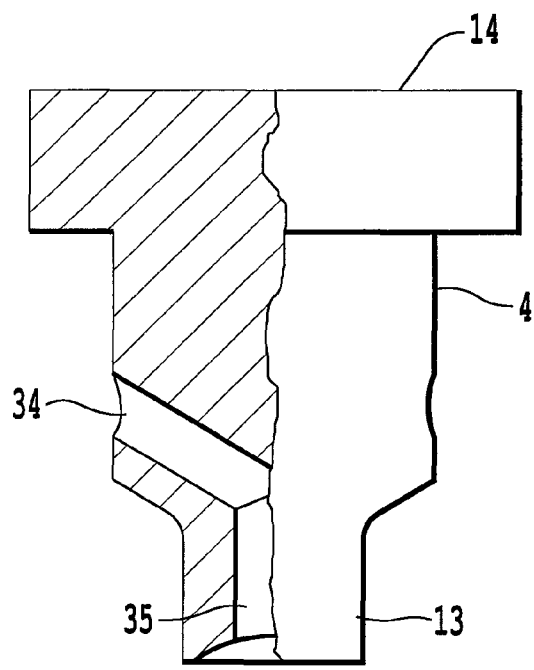
Figure 5C:
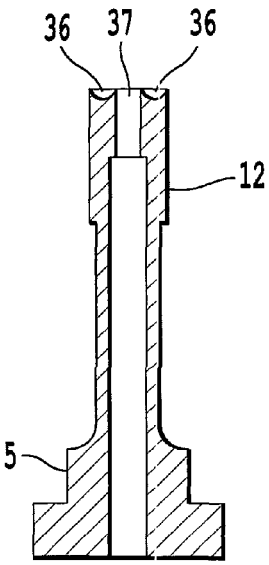
FIGS. 5c, 5d, and 5e show three lower inlay punches in which the upper end face of the lower punch is not planar.
Figure 5D:
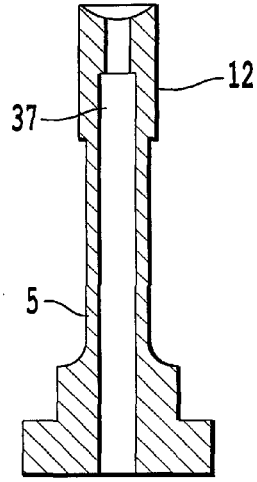
Figure 5E:
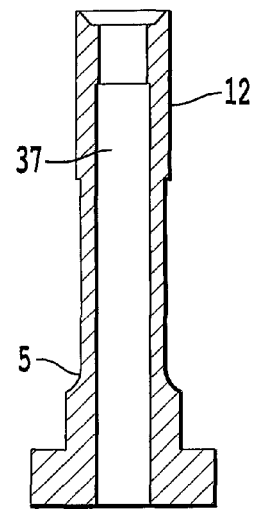

It is advantageous when the filling of the die bore with filling material proceeds as early as during the lowering of the lower punch to fill height, in order that not too much air is incorporated in the course of filling of the die bore. In the course of complete rotation of the die table, the shafts are never completely conducted out of the guide bores. Preference is given in accordance with the invention to using rotary presses in which not just one compaction operation per ringlike shaped precursor body is carried out as just described through use of a pair of pressure rollers, but rather a preliminary compaction (to the preliminary end distance $E^V$ of the two end faces) and a main compaction (to the end distance E, where $E^V>E$) per ringlike shaped precursor body are carried out through use of two pressure roller pairs arranged in close succession (the preliminary pressure roller generally, in a simple manner, has smaller dimensions than the main pressure roller. The application of preliminary compaction to a preliminary end distance $E^V$ ($>E$) of the two end faces ensures better venting in the course of compaction and more homogeneous compaction of the pulverulent aggregate, since the preliminary compaction converts the filling material to a comparatively homogeneous state of order. Generally, slow pressing is advantageous for good venting. The side wall pressure resistance of the resulting ringlike shaped precursor body can also be improved by performing, after the preliminary compaction, first a decompression and only after this the main compaction. For the sake of completeness, FIGS. 5c, 5d and 5e show three lower inlay punches in which the upper end face of the lower punch is not planar. The lower inlay punch in FIG. 5c ends in a lower punch in which the teaching of EP-A 184790 is implemented. FIGS. 4e and 4f show correspondingly configured upper inlay punches.

Useful filling shoes for the process according to the invention in the case of rotary presses are, for example, shaken filling shoes, vibratory filling shoes and stirred filling shoes. Particular preference is given, however, to using stirrer blade filling shoes. The latter have also been used in all working examples.

It should also be emphasized at this point that it is particularly advantageous for the process according to the invention to use those simple rotary presses or double rotary presses in which the die table (20) is mounted so as to be exchangeable. One such double rotary press is, for example, the Synthesis 700 double rotary press from Kilian. Another advantage of this double rotary press is that it works with preliminary compaction and main compaction. Rotary pressing machines are described, for example, in documents DE-A 2624853, DE-A 19733969 and DE-A 2435777. Otherwise, the molds for an inventive tableting have to be manufactured very precisely and the standards of the particular country which apply in this regard (for example DIN ISO 2768) should be met. The particular surfaces of the molds should be manufactured as smoothly as possible.

Especially in the case that the pulverulent aggregate to be compacted in accordance with the invention comprises at least one metal oxide (for example from the group comprising aluminum oxide, tungsten oxide, antimony oxide, zirconium oxide, bismuth oxide, molybdenum oxide, silicon oxide, magnesium oxide, and mixed oxides which comprise at least two of the metal elements present in the aforementioned metal oxides (for example mixed oxides of bismuth and of tungsten, for example $Bi_2W_2O_9$)), a metal hydroxide, a metal hydrogenphosphate and/or at least one metal nitrate (this term shall also include metal nitrate hydrates), for example cobalt nitrate, iron nitrate, bismuth nitrate, nickel nitrate, cesium nitrate, copper nitrate, calcium nitrate and magnesium nitrate (such pulverulent aggregates shall be referred to hereinafter as pulverulent aggregates HW*), it is advantageous in accordance with the invention when the upper punch and the lower punch for the process according to the invention are manufactured from tool steel with DIN materials number 1.2601 (in the case that the aforementioned punches are manufactured as inlay punches, the entire inlay punch is, appropriately in application terms, manufactured from DIN material 1.2601). Alternatively to DIN material 1.2601, the punches, especially in the aforementioned cases, may also be manufactured from DIN tool steel 1.2379.

In contrast to the punches, the die is, advantageously in accordance with the invention, manufactured, in contrast, from a material composite. Preferably in accordance with the invention, this material composite consists of a hard metal (25) on its side in contact with the die bore and advantageously of a tool steel (26) on its side facing away from the die bore. The latter preferably has the following element composition WS:

1.50 to 1.80% by wt. of C,
0.10 to 0.40% by wt. of Si,
0.10 to 0.50% by wt. of Mn,
$\geq 0$ to 0.05% by wt. of P,
$\geq 0$ to 0.05% by wt. of S,
10 to 13% by wt. of Cr,
0.50 to 0.80% by wt. of Mo,
0.10 to 1.10% by wt. of V,
$\geq 0$ to 0.60% by wt. of W, and
$\geq 0$ to 0.10% by wt. of one or more rare earth metals, and apart from these Fe and impurities resulting from the production, where the percentages are based in each case on the total weight.

Particularly preferred tool steels WS are DIN materials 1.2601 and 1.2379. In other words, appropriately in accordance with the invention, the die consists of a core of hard metal comprising the die bore and a die surround composed of a tool steel (preferably of one of the element composition WS) comprising the core of the die. A wall thickness of the hard metal in contact with the die bore of a few millimeters (for example from 1 to 10 mm, in many cases from 2 to 8 mm, or from 2 to 6 mm, or from 2 to 4 mm) is generally sufficient. This applies especially in the case of an inventive production of ringlike shaped bodies F. The wall thickness of the die surround will normally be a few centimeters (for example from 0.5 to 3 cm, or from 1 to 2 cm) (especially in the case of production of ringlike shaped precursor bodies F, e.g. $F^{LII}$).

In this document, a hard metal shall be understood to mean a sintered composite material composed of at least one hard substance selected from the group of the metal carbides, metal nitrides and metal borides (where the metal is in each case preferably at least one metal from the group consisting of W, Ti, Zr, Hf, V, Nb, Ta, Mo and Cr), and at least one soft, ductile metal from the group of Fe, Co, Ni and Cr. Sintered hard metals suitable in accordance with the invention are produced normally by (preferably very homogeneously) mixing a predominant amount (generally $\geq 80\%$ by weight, preferably $\geq 90\%$ by weight) of the high-melting hard substances (preferably at least one metal carbide) in powder form with a small amount (generally $\leq 20\%$ by weight, preferably $\leq 10\%$ by weight) of lower-melting metal powder, and heating to temperatures below the melting point of the high-melting hard substances, the temperature and duration of the heating being selected such that the hard substance sinters to form a skeleton (the hard phase) into which the metal is incorporated as a binder phase (binder). The grain size (especially of the hard substance fraction) in the hard metal powder may be, for example, from 0.2 μm to 15 μm, advantageously from 0.5 to 3 μm, particularly advantageously from 1 to 1.5 μm. Advantageously, the Rockwell hardness of the hard metal should not be below 80, its Vickers hardness should be $\geq 1500$ and the flexural strength should be $\geq 2000$ N/mm². The production of sintered hard metals is described, for example, in documents AT patent 358833, EP-A 1364732, AT patent 362943, and in the student research report "Ermüdungsverhalten des Hartmetalls G55 Co bei Raumtemperatur" [Fatigue Behavior of the Hard Metal G55 Co at Room Temperature], by Frank Hebner from Erlangen, Sep. 7, 2003, at the Friedrich-Alexander University, Erlangen-Nuremberg, Institut für Werkstoffwissenschaften, Lehrstuhl I—Allgemeine Werkstoffeigenschaften, Prof. Mughrabi, and the prior art cited in these documents.

For the process according to the invention, particular preference is given to the use, as the die core, of a hard metal which, based on its weight, consists of tungsten carbide to an extent of $\geq 90\%$ by weight. In addition, it is favorable in accordance with the invention when it additionally consists of Ni or of Ni and Cr to an extent of at least 5% by weight.

Even better for the process according to the invention is the use, as the die core, of a hard metal which, based on its weight, consists to an extent of from 90 to 95% by weight of tungsten carbide (WC), to an extent of from $\geq 0$ to 1% by weight of at least one metal carbide (generally active as a particle growth-inhibiting additive) from the group consisting of titanium carbide (TiC), tantalum carbide (TaC), niobium carbide (NbC), vanadium carbide (VC) chromium carbide ($Cr_3C_2$) and mixed metal carbides (e.g. tantalum niobium carbide (TaNbC)) which comprise at least two of the metals present in the aforementioned metal carbides, and also to an extent of from 5 to 10% by weight of Fe, Co, Ni and/or Cr, preference being given to Ni or Ni and Cr as the binder phase.

Very particular preference is given in the process according to the invention to using, as the hard metal for the die core, one which consists of 90 to 95% by wt. of WC,
$\geq 0$ to 1% by wt. of TiC and/or TaNbC, and
5 to 10% by wt. of Ni or Ni and Cr.

Among the aforementioned hard metals, preference is given in accordance with the invention in turn to those which consist of 89.2 to 94.8% by weight of WC,
0.2 to 0.8% by weight of TiC and TaNbC,
and 5 to 10% by weight of Ni.

These hard metals include the hard metal G 10-Ni from Hartmetall® Gesellschaft in D-70572 Stuttgart, which is usable particularly favorably in accordance with the invention for the die core.

All above remarks apply especially to hard metal particle sizes (i.e. hard substance particle sizes in the hard metal) of from 0.5 μm to 2 μm, preferably from 1 to 1.5 μm.

In addition, the statements made in this document regarding the material (or material composite) for the die apply especially when the pulverulent aggregate to be compacted in accordances with the invention is a pulverulent aggregate HW*. The latter is true not least when nitric acid is still present in the pulverulent aggregate HW* (in that case, it shall be referred to in this document as pulverulent aggregate HW**).

The mean roughness $R_a$ (to DIN 4768) of the inner wall of the die bore (especially in longitudinal section I and II) in the process according to the invention should preferably not be more than 0.2 μm and more preferably not more than 0.1 μm and even better not more than 0.05 μm.

Otherwise, the mean roughness $R_a$ of the molds in the process according to the invention should not be more than 1 μm, preferably not more than 0.8 μm and more preferably not more than 0.4 μm (the mean roughness is the arithmetic mean of the absolute magnitudes of the distances of the roughness profile from the center line within the measurement zone). Correspondingly low roughnesses should be achieved by polishing.

The production of a die to be used in accordance with the invention with, for example, a core composed of the hard metal G10-Ni and, for example, a die surround composed of DIN material 1.2379 is possible in a simple manner, for example, by so-called shrinkage. First, the die surround is produced from the tool steel. This is then heated, which expands it. The hard metal core can be inserted into the expanded die surround. In the course of cooling, the die surround contracts again and forms a virtually seamless composite with the hard metal core.

In order to take account of the problems described in WO 2005/115733, the center pins MF are advantageously manufactured from a DIN 1.2343 tool steel.

This is especially true in the case of compaction of pulverulent aggregates HW* and HW** (especially in the case of production of ringlike shaped precursor bodies F; in particular in the case of ringlike shaped precursor bodies $F^{LII}$). The die table tongue consists in the process according to the invention, especially in the case of pulverulent aggregate HW* or HW**, advantageously of the DIN spheroidal graphite gray cast iron GGG 50 with a thin applied layer of DIN tool steel 1.0425, while the die table brow and the die table chin, appropriately in application terms, are manufactured from DIN tool steel 1.6850 (nitrated). The lower shaft, the upper shaft and the accompanying shaft heads may, in the process according to the invention, just like the center pin holders, be manufactured in a manner known per se, for example, from DIN tool steel 1.25550 (annealed and tempered, Rockwell hardness HRC 58+2).

The pressures typically exerted by the two punches (or at least by the upper punch) in the performance of the process according to the invention at the end distance E are typically in the range from 50 to 5000 kg/cm$^2$, preferably from 200 to 3500 kg/cm$^2$, more preferably from 500 to 2500 kg/cm$^2$ and more preferably from 500 to 1500 kg/cm$^2$.

The preliminary pressures (which are exerted at the preliminary end distance $E^V$) are typically 5-500 kg/cm$^2$ and the main pressures are usually 1000-2000 kg/cm$^2$. The higher the main pressure employed, the more advantageous the process according to the invention is found to be.

The process according to the invention displays particular advantageousness when the pulverulent aggregate to be compacted comprises constituents which have corrosive action on steels, for example nitric acid, ammonium salts and/or nitrate salts.

The corrosive action results in these cases, when the process is practiced, in a comparatively rapid roughening of the inner wall of the die bore and hence an equally rapid increase in the sliding friction on removal of the shaped body formed in the case of an exclusively circular cylindrical die bore.

Especially in the case of an inventive production of ringlike shaped precursor bodies LII (e.g. $F^{LII}$), this problem is essentially completely remedied. The latter is especially true when the die is manufactured from a material composite as detailed above.

As already detailed at various points, the process according to the invention comprises the production of ringlike shaped precursor bodies from pulverulent aggregate which already comprises at least one metal oxide (which is generally solid under standard conditions (25° C., 1 atm)), and/or at least one such metal compound (e.g. a metal salt) which can be converted by thermal treatment at a temperature of ≧100° C. to a metal oxide (which is generally solid under standard conditions) (at least by thermal treatment in the presence of gaseous molecular oxygen and/or of components which release gaseous oxygen; in principle, the oxygen source may, for example, in the form of a peroxide, also be a constituent of the pulverulent aggregate and hence of the ringlike precursor body resulting in accordance with the invention). Such pulverulent aggregates shall also be referred to in this document as pulverulent aggregates O.

The solid metal oxide may be one which, as well as oxygen, comprises only one or else more than one (e.g. two or three) metal elements.

Useful metal (compounds in principle also include those which comprise only one, or else more than one (e.g. two or three) metal element.

In addition, the process according to the invention comprises the thermal treatment of the ringlike shaped precursor bodies produced in accordance with the invention. In the course of this thermal treatment, the ringlike oxidic shaped bodies desired in accordance with the invention are then formed. According to the invention, the thermal treatment is effected at temperatures of ≧100° C. frequently ≧150° C., or ≧200° C. (e.g. from 300 to 800° C.). Especially in the case of production of ringlike oxidic shaped support bodies, the thermal treatment may include one at temperatures of ≧600° C., or ≧1000° C. 1500° C. are not exceeded in most cases.

It is also essential to the invention that the pulverulent aggregate to be compacted in accordance with the invention, and with it the resulting ringlike shaped precursor bodies, comprise(s) substances (constituents) which decompose and/or are chemically converted under the conditions employed in the subsequent inventive thermal treatment to form compounds which are gaseous under the conditions of the thermal treatment (for example to form ammonia, steam, $CO_2$, CO and/or nitrogen oxides). In general, the weight loss accompanying the thermal treatment of the ringlike shaped precursor bodies and based on the starting weight thereof (owing to the aforementioned outgassing) is from 0.5 to 40% by weight, frequently from 0.8 to 35% by weight or from 2 to 30% by weight.

There is normally formation (release) of gaseous compounds in the course of an inventive thermal treatment of the ringlike shaped precursor bodies obtained in accordance with the invention, for example, when the constituents of the pulverulent aggregate to be compacted in accordance with the invention (of an aggregate O) are at least partly of organic nature, or comprise hydroxide ions, carbonate ions, hydrogencarbonate ions, ammonium ions, hydrogenphosphate ions and/or nitrate ions which generally decompose at least partly in the course of the inventive thermal treatment. The hydroxide ions, carbonate ions, hydrogencarbonate ions, ammonium ions, hydrogenphosphate ions and/or nitrate ions may in principle already be a constituent of the non-oxide metal compounds in the pulverulent aggregate to be compacted in accordance with the invention. However, they may also be added to the pulverulent aggregate to be compacted in accordance with the invention additionally (or only) as a constituent of substances which form pores and are not metal compounds in the subsequent thermal treatment of the ringlike shaped precursor bodies.

As such pore-forming substances, the pulverulent aggregate to be compacted in accordance with the invention (an aggregate O) may comprise, for example, added $NH_4OH$, $(NH_4)_2CO_3$, $NH_4HCO_3$, $NH_4NO_3$, urea, $NH_4CHO_2$, $NH_4CH_3CO_2$, $NH_4HSO_4$, $(NH_4)_2SO_4$, ammonium oxalate and/or hydrates of the aforementioned ammonium salts. It will be appreciated that the process according to the invention is also advantageous when the pulverulent aggregate to be compacted in accordance with the invention (an aggregate O) comprises, as organic substances which decompose in gaseous form and/or are converted chemically to gaseous compounds in the course of the subsequent thermal treatment, for example, added starches (such as potato starch, corn starch), ground nutshell, fine polymer granule (for example polyethylene, polypropylene), cellulose, graphite, stearic acid, malonic acid, salts of stearic acid, salts of malonic acid, among other compounds.

In addition, the pulverulent aggregate to be compacted in accordance with the invention (an aggregate O) may comprise, as further added assistants, lubricants which, for example, lower the adhesive friction between the ringlike shaped precursor body produced in accordance with the invention and the inner wall of the die bore. The lubricants of this type used may, for example, be graphite, carbon black, polyethylene glycol, stearic acid, salts of stearic acid, starch, polyacrylic acid, mineral oil, vegetable oil, water, boron nitride, boron trifluoride, glycerol, fine Teflon powder and/or cellulose ethers (it should be emphasized at this point that the process according to the invention is also notable in that it enables the minimization of the requirement for such assistants). The aforementioned lubricants may decompose and/or be converted chemically, if appropriate also with formation of gaseous substances, in the course of a thermal treatment of the ringlike shaped precursor bodies which follows the inventive shaping.

As further shaping assistants, the pulverulent aggregate to be compacted in accordance with the invention (an aggregate O) may comprise added so-called reinforcing agents which promote integrity in the resulting compact. Such reinforcing agents may, for example, be microfibers of glass, asbestos, silicon carbide and/or potassium titanate.

Based on the total amount of the pulverulent aggregate to be compacted in accordance with the invention (of an aggregate O), the total amount of shaping assistants will generally not be more than 30% by weight, usually not more than 20% by weight and in many cases not more than 10% by weight.

Typically, the pulverulent aggregate (an aggregate O) in the process according to the invention will be used dry to the touch. However, it may comprise up to 10% of its total weight of added substances which are liquid under standard conditions (25° C., 1 atm). However, the process according to the invention is also employable when the pulverulent aggregate (an aggregate O) comprises no such liquid substances at all. It will be appreciated that the pulverulent aggregate (a pulverulent aggregate O) may also comprise solid solvates (e.g. hydrates) which comprise such liquid substances in chemically and/or physically bound form. Such solvates decompose in the course of thermal treatment generally likewise with gaseous release of the solvate phase. Advantageously in accordance with the invention, the residual moisture content of the aggregate to be compacted in accordance with the invention is <10% by weight, and in the absence of water of crystallization (or crystal solvate phase) generally <5% by weight.

The particle diameters of the fine pulverulent aggregate to be compacted in accordance with the invention (of a pulverulent aggregate O) will (excluding added shaping and porosity agents), for at least 90% of the weight of the pulverulent aggregate (not including added shaping and porosity agents), appropriately in application terms, be in the range from 10 to 2000 µm, in many cases in the range from 20 to 1800 µm, or from 30 to 1700 µm, or from 40 to 1600 µm, or from 50 to 1500 µm. Particularly frequently, the aforementioned particle diameters will be in the range from 100 to 1500 µm or from 150 to 1500 µm.

In principle, an inventive thermal treatment of ringlike shaped precursor bodies produced in accordances with the invention can be effected either under reduced pressure, under inert atmosphere (e.g. $N_2$, noble gases, steam, $CO_2$ etc.), under a reducing atmosphere (e.g. $H_2$ or $NH_3$) or under an oxidizing atmosphere. In general, oxidizing atmospheres will comprise molecular oxygen. Typical oxidizing atmospheres are mixtures of inert gas ($N_2$, noble gases, steam, $CO_2$ etc.) and molecular oxygen. Typically, the content of molecular oxygen will be at least 0.1% by volume, frequently at least 0.2% by volume, in many cases at least 0.5% by volume, often at least 1% by volume, or at least 10% by volume, or at least 20% by volume. It will be appreciated that the content of molecular oxygen in such mixtures may also be 30% by volume, or 40% by volume, or 50% by volume, or more. It will be appreciated that another useful oxidizing atmosphere for such a thermal treatment is pure molecular oxygen. Frequently, an oxidizing thermal treatment will be effected under air. Generally, the thermal treatment can be effected under a stationary or under a flowing gas atmosphere (for example in an air stream).

The term "atmosphere (or gas atmosphere) in which the thermal treatment is effected" should be understood in this document such that it does not comprise gases which evolve from the ringlike shaped precursor bodies produced in accordance with the invention in the course of the thermal treatment owing to decomposition processes and/or chemical reaction processes. It will be appreciated that the gas atmosphere in which the thermal treatment is effected may also consist exclusively or partly of these gases. It is also possible for both the treatment temperature and the treatment atmosphere to be configured so as to be constant with time or variable with time over the duration of the thermal treatment. In the case that the desired result of the subsequent thermal treatment of ringlike shaped precursor bodies obtainable in accordance with the invention is ringlike (oxidic) unsupported catalysts whose active composition is at least one multimetal oxide, the thermal treatment is effected frequently at temperatures of from 150 to 650° C., in many cases from 200 to 600° C., often from 250 to 550° C. and in many cases from 300 to 500° C. In this document, the term "multimetal oxide" does not mean a simple mixture of different metal oxides, but rather a complex polyoxy compound which, as well as oxygen, comprises at least two different metals (metallic constituents).

As already addressed several times in this document, the process according to the invention is suitable especially for producing ringlike shaped precursor bodies from which, by thermal treatment, ringlike (oxidic) shaped catalyst bodies, or, expressed in simplified terms, ringlike catalysts are obtainable (for example when the catalytically active component of the ringlike shaped catalyst body is a multimetal oxide). Such ringlike shaped precursor bodies obtainable in accordance with the invention shall also be referred to in this document as ringlike shaped catalyst precursor bodies.

In this case, the ringlike shaped catalyst body in the simplest case may consist only of the catalytically active component (for example the multimetal oxide). It may also comprise the catalytically active component (for example the multimetal oxide) diluted with inert material. In both cases, reference is made to ringlike shaped unsupported catalyst bodies. When the active component is a multimetal oxide, reference will be made in this document to ringlike multimetal oxide unsupported catalysts.

Ringlike multimetal oxide unsupported catalysts are suitable especially for the heterogeneous catalysis of partial gas phase oxidations (cf., for example, DE-A 102005037678, German application 102007028332.8, German application 102007025869.2, German application 102007017080.9 and German application 102007003778.5) of organic compounds with molecular oxygen.

In this document, a full oxidation of an organic compound with molecular oxygen shall be understood to mean that the organic compound is converted under the reactive action of molecular oxygen such that all of the hydrogen present in the organic compound is converted to oxides of hydrogen. All different exothermic reactions of an organic compound under the reactive action of molecular oxygen are summarized here as partial oxidations of an organic compound (for example including ammoxidations and oxychlorinations, which are performed in the simultaneous presence of ammonia and hydrogen chloride respectively). In particular, in this document, partial oxidations shall be understood to mean those exothermic conversions of organic compounds under the reactive action of molecular oxygen in which the organic compound to be oxidized partially, after the reaction has ended, comprises at least one oxygen atom more in chemically bound form than before performance of the partial oxidation.

Examples of heterogeneously catalyzed partial gas phase oxidations given here by way of example include that of propylene to acrolein, that of isobutene to methacrolein, that of methacrolein to methacrylic acid and that of $C_4$ hydrocarbons to maleic anhydride. Typically, heterogeneously catalyzed partial gas phase oxidations are performed, for example, in tube bundle reactors cooled with salt melts. The catalysts are present, if appropriate diluted with inert shaped bodies, in the reaction tubes flowed through by the reaction gas mixture.

For the production of ringlike multimetal oxide unsupported catalysts, the procedure may be to use sources of the elemental constituents of the catalytically active multimetal oxide and shaping assistants for additional use if required (e.g. porosity agents, lubricants and reinforcing agents) to produce a finely divided aggregate, and to use this by the process according to the invention first to produce ringlike multimetal oxide shaped unsupported catalyst precursor bodies. The sources used for the elemental constituents of the multimetal oxide may be metal oxides (generally present in the solid state under standard conditions) and/or those metal compounds which can be converted by heating (thermal treatment) to oxides (which are generally in the solid state under standard conditions) (at least by thermal treatment in the presence of gaseous molecular oxygen and/or of components which release gaseous oxygen).

The ringlike multimetal oxide unsupported catalysts are then obtainable by subsequent thermal treatment of the ringlike multimetal oxide shaped unsupported catalyst precursor bodies (for example in the temperature range from 200 to 800° C., or from 300 to 600° C.).

The pulverulent aggregates for use for the inventive production of ringlike shaped multimetal oxide unsupported catalyst precursor bodies will therefore generally be aggregates HW* or aggregates HW**. More particularly, however, they will be pulverulent aggregates C. All statements made in this document with regard to the inventive compaction of pulverulent aggregates O, HW* and HW** therefore apply in a corresponding manner. Ringlike shaped multimetal oxide unsupported catalyst precursor bodies preferred in accordance with the invention are generally ringlike shaped bodies F, preferably ringlike shaped bodies $F^{LII}$.

Among other purposes, the process according to the invention is suitable for producing the shaped precursor bodies of those ringlike multimetal oxide unsupported catalysts which comprise, as the catalytically active component, at least one multimetal oxide in which the element Mo, or the element V, or the element P is that element other than oxygen which is numerically (calculated in molar terms) the most common (multimetal oxide means that the oxide comprises at least two elements other than oxygen).

More particularly, the process according to the invention is suitable for producing the shaped precursor bodies (especially ringlike shaped precursor bodies F or $F^{LII}$) of those ringlike multimetal oxide unsupported catalysts which comprise, as the catalytically active component, at least one multimetal oxide which comprises the elements Mo and Fe, or the elements Mo, Fe and Bi, or the elements Mo and V, or the elements Mo, V and P, or the elements V and P (in particular when the aforementioned commonness condition is simultaneously satisfied). The first ringlike multimetal oxide unsupported catalysts in the above list are suitable in particular for heterogeneously catalyzed partial gas phase oxidations of methanol to formaldehyde. The second are suitable in particular for the heterogeneously catalyzed partial gas phase oxidation of propylene to acrolein. The third are suitable in particular for heterogeneously catalyzed partial gas phase oxidations of acrolein to acrylic acid, the fourth are suitable in particular for the heterogeneously catalyzed partial gas phase oxidation of methacrolein to methacrylic acid, and the last in the above list are suitable in particular for heterogeneously catalyzed partial gas phase oxidations of n-butane to maleic anhydride.

For the inventive production of ringlike shaped multimetal oxide unsupported catalyst precursor bodies, preference is given to using a lower punch with a planar upper end face and an upper punch with a planar lower end face (the two end faces are preferably congruent to one another). It will be appreciated that ringlike shaped multimetal oxide unsupported (,catalyst precursor bodies can also, as described in this document, be produced with curved end faces.

Catalytically active multimetal oxides of the aforementioned type, including pulverulent aggregates usable for the inventive production of corresponding ringlike shaped multimetal oxide unsupported catalyst precursor bodies, can be found, inter alia, in the documents WO 2005/030393, EP-A 467 144, EP-A 1 060 792, DE-A 198 55 913, WO 01/68245, EP-A 1060792, Research Disclosure RD 2005-497012, DE-A 102005035978, DE-A 102005037678, WO 03/78059, WO 03/078310, DE-A 199 22 113, WO 02/24620, WO 02/062737, German application 102007028332.8, German application 102007025869.2, German application 102007017080.9 and US-A 2005/0131253.

The pulverulent (precursor) aggregates to be compacted in accordance with the invention are obtainable in the simplest manner by obtaining, from sources of the elemental constituents of the desired catalytically active multimetal oxide, a fine, very intimate, shapable mixture of a composition corresponding to the stoichiometry of the desired multimetal oxide, to which the shaping assistants (including reinforcing assistants) already mentioned may be added (and/or may be processed from the start).

Useful sources for the elemental constituents of the desired multimetal oxide are, as already stated, in principle those metal compounds which are already oxides and/or those metal compounds which can be converted to oxides by heating, at least in the presence of gaseous molecular oxygen and/or of components which release gaseous oxygen. In principle, the oxygen source may also, for example in the form of a peroxide, be a constituent of the precursor mixture (of the pulverulent aggregate) itself. The pulverulent (precursor) aggregate may also comprise added compounds such as $NH_4OH$, $(NH_4)_2CO_3$, $NH_4NO_3$, urea, $NH_4CHO_2$, $NH_4CH_3CO_2$, ammonium oxalate, hydrates of the aforementioned compounds and/or organic components, for example stearic acid, which can decompose and/or be decomposed in the course of thermal treatment as pore formers to give compounds which escape completely in gaseous form.

The preferably intimate mixing of the starting compounds (sources) to produce the fine pulverulent (precursor) aggregate shapable in accordance with the invention can be effected in dry form or in wet form. Where it is effected in dry form, the starting compounds are used appropriately in the form of fine powders (with a particle diameter $d_{50}$ (to determine particle diameter distributions and the particle diameters $d_{10}$, $d_{50}$ and $d_{90}$ (generally $d_x$) inferred therefrom, the particular fine powder was conducted via a dispersion channel into the Sympatec RODOS dry disperser (Sympatec GmbH, System-Partikel-Technik, Am Pulverhaus 1, D-38678 Clausthal-Zellerfeld) and dry-dispersed there with compressed air and blown into the measurement cell in a free jet. The Malvern Mastersizer S (Malvern Instruments, Worcestershire WR14 1AT, United Kingdom) is then used therein to determine the volume-based particle diameter distribution to ISO 13320. The particle diameters $d_x$ reported as the measurement result are defined such that X % of the total particle volume consists of particles with this diameter or a smaller diameter.) Appropriately in the range from 1 to 200 μm, preferably from 2 to 180 μm, more preferably from 3 to 170 μm and most preferably from 4 to 160 μm, or from 5 to 150 μm or from 10 to 150 μm, or from 15 to 150 μm). Addition of the shaping assistants can then be followed by the inventive shaping. Such assistants may, for example, be graphite as a lubricant, and also microfibers of glass, asbestos, silicon carbide and/or potassium titanate. Quite generally, one starting compound may be the source of more than one elemental constituent.

Instead of shaping the mixture obtained by mixing pulverulent sources as such directly to the desired precursor geometry, it is frequently appropriate, as a first shaping step, first to perform an intermediate compaction thereof, in order to coarsen the powder (generally to particle diameters $d_{50}$ of from 100 to 2000 μm, preferably from 150 to 1500 μm, more preferably from 400 to 1000 μm).

Even before the intermediate compaction, it is possible, for example, to add graphite as a compacting assistant. Subsequently, the inventive shaping is effected with the coarsened powder, prior to which it is possible if required once again to add, for example, finely divided graphite (and if appropriate further shaping assistants (including reinforcing agents)).

However, preference is given to effecting the intimate mixing of the sources in wet form. Typically, the starting compounds are mixed with one another, for example, in the form of an aqueous solution and/or suspension (though liquids such as isobutanol are also useful as solution and/or dispersion medium). Particularly intimate shapable mixtures are obtained when the starting materials are exclusively sources of the elemental constituents present in dissolved form. The solvent used is preferably water (though liquids such as isobutanol are also useful as solvents). Subsequently, the resulting solution or suspension is dried, the drying process being effected preferably by spray-drying with exit temperatures of from 100 to 150° C. (in some cases, the drying can also be effected by filtration and subsequent drying of the filtercake). The particle diameter $d_{50}$ of the resulting spray powder is typically from 10 to 50 μm. If water was the basis of the liquid medium, the resulting spray powder will normally comprise not more than 20% of its weight, preferably not more than 15% of its weight and more preferably not more than 10% of its weight of water. These percentages also apply generally in the case of use of other liquid solution or suspension assistants. After addition (or else without such an addition) of the desired shaping assistants to the particular dry mass in pulverulent form, the pulverulent mixture, as a fine precursor mixture (pulverulent aggregate), can be compacted (shaped) in accordance with the invention to the desired shaped multimetal oxide unsupported catalyst precursor bodies. The fine shaping assistants may, however, also already be added beforehand to the spray slurry (partly or completely).

Only partial removal of the solvent or suspension medium may also be appropriate when its additional use as a shaping assistant is intended.

Prior to an addition of, for example, fine graphite as a lubricant, a first thermal treatment of the dry powder can also already be effected. Addition of the, for example, graphite is then followed by the inventive shaping and the subsequent thermal further treatment.

Instead of shaping the fine precursor mixture based on the spray powder as such directly to the desired geometry, it is frequently appropriate first to carry out an intermediate compaction as the first shaping step, in order to coarsen the powder (generally to particle diameters of from 100 to 2000 μm, preferably from 150 to 1500 μm, more preferably from 400 to 1000 μm).

Even before the intermediate compaction, it is possible, for example, to add graphite as a compacting assistant. Subsequently, on the basis of the coarsened powder, the ultimate (actual), the inventive shaping is effected, prior to which fine graphite (and if appropriate further shaping assistants, for example reinforcing agents) can once again be added if required.

It will be appreciated that the sources of the elemental constituents used may also be starting compounds which have in turn been obtained by thermal treatment of precursor compounds (element sources), and are of multimetal oxide nature. More particularly, the starting compounds of the elemental constituents may be of multimetal nature.

All statements made so far in this document are valid in particular when the catalytically active multimetal oxide of the ringlike multimetal oxide unsupported catalyst has a stoichiometry of the general formula XII $$Mo_{12}Bi_aFe_bX^1_cX^2_dX^3_eX^4_fO_n \qquad (XII)$$

where
$X^1$=nickel and/or cobalt,
$X^2$=thallium, samarium, an alkali metal and/or an alkaline earth metal,
$X^3$=zinc, phosphorus, arsenic, boron, antimony, tin, cerium, lead, vanadium, chromium, niobium and/or tungsten,
$X^4$=silicon, aluminum, titanium and/or zirconium,
a=0.2 to 5,
b=0.01 to 5,
c=0 to 10,
d=0 to 2,
e=0 to 8,
f=0 to 10, and
n=a number which is determined by the valency and frequency of the elements in XII other than oxygen,
or a stoichiometry of the general formula XIII $$[Y^1_aY^2_bO_x]_p[Y^3_cY^4_dY^5_eY^6_fY^7_gY^8_hO_y]_q \qquad (XIII)$$

where
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony, $Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum or tungsten, or molybdenum and tungsten,
a'=0.01 to 8,
b'=0.1 to 30,
c'=0 to 4,
d'=0 to 20,
e'>0 to 20,
f'=0 to 6,
g'=0 to 15,
h'=8 to 16,
x', y'=numbers which are determined by the valency and frequency of the elements in XIII other than oxygen, and
p, q=numbers whose p/q ratio is from 0.1 to 10.

Such ringlike multimetal oxide unsupported catalysts are suitable in particular as catalysts with increased selectivity and activity for the gas phase catalytic partial oxidation of propene to acrolein and of isobutene or tert-butanol or the methyl ether thereof to methacrolein.

For the inventive production of the corresponding ringlike shaped multimetal oxide unsupported catalyst precursor bodies, sources of the elemental constituents of the active multimetal oxide will be used to obtain a fine precursor mixture shapable by compaction (a pulverulent aggregate), and this mixture, after addition of shaping assistants (on this subject, see, for example, DE-A 10 2005 037 678, DE-A 10 2007 003 778, DE-A 10 2007 028 332 and the prior art cited in these documents) which may also comprise reinforcing agents, will be compacted in the inventive manner (preferably to ringlike shaped unsupported catalyst precursor bodies F or $F^{LII}$).

The inventive shaping is advantageously effected such that the side crushing strength of the resulting ringlike shaped multimetal oxide unsupported catalyst precursor body is ≧10 and ≦40 N, better ≧10 and ≦35 N, even better ≧12 N and ≦30 N. The side crushing strength of the ringlike shaped multimetal oxide unsupported catalyst precursor bodies is preferably ≧13 N and ≦27 N, or ≧14 N and ≦25 N. Most preferably, the side crushing strength of the ringlike shaped multimetal oxide unsupported catalyst precursor bodies is ≧15 N and ≦22 N.

The granularity (the particle diameter) of the pulverulent aggregate to be compacted in accordance with the invention (excluding the assistants to be added) is advantageously adjusted to from 200 to 1500 μm, particularly advantageously to from 400 to 1000 μm (for example by intermediate compaction). In a favorable manner, at least 80% by weight, better at least 90% by weight and particularly advantageously 95 or 98 or more % by weight of the pulverulent aggregate are within this granularity range.

In this document, the side crushing strength is understood to mean the compressive strength when the ringlike shaped multimetal oxide unsupported catalyst precursor body is compressed at right angles to the axis of symmetry (i.e., parallel to the surface of the orifice). All side crushing strengths in this document relate to a determination by means of a Z 2.5/TS15 materials testing machine from Zwick GmbH & Co (D-89079 Ulm). This materials testing machine is designed for quasistatic stress having a single-impetus, stationary, dynamic or varying profile. It is suitable for tensile, compressive and bending tests. The installed KAF-TC force transducer from A.S.T. (D-01307 Dresden) with the manufacturer number 03-2038 is calibrated in accordance with DIN EN ISO 7500-1 and is usable for the 1-500 N measurement range (relative measurement uncertainty: ±0.2%).

The measurements are carried out with the following parameters:
Initial force: 0.5 N.
Rate of initial force: 10 mm/min.
Testing rate: 1.6 mm/min.

The upper punch is initially lowered slowly down to just above the outer face of the ringlike shaped unsupported catalyst precursor body. The upper punch is then stopped, in order subsequently to be lowered at a significantly slower testing rate with the minimum initial force required for further lowering.

The initial force at which the shaped unsupported catalyst precursor body exhibits crack formation is the side crushing strength (SCS).

Regarding the active compositions of the stoichiometry XII, the stoichiometric coefficient b is preferably From 2 to 4, the stoichiometric coefficient c is preferably from 3 to 10, the stoichiometric coefficient d is preferably from 0.02 to 2, the stoichiometric coefficient e is preferably from 0 to 5 and the stoichiometric coefficient a is preferably from 0.4 to 2. The stoichiometric coefficient f is advantageously from 0.5 or 1 to 10. More preferably, the aforementioned stoichiometric coefficients are simultaneously within the preferred ranges specified.

In addition, $X^1$ is preferably cobalt, $X^2$ is preferably K, Cs and/or Sr, more preferably K, $X^3$ is preferably tungsten, zinc and/or phosphorus, and $X^4$ is preferably Si. More preferably, the variables $X^1$ to $X^4$ simultaneously have the aforementioned definitions.

More preferably, all stoichiometric coefficients a to f and all variables $X^1$ to $X^4$ simultaneously have their aforementioned advantageous definitions.

Within the stoichiometries of the general formula XIII, preference is given to those which correspond to the general formula XIV $$[Bi_{a''}Z^2_{b''}O_{x''}]_{p''}[Z^8_{12}Z^3_{c''}Z^4_{d''}Fe_{e''}Z^5_{f''}Z^6_{g''}Z^7_{h''}O_{y''}]_{q''} \quad (XIV)$$

where
$Z^2$=molybdenum or tungsten, or molybdenum and tungsten,
$Z^3$=nickel and/or cobalt,
$Z^4$=thallium, an alkali metal and/or an alkaline earth metal, preferably K, Cs and/or Sr,
$Z^5$=phosphorus, arsenic, boron, antimony, tin, cerium, vanadium, chromium and/or Bi,
$Z^6$=silicon, aluminum, titanium and/or zirconium, preferably Si,
$Z^7$=copper, silver and/or gold,
$Z^8$=molybdenum or tungsten, or molybdenum and tungsten,
a''=0.1 to 1,
b''=0.2 to 2,
c''=3 to 10,
d''=0.02 to 2,
e''=0.01 to 5, preferably 0.1 to 3,
f''=0 to 5,
g''=0 to 10, preferably >0 to 10, more preferably 0.2 to 10 and most preferably 0.4 to 3,
h''=0 to 1,
x'', y''=numbers which are determined by the valency and frequency of the elements in XIV other than oxygen, and
p'', q''=numbers whose p''/q'' ratio is from 0.1 to 5, preferably 0.5 to 2.

Additionally preferred are catalytically active multimetal oxides of stoichiometry XIII which comprise three-dimensional regions of the chemical composition $Y^1_a Y^2_b O_{x'}$ which are delimited from their local environment as a consequence of their different composition than their local environment and whose longest diameter (longest direct line passing through the center of the region and connecting two points on the surface (interface) of the region) is from 1 nm to 100 µm, frequently from 10 nm to 500 nm or from 1 µm to 50 or 25 µm.

Particularly advantageous catalytically active multimetal oxides of stoichiometry XIII are those in which $Y^1$ is only bismuth.

Within the catalytically active multimetal oxides of stoichiometry XIV, preference is given in accordance with the invention to those in which $Z^2{}_{b''}$=(tungsten)$_{b''}$ and $Z^8{}_{12}$=(molybdenum)$_{12}$.

Additionally preferred are catalytically active multimetal oxides of stoichiometry XIV which comprise three-dimensional regions of chemical composition $Bi_{a''}Z^2{}_{b''}O_{x''}$ which are delimited from their local environment as a consequence of their different composition than their local environment and whose longest diameter (longest direct line passing through the center of the region and connecting two points on the surface (interface) of the region) is from 1 nm to 100 µm, frequently from 10 nm to 500 nm or from 1 µm to 50 or 25 µm.

It is additionally advantageous when at least 25 mol % (preferably at least 50 mol % and more preferably 100 mol %) of the total $[Y^1{}_aY^2{}_bO_x]_p$ ($[Bi_{a''}Z^2{}_{b''}O_{x''}]_p$) content of the catalytically active multimetal oxides of stoichiometry XIII (of stoichiometry XIV) obtainable as described in the catalytically active multimetal oxides of stoichiometry XIII (of stoichiometry XIV) is in the form of three-dimensional regions of chemical composition $Y^1{}_aY^2{}_bO_{x'}$ ($[Bi_{a''}Z^2{}_{b''}O_{x''}]$) which are delimited from their local environment as a consequence of their different chemical composition than their local environment and whose longest diameter is in the range from 1 nm to 100 µm.

In the case of a catalytically active multimetal oxide of one of the stoichiometries XII to XIV, useful lubricants for the process according to the invention for producing ringlike shaped precursor bodies, in addition to graphite, are also carbon black, polyethylene glycol, stearic acid, starch, polyacrylic acid, mineral oil or vegetable oil, water, boron trifluoride and/or boron nitride. Glycerol and cellulose ethers can also be used as further lubricants. Preference is given in accordance with the invention to adding graphite as the sole shaping assistant. Based on the composition to be shaped in accordance with the invention to the ringlike shaped unsupported catalyst precursor body, a total of generally ≦15% by weight, usually ≦9% by weight, in many cases ≦5% by weight, often ≦4% by weight of graphite is added. Typically, the aforementioned added amount is ≧0.5% by weight, usually ≧2.5% by weight. Graphites added with preference are Asbury 3160 and Asbury 4012 from Asbury Graphite Mills, Inc. New Jersey 08802, USA and Timrex® T44 from Timcal Ltd., 6743 Bodio, Switzerland.

If required, fine reinforcing agents, such as microfibers of glass, asbestos, silicon carbide or potassium titanate, can be added.

The thermal treatment of ringlike shaped multimetal oxide unsupported catalyst precursor bodies obtainable in accordance with the invention as just described is effected generally at temperatures which exceed 350° C. Normally, in the context of the thermal treatment, the temperature of 650° C. is, however, not exceeded. Advantageously in accordance with the invention, in the context of the thermal treatment, the temperature of 600° C., preferably the temperature of 550° C. and more preferably the temperature of 510° C. is not exceeded. Moreover, in the context of the thermal treatment of the ringlike shaped unsupported catalyst precursor body, preferably the temperature of 380° C., advantageously the temperature of 400° C., particularly advantageously the temperature of 420° C. and most preferably the temperature of 440° C. is exceeded. The thermal treatment may also be divided into several sections over its duration. For example, a thermal treatment can be carried out first at a temperature of 150 to 350° C., preferably from 220 to 290° C., followed by a thermal treatment at a temperature of from 400 to 600° C., preferably from 430 to 550° C.

Normally, the thermal treatment of the ringlike shaped multimetal oxide (XII to XIV) unsupported catalyst precursor body takes several hours (usually more than 5 hours). Frequently, the total duration of the thermal treatment extends to more than 10 h. Usually, in the context of the thermal treatment of the ringlike shaped unsupported catalyst precursor body, treatment times of 45 h or 25 h are not exceeded. The total treatment time is often below 20 h. Advantageously in accordance with the invention, in the context of the thermal treatment of the relevant ringlike shaped unsupported catalyst precursor body, 500° C. (460° C.) are not exceeded, and the treatment time in the temperature window of ≧400° C. (≧440° C.) extends to from 5 to 20 h.

The thermal treatment (and also the decomposition phase addressed below) of the ringlike shaped multimetal oxide (XII to XIV) unsupported catalyst precursor bodies detailed above can be effected either under inert gas or under an oxidative atmosphere, for example air (mixture of inert gas and oxygen), or else under a reducing atmosphere (for example mixture of inert gas, $NH_3$, CO and/or $H_2$, or methane, acrolein, methacrolein). Of course, the thermal treatment can also be performed under reduced pressure.

In principle, the thermal treatment of ringlike shaped multimetal oxide unsupported catalyst precursor bodies can be carried out in a wide variety of different furnace types, for example heatable forced-air chambers, tray furnaces, rotary tube furnaces, belt calciners or shaft furnaces. Preference is given to effecting the thermal treatment of the ringlike shaped multi metal oxide unsupported catalyst precursor bodies in a belt calcining apparatus, as recommended by DE-A 100 46 957 and WO 02/24620.

The thermal treatment of ringlike shaped multimetal oxide unsupported catalyst precursor bodies below 350° C. generally pursues the aim of thermal decomposition of the sources of the elemental constituents of the desired ringlike multimetal oxide unsupported catalyst which are present in the shaped unsupported catalyst precursor bodies. Frequently, this decomposition phase is effected in the course of heating to temperatures of ≧350° C.

Especially for the production of catalytically active multimetal oxides of the stoichiometry of the general formula XIII or XIV, it is advantageous to preform a mixed oxide $Y^1{}_aY^2{}_bO_{x'}$ or $Bi_{a''}Z^2{}_{b''}O_{x''}$ as a source of the elements $Y^1$, $Y^2$ or Bi, $Z^2$ in the absence of the remaining constituents of the multimetal oxide and to use it to obtain, after its preformation, as already described, with sources of the remaining constituents of the multimetal oxide, a fine shapable mixture, in order to shape the ringlike shaped multimetal oxide unsupported catalyst precursor body therefrom in accordance with the invention after addition of shaping assistants.

In such a procedure, it should be ensured merely that, in the case that the production of the fine shapable mixture is effected in wet form (in suspension), the preformed mixed oxides $Y^1{}_aY^2{}_bO_{x'}$ or $Bi_{a''}Z^2{}_{b''}O_{x''}$ do not go into solution to a significant degree.

A procedure is described above is described in detail in documents DE-A 44 07 020, EP-A 835, EP-A 575 897 and DE-C 33 38 380, and German application 102007003778.5.

For example, water-soluble salts of $Y^1$ such as nitrates, carbonates, hydroxides or acetates can be mixed with $Y^2$ acids or ammonium salts thereof in water, the mixture can be dried (preferably spray-dried) and the dried composition can then be treated thermally. The thermally treated composition is subsequently appropriately comminuted (for example in a ball mill or by jet milling) and, from the powder which is obtainable in this way and generally consists of essentially spherical particles, the particle class with a greatest particle diameter within the greatest diameter range desired for the active multimetal oxide of the stoichiometry of the general formula XII or XIV is removed by classifying to be performed in a manner known per se (for example wet or dry screening) and is preferably mixed with, based on the mass of this removed particle class, from 0.1 to 3% by weight of fine $SiO_2$ (the particle diameter $d_{50}$ of the typically essentially spherical $SiO_2$ particles is appropriately from 100 nm to 15 μm), so as to produce a starting composition 1. The thermal treatment is effected appropriately at temperatures of from 400 to 900° C., preferably at from 600 to 900° C. The latter is especially true when the preformed mixed oxide is one of the stoichiometry $BiZ^2O_6$, $Bi_2Z^2{}_2O_9$ and/or $Bi_2Z^2{}_3O_{12}$, among which $Bi_2Z^2{}_2O_9$ is preferred, especially when $Z^2$=tungsten.

Typically, the thermal treatment is effected in an air stream (for example in a rotary tube furnace as described in DE-A 103 25 487). The duration of the thermal treatment extends generally to a few hours.

The remaining constituents of the desired active multimetal oxide of the general formula XIII or XIV are normally used, proceeding from sources suitable in a manner known per se (cf. EP-A 835 and DE-C 33 38 380, and also DE-A 44 07 020 and German application 102007003778.5), in a manner appropriate in accordance with the invention, to produce, for example, a very intimate, preferably fine dry mixture (for example combine water-soluble salts such as halides, nitrates, acetates, carbonates or hydroxides in an aqueous solution and then, for example, spray-dry the aqueous solution or suspend water-insoluble salts, for example oxides, in aqueous medium and then, for example, spray-dry the suspension), which is referred to here as starting composition 2. It is essential only that the constituents of the starting composition 2 are either already oxides or are those compounds which can be converted to oxides by heating, if appropriate in the presence of oxygen and/or oxygen sources. Subsequently, starting composition 1 and starting composition 2 are mixed in the desired quantitative ratio and with addition of shaping assistants to give the mixture shapable to the ringlike shaped unsupported catalyst precursor body. The shaping can, as already described, appropriately in application terms, be effected v a the stage of an intermediate compaction.

In a less preferred embodiment, the preformed mixed oxide $Y^1{}_{a'}Y^2{}_{b'}O_{x'}$ or $Bi_{a''}Z^2{}_{b''}O_{x''}$ can also be mixed intimately in liquid, preferably aqueous medium with sources of the remaining constituents of the desired active composition. This mixture is subsequently dried, for example, to give an intimate dry mixture and then, as already described, shaped and treated thermally. The sources of the remaining constituents may be present dissolved and/or suspended in this liquid medium, whereas the preformed mixed oxide should be essentially insoluble in this liquid medium, i.e. has to be present in suspended form.

The preformed mixed oxide particles are present essentially unchanged in the finished annular unsupported catalyst in the longest dimension established by the classification. Otherwise, the procedure may be as described in German application 102007003778.5. The statements made in German application 102007003778.5 with regard to annular shaped multimetal oxide unsupported catalyst precursor bodies and the annular multimetal oxide unsupported catalysts resulting therefrom apply correspondingly to the subject matter of this application.

Typically, the side crushing strengths of ringlike multimetal oxide (XII to XIV) unsupported catalysts obtainable as described are from 5 to 13 N, frequently from 8 to 11 N.

As already mentioned, the ringlike unsupported catalysts obtainable as described are suitable especially as catalysts for the partial oxidation of propene to acrolein or of isobutene and/or tert-butanol to methacrolein. The partial oxidation can, for example, be carried out as described in documents WO 00/53557, WO 00/53558, DE-A 199 10 506, EP-A 1 106 598, WO 01/36364, DE-A 199 27 624, DE-A 199 48 248, DE-A 199 48 523, DE-A 199 48 241, EP-A 700 714, DE-A 10313213, DE-A 103 13 209, DE-A 102 32 748, DE-A 103 13 208, WO 03/039744, EP-A 279 374, DE-A 33 38 380, DE-A 33 00 044, EP-A 575 897, DE-A 10 2004 003 212, DE-A 10 2005 013 039, DE-A 10 2005 009 891, German application 102007003778.5, DE-A 10 2005 010 111, DE-A 10 2005 009 885 and DE-A 44 07 020 for annular unsupported catalysts, and the catalyst charge may comprise, for example, only ringlike unsupported catalysts obtainable as described or ringlike unsupported catalysts diluted, for example, with inert shaped bodies. In the latter case, the catalyst charge is advantageously generally configured such that its volume-specific activity increases continuously, abruptly and/or in stages in flow direction of the reaction gas mixture.

Multimetal oxide stoichiometries particularly advantageous for the process of propylene partial oxidation to acrolein are:

a) $[Bi_2W_2O_9 \times 2WO_3]_{0.4}[Mo_{12}Co_{5.5}Fe_{2.94}Si_{1.59}K_{0.08}O_x]_1$;
b) $Mo_{12}Ni_{6.5}Zn_2Fe_2Bi_1P_{0.0065}K_{0.06}O_x \cdot 10SiO_2$;
c) $Mo_{12}Co_7Fe_{2.94}Bi_{0.6}Si_{1.59}K_{0.08}O_x$;
d) such as multimetal oxide II unsupported catalyst according to example 1 of DE-A 197 46 210; and
e) such as example 1c from EP-A 015 565.

However, the statements in this document are also valid when the catalytically active multimetal oxide of the ringlike multimetal oxide unsupported catalyst has a stoichiometry of the general formula XV $$Mo_{12}P_aV_bX_c^1X_d^2X_e^3Sb_fRe_gS_hO_n \qquad (XV)$$

where:
$X^1$=potassium, rubidium and/or cesium,
$X^2$=copper and/or silver,
$X^3$=cerium, boron, zirconium, manganese and/or bismuth,
a=0.5 to 3,
b=0.01 to 3,
c=0.2 to 3,
d=0.01 to 2,
e=0 to 2,
f=0 to 2, preferably 0.01 to 2,
g=0 to 1,
h=0 to 0.5, preferably 0.001 to 0.5, and
n=a number which is determined by the valency and frequency of the elements in XV other than oxygen.

Preference is given to multimetal oxides XV in which h is from 0.03 to 0.5.

Particularly preferred stoichiometries of the general formula XV are those of working examples B1 to B15 from EP-A 467 144, even when these illustrative multimetal oxides do not comprise any K and/or any Re.

The aforementioned EP-A 467 144, and German application 102007003778.5 also describe the Production of annular shaped multimetal oxide (XV) unsupported catalyst bodies and the use thereof as catalysts for the heterogeneously catalyzed gas phase partial oxidation of methacrolein to methacrylic acid. These descriptions are also relevant in the context given in the present application.

In other words, ringlike shaped multimetal oxide (XV) unsupported catalyst precursor bodies can be produced in accordance with the invention by finely distributing salts, suitable as starting compounds, of the elemental constituents which constitute them, if appropriate at elevated temperature and with addition of acids or bases, in aqueous medium by dissolution and/or suspension and, to prevent undesired oxidation processes if appropriate under inert gas, mixing them, drying the mixture (for example concentrating by evaporation or spray-drying), adding, for example, graphite as a lubricant and if appropriate other shaping assistants among those already mentioned to the resulting dry composition which is in finely divided form or has been converted to finely divided form, and shaping (compacting) the resulting fine composition in accordance with the invention to give the desired ringlike geometry. The resulting shaped catalyst precursor bodies are subsequently treated thermally for conversion to the active ringlike shaped catalyst bodies. Preference is given to performing the thermal treatment at temperatures of from 180 to 480° C., particular preference to performing it at temperatures of from 250 to 450° C. The thermal treatment can be effected under the gas atmospheres already described. Mention shall be made once again by way of example of flowing air, flowing inert gas atmosphere (e.g. $N_2$, or $CO_2$, or noble gases) or reduced pressure. The thermal treatment can be carried out in several temperature stages and/or in different atmospheres. For example, thermal treatment can be effected, for example, in a first stage at from 200 to 260° C. in air, in a second stage at from 420 to 460° C. in nitrogen and in a third stage at from 350 to 410° C. again in air. In general, flowing air is the preferred atmosphere for the thermal treatment.

Otherwise, the statements made in this document for the production of ringlike shaped unsupported catalyst bodies of multimetal oxides XII to XIV apply here correspondingly, but with the difference that the increased side crushing strengths for the annular shaped unsupported catalyst precursor bodies are preferred here.

Equally, the statements made in German application 102007003778.5 with regard to the production of annular shaped unsupported catalyst bodies of multimetal oxides XV apply here correspondingly.

In other words, for example, the preferred drying process for the aqueous solution or suspension of the sources of the elemental constituents of the desired active multimetal oxide XV is spray-drying. The resulting spray powder with a particle diameter $d_{50}$ between 10 and 50 μm is advantageously intermediately compacted after addition of fine graphite as an assistant in order to coarsen the powder. The intermediate compaction here is preferably effected to particle diameters of from 100 to 2000 μm, preferably from 150 to 1500 μm and more preferably from 400 to 1000 μm. Subsequently, the inventive shaping is effected on the basis of the coarsened powder, prior to which fine graphite (and if appropriate further shaping assistants) may be added once again if required.

In the described method of producing ringlike shaped unsupported catalyst bodies of active multimetal oxides of the general formula XV, antimony is used typically in the form of antimony trioxide, rhenium, for example, in the form of rhenium(VII) oxide, molybdenum preferably in the form of the ammonium salt of molybdic acid or of phosphomolydic acid, boron, for example, in the form of boric acid, vanadium generally in the form of ammonium vanadate or vanadium oxalate, phosphorus advantageously in the form of orthophosphoric acid or diammonium phosphate, sulfur, for example, in the form of ammonium sulfate, and the cationic metals normally in the form of nitrates, oxides, hydroxides, carbonates, chlorides, formates, oxalates, and/or acetates, or the hydrates thereof.

The process according to the invention is also suitable for producing ringlike shaped multimetal oxide unsupported catalyst precursor bodies with curved and/or uncurved end face from ringlike multimetal oxide unsupported catalysts whose active multimetal oxide is a multimetal oxide comprising vanadium, phosphorus and oxygen, and which are suitable as catalysts for the heterogeneously catalyzed gas phase oxidation of at least one hydrocarbon having at least four carbon atoms, especially n-butane, n-butenes and/or benzene) to maleic anhydride. The stoichiometry of the active multimetal oxide may, for example, be one of the general formula XVI

$$V_1P_bFe_cX^1_dX^2_eO_n \quad (XVI)$$

where:
$X^1$=Mo, Bi, Co, Ni, Si, Zn, Hf, Zr, Ti, Cr, Mn, Cu, B, Sn and/or Nb,
$X^2$=K, Na, Rb, Cs and/or Tl,
b=0.9 to 1.5,
c=0 to 0.1,
d=0 to 0.1,
e=0 to 0.1, and
n=a number which is determined by the valency and frequency of the elements in XVI other than oxygen.

For the production of pulverulent aggregates which are suitable in this regard and are to be compacted in accordance with the invention to ringlike shaped precursor bodies (especially F or $F^{LII}$), reference is made at this point to WO 03/078310 and German application 102007003778.5, WO 01/68245 and DE-A 10 2005 035 978, which relate to the production of corresponding annular systems.

For example, the procedure may be as follows:
a) reacting a pentavalent vanadium compound (e.g. $V_2O_5$) with an organic, reducing solvent (e.g. isobutanol) in the presence of a pentavalent phosphorus compound (e.g. ortho- and/or pyrophosphoric acid) with heating to from 75 to 205° C., preferably to from 100 to 120° C.;
b) cooling the reaction mixture to advantageously from 40 to 90° C.;
c) adding iron(III) phosphate;
d) heating again to from 75 to 205° C., preferably from 100 to 120° C.;
e) isolating the solid precursor composition formed, which comprises vanadium, phosphorus, iron and oxygen (for example by filtering);
f) drying and/or thermally pretreating the precursor composition (if appropriate until commencement of preformation by elimination of water from the precursor composition);
g) adding fine graphite and subsequently shaping in accordance with the invention to give the ringlike shaped multimetal oxide unsupported catalyst precursor body;
followed by thermal treatment of the shaped catalyst precursor bodies formed by heating in an atmosphere which comprises oxygen, nitrogen, noble gases, carbon dioxide, carbon monoxide and/or steam (for example as described in WO 03078310 at page 20 line 16 to page 21 line 85).

The process according to the invention further comprises processes for producing ringlike shaped multimetal oxide unsupported catalyst precursor bodies with curved and/or uncurved end face from ringlike multimetal oxide unsupported catalysts whose active multimetal oxide is a multimetal oxide comprising Mo, V and at least one of the elements Te and Sb, as described, for example, by documents EP-A 962

253, DE-A 101 22 027, EP-A 608 838, DE-A 198 35 247, EP-A 895 809, EP-A 1 254 709, EP-A1 192 987, EP-A 1 262 235, EP-A 1 193240, JP-A 11-343261, JP-A 11-343262, EP-A 1 090 684, EP-A 1 301 457, EP-A 1 254 707, EP-A 1 335 793, DE-A 100 46 672, DE-A 100 34 825, EP-A 1 556 337, DE-A 100 33 121, WO 01/98246 and EP-A 1 558 569.

Frequently, the aforementioned multimetal oxides comprising Mo, V and at least one of the elements Te and Sb also comprise the element Nb. The aforementioned resulting ringlike multimetal oxide unsupported catalysts are suitable for all heterogeneously catalyzed gas phase reactions (especially partial oxidations) detailed in the aforementioned documents. These are in particular the heterogeneously catalyzed partial gas phase oxidation of propane to acrylic acid, and of acrolein to acrylic acid, of methacrolein to methacrylic acid and of isobutane to methacrylic acid.

However, the process according to the invention is also suitable, as already addressed several times in this document, for producing ringlike shaped precursor bodies (for example ringlike shaped precursor bodies F or ringlike shaped precursor bodies $F^{LII}$), from which ringlike (oxidic) shaped support bodies are obtainable by thermal treatment, which can be used, for example, to produce ringlike coated catalysts or to produce ringlike impregnated catalysts. Such ringlike shaped support bodies can of course also be used as inert shaped bodies to dilute a fixed catalyst bed.

For the inventive production of such ringlike shaped support precursor bodies, the pulverulent aggregate to be compacted in accordance with the invention which is used is generally one which consists of metal oxides (which are typically solids under standard conditions) and/or of those metal compounds (e.g. salts) which can be converted by heating (thermal treatment) to oxides (which are typically solid under standard conditions) (at least by thermal treatment in the presence of gaseous molecular oxygen and/or of components which release gaseous oxygen). In addition, the pulverulent aggregate may comprise additions of the shaping assistants already mentioned in this document, for example lubricants, porosity agents and reinforcing agents.

The pulverulent aggregates for use for the inventive production of ringlike shaped support precursor bodies will therefore likewise generally be aggregates HW* or aggregates HW**. More particularly, they will, however, be pulverulent aggregates O. All statements made in this document with regard to the inventive compaction of pulverulent aggregates O, HW* and HW** therefore apply correspondingly. Ringlike shaped support precursor bodies preferred in accordance with the invention are generally ringlike shaped precursor bodies F, preferably ringlike shaped precursor bodies $F^{LII}$.

The thermal treatment of the ringlike shaped support precursor bodies to convert them to the ringlike support is effected generally at temperatures of $\geq 500°$ C., frequently $\geq 600°$ C. and in many cases $\geq 700°$ C. In general, the aforementioned thermal treatment is, however, performed at temperatures of $\leq 1500°$ C. The thermal treatment can be effected either under inert gas or under an oxidative atmosphere, for example air (mixture of inert gas and oxygen). Of course, the thermal treatment can also be effected under reduced pressure or a reducing atmosphere.

Typically, the thermal treatment is effected under an oxidizing atmosphere (generally under air).

The support oxides normally differ from the catalytically active multimetal oxides in that the thermal treatment to obtain them is effected at significantly higher temperatures and/or over a longer period (as a result of which they are frequently substantially nonporous) and/or that the numerically (calculated in molar terms) most common element therein other than oxygen is not a transition metal of transition group 5 to 11 (that is the vanadium group, the chromium group, the manganese group, the iron group, the cobalt group and the nickel group) and is not phosphorus. In many cases, the numerically (calculated in molar terms) most common metal present therein other than oxygen is an element from the group consisting of alkaline earth metal (e.g. Mg, Ca), Zn, Zr, Al, Si and Ti.

The organic (including graphite) shaping assistants used additionally in the production of the ringlike shaped support precursor bodies decompose in the course of the aforementioned thermal treatment generally to compounds which escape in gaseous form (and/or are converted to chemical compounds which escape in gaseous form). Frequently, the ringlike shaped support body consists of a ceramic material. Examples include silicate ceramics and other metal oxide ceramics. In the corresponding manner, the pulverulent aggregate which is to be compacted in accordance with the invention to produce a ringlike shaped support precursor body comprises, as mineral starting raw materials, in many cases pulverulent silicates, for example zirconium silicate, aluminum silicate (e.g. mullite), magnesium silicate (e.g. steatite) and other pulverulent metal oxides, for example aluminum oxide, magnesium oxide and zirconium oxide.

Further details will be given at this point by way of example of the production of the shaped support bodies designed in ring form in WO 99/48606, which are suitable for production of supported catalysts for the conversion of ethylene and hydrogen chloride in the presence of molecular oxygen to 1,2-dichloroethane ("oxychlorination").

The fine mineral raw material used is a fine mixture of pseudoboehmite and y-$Al_2O_3$ in a weight ratio of from 4:1 to 1:4, preferably from 1:1 to 1:3. To this mixture, whose $d_{50}$ particle diameter is, appropriately in application terms, from 10 to 100 µm, are added, based on its weight, from 0.5 to 7% by weight, (preferably from 2 to 5% by weight) of magnesium stearate and from 0.5 to 3% by weight (preferably from 1 to 1.5% by weight) of fine graphite ($d_{50}$ particle diameter from 15 to 30 µm) as shaping assistants.

The resulting pulverulent aggregate is subsequently compacted in the inventive manner to the ringlike shaped support precursor bodies (following the teaching of EP-A 184790, the upper end face of the lower punch and the lower end face of the upper punch advantageously have a concave configuration (i.e. they preferably have a circular channel)). These shaped bodies are then treated thermally in an oxidizing atmosphere (preferably under air) at temperatures of from 500 to 800° C., preferably from 700 to 750° C. (generally from 0.5 to 10 h).

The ringlike shaped support body thus obtained is subsequently impregnated with an aqueous $CuCl_2$/KCl solution. After the impregnation, the ringlike shaped bodies are dried to give the active ringlike catalysts (generally at temperatures of from 80 to 300° C., preferably from 100 to 200° C.). The drying is effected normally under air.

Typical drying times are from 0.2 to 10 h, and in the range of elevated temperatures from 0.5 to 2 h. The concentration and the volume of the impregnation solution in the impregnation are, appropriately in application terms, selected such that the resulting supported catalysts have a Cu content of from 1 to 15% by weight, preferably from 2 to 10% by weight, and a K content of from 0.1 to 8% by weight, preferably from 0.3 to 3% by weight. Otherwise, the procedure may be as described in WO 99/48606.

However, the statements made in this document are also valid when the catalytically active multimetal oxide of the ringlike multimetal oxide unsupported catalyst has the stoichiometry $(Fe_2O_3)_1 \cdot (MoO_3)_{5.25}$. Suitable starting compounds used to produce it are, for example, iron(III) nitrate and molybdenum trioxide. The particularly preferred Fe source is iron(III) nitrate nonahydrate melt according to the teaching of PCT/EP2008/050341. Preference is given to mixing the two with one another in aqueous ammoniacal solution. This is subsequently spray-dried and the resulting spray powder is compacted in the inventive mariner to give ringlike shaped precursor bodies. The end distance E is preferably 5 mm, the length of the outline of the circular cylinder Z is preferably $2 \cdot \pi$ mm ($\pi$ is the ratio of circle circumference to circle diameter) and the diameter DD of the top face of the frustocone KS is approx. 5 mm. Finally, the ringlike shaped precursor bodies are treated thermally under air in the temperature range from 400 to 500° C. The resulting ringlike shaped multimetal oxide unsupported catalyst bodies are suitable, for example, as catalysts for the partial oxidation of methanol to formaldehyde.

The present patent application thus comprises especially the following inventive embodiments:

1. A process for producing a ringlike oxidic shaped body comprising the mechanical compaction of a pulverulent aggregate which has been introduced into the fill chamber of a die and is composed of constituents which comprise at least one metal compound which can be converted to a metal oxide by thermal treatment at a temperature of $\geq 100°$ C., or at least one metal oxide, or at least one metal oxide and at least one such metal compound, to give a ringlike shaped precursor body, in which the fill chamber is disposed in a die bore conducted through the die material from the top downward with a vertical bore axis B and is delimited by the inner wall of the die bore, the upper end face of a lower punch introduced from below along the bore axis B into the die bore so as to be liftable and lowerable, on which the pulverulent aggregate introduced into the fill chamber rests, the lower end face, disposed along the bore axis B at an axial starting distance A above the upper end face of the lower punch, of an upper punch mounted so as to be liftable and lowerable along the bore axis B, whose lower end face is in contact with the pulverulent aggregate introduced into the fill chamber from above, and the outer face of a center pin MF conducted from the bottom upward in the die bore along the bore axis B from the geometric center of the upper end face of the lower punch, said center pin MF extending at least up to the geometric center of the lower end face of the upper punch, by reducing the axial starting distance A of the two end faces along the bore axis B to an axial end distance E predefined for the compaction by lowering the upper punch while maintaining the position of the lower punch or additionally lifting the lower punch, where the geometric shape of the outer face of the lower punch corresponds to that of the outer face of a circular cylinder I;

the geometric shape of the outer face of the upper punch corresponds to that of the outer face of a circular cylinder II;

in the geometric center of the upper end face of the lower punch, a center bore $MB^U$ conducted through the lower punch from the top downward is formed;

at the starting distance A of the two end faces, the center pin MF projects from below through the center bore $MB^U$ at least up to the geometric center of the lower end face of the upper punch;

the center pin MF, from the bottom upward, has the geometric shape of a circular cylinder Z with a circular cylindrical outer face MZ;

the length of the outline of the circular cylinder Z is less than the length of the outline of the circular cylinder I and less than the length of the outline of the circular cylinder II;

the position of the center pin MF and the position of the die including the die bore along the bore axis B are fixed relative to one another during the process;

in the geometric center of the lower end face of the upper punch, a center bore $MB^O$ which is conducted into the upper punch and is connected to at least one outlet from the upper punch is formed, said center bore $MB^O$ being capable of accommodating the center pin MF to the necessary degree in the event of reduction of the starting distance A to the end distance E, and the center pin MF being able to project into it even at the starting distance A;

the axes of symmetry of the die bore, of the circular cylinder I, of the circular cylinder II, of the center bore $MB^O$, of the center pin MF and of the center bore $MB^U$ are on a common straight line L running vertically through the die bore;

the die bore, along its bore axis, has a longitudinal section I over whose length I the geometric shape of the inner wall of the die bore corresponds to that of the outer face of a circular cylinder KZ, and which is adjoined at its upper end directly by a longitudinal section II of the die bore which is directed upward and has is the length II;

the dimensions of the longitudinal section I of the die bore and of the circular cylinder I are such that the lower punch, during the process, is always conducted in each case sliding into the die bore at least for part of the length of the longitudinal section I with its outer face on the inner wall of the die bore;

the dimensions of the center bore $MB^U$ and of the circular cylinder Z are such that the lower punch, during the process, is always conducted sliding into the die bore at least in the region of the entrance of its center bore $MB^U$ into its upper end face with the inner wall of the center bore $MB^U$ on the circular cylindrical outer face MZ of the center pin MF; and on completion of compaction, the upper punch is lifted from the ringlike shaped precursor body formed and the ringlike shaped precursor body is removed from the die bore by lifting the lower punch, and a subsequent process for thermal treatment of the ringlike shaped precursor body at a temperature of $\geq 100°$ C., in which at least a portion of its constituents is decomposed and/or converted chemically to form at least one gaseous compound and the ringlike oxidic shaped body forms, wherein the geometric shape of the inner wall of the die bore, over the length II of the longitudinal section II, from the bottom upward, corresponds to that of the outer face of a frustocone KS which widens from the bottom upward, whose cross-sectional area, at its lower end, corresponds to the cross-sectional area of the circular cylinder KZ at its upper end, with the proviso that, on attainment of the end distance E, the lower end face of the upper punch is in the longitudinal section II and the upper end face of the lower punch is not below the longitudinal section I, such that the ringlike shaped precursor body formed by the mechanical compaction of the pulverulent aggregate between the two end faces is at least partly in the longitudinal section II on attainment of the end distance E.
2. The process according to embodiment 1, wherein, on attainment of the end distance E between the upper end face of the lower punch and the lower end face of the upper punch, at least 20% of the distance between the two end faces is within the longitudinal section II.
3. The process according to embodiment 1, wherein, on attainment of the end distance E between the upper end face of the lower punch and the lower end face of the upper punch, at least 60% of the distance between the two end faces is within the longitudinal section II.
4. The process according to embodiment 1, wherein, on attainment of the end distance E between the upper end face of the lower punch and the lower end face of the upper punch, at least 90% of the distance between the two end faces is within the longitudinal section II.
5. The process according to embodiment 1, wherein, on attainment of the end distance E between the upper end face of the lower punch and the lower end face of the upper punch, all of the ringlike shaped precursor body formed by the mechanical compaction of the pulverulent aggregate between the two end faces is within the longitudinal section II.
6. The process according to any one of embodiments 1 to 5, wherein the outline of the circular cylinder II is longer than or is equal in length to the outline of the circular cylinder I.
7. The process according to any one of embodiments 1 to 6, wherein the upper end face or the lower punch and the lower end face of the upper punch are in planes parallel to one another, to which the bore axis B is at right angles.
8. The process according to any one of embodiments 1 to 7, wherein the end distance E is from 2 to 10 mm.
9. The process according to any one of embodiments 1 to 7, wherein the end distance E is from 2 to 8 mm.
10. The process according to any one of embodiments 1 to 7, wherein the end distance E is from 3 to 8 mm.
11. The process according to any one of embodiments 1 to 7, wherein the end distance E is from 3 to 7 mm.
12. The process according to any one of embodiments 1 to 11, wherein the quotient Q of the length of the outline of the circular cylinder Z as the numerator and the outline of the circular cylinder I as the denominator is from 0.3 to 0.7.
13. The process according to any one of embodiments 1 to 11, wherein the quotient Q of the length of the outline of the circular cylinder Z as the numerator and the outline of the circular cylinder I as the denominator is from 0.4 to 0.6.
14. The process according to any one of embodiments 1 to 12, wherein the difference formed by subtracting the radius of the outline of the circular cylinder Z from the radius of the outline of the circular cylinder I is from 1 to 3 mm.
15. The process according to any one of embodiments 1 to 14, wherein the diameter of the outline of the circular cylinder I is from 2 to 10 mm.
16. The process according to any one of embodiments 1 to 14, wherein the diameter of the outline of the circular cylinder I is from 2 to 8 mm.
17. The process according to any one of embodiments 1 to 14, wherein the diameter of the outline of the circular cylinder I is from 4 to 8 mm.
18. The process according to any one of embodiments 1 to 17, wherein the frustocone KS is such that the following relationship between the diameter DD of the top face, the diameter DG of the bottom face and the height H of the frustocone KS is satisfied:

$$0.003 \cdot H \leq DG - DD \leq 0.050 \cdot H.$$

19. The process according to any one of embodiments 1 to 17, wherein the frustocone KS is such that the following relationship between the diameter DD of the top face, the diameter DG of the bottom face and the height H of the frustocone KS is satisfied:

$$0.005 \cdot H \leq DG - DD \leq 0.025 \cdot H.$$

20. The process according to any one of embodiments 1 to 17, wherein the frustocone KS is such that the following relationship between the diameter DD of the top face, the diameter DG of the bottom face and the height H of the frustocone KS is satisfied:

$$0.007 \cdot H \leq DG - DD \leq 0.015 \cdot H.$$

21. The process according to any one of embodiments 1 to 20, wherein both the upper end face (accessible to the pulverulent aggregate) of the lower punch and the lower end face (accessible to the pulverulent aggregate) of the upper punch have the geometric shape of a circular ring.
22. The process according to any one of embodiments 1 to 20, wherein both the upper end face of the lower punch and the lower end face of the upper punch have the geometric shape of a circular ring curved inward into the interior of the punch.
23. The process according to any one of embodiments 1 to 22, wherein the die bore has only the longitudinal sections I and II.
24. The process according to any one of embodiments 1 to 22, wherein the die bore of the die is such that its longitudinal section I is not only adjoined at its upper end directly by a longitudinal section II directed upward, but also at its lower end directly by a longitudinal section II* of length II* directed downward, and the geometric shape of the inner wall of the die bore, over the length II* of the longitudinal section II*, corresponds to the outer face of a frustocone KS* whose cross-sectional area at its upper end corresponds to the cross-sectional area of the circular cylinder KZ at its lower end.
25. The process according to embodiment 24, wherein the die bore has only the longitudinal sections I, II and II*.
26. The process according to embodiment 24 or 25, wherein the geometric dimensions of longitudinal section II correspond to those of longitudinal section II*.
27. The process according to any one of embodiments 1 to 26, wherein the following relationship between the height H of the frustocone KS and the end distance E is satisfied:

$$4 \cdot \text{end distance } E \geq H \geq 1 \cdot \text{end distance } E.$$

28. The process according to any one of embodiments 1 to 26, wherein the following relationship between the height H of the frustocone KS and the end distance E is satisfied:

$$3 \cdot \text{end distance } E \geq H \geq 1 \cdot \text{end distance } E.$$

29. The process according to any one of embodiments 1 to 26, wherein the following relationship between the height H of the frustocone KS and the end distance E is satisfied:

$$3 \cdot \text{end distance } E \geq H \geq 1.5 \cdot \text{end distance } E.$$

30. The process according to any one of embodiments 1 to 29, wherein the length of longitudinal section I is greater than the length II of longitudinal section II.

31. The process according to any one of embodiments 1 to 29, wherein the length of longitudinal section I is less than the length II of longitudinal section II.
32. The process according to any one of embodiments 1 to 29, wherein the length of longitudinal section I is not more than three times and not less than 0.1 times the length of longitudinal section II.
33. The process according to any one of embodiments 1 to 32, wherein at least the entrance into the center bore $MB^O$ is configured in circular cylindrical form such that the outer face of the circular cylinder Z, when it is accommodated into the center bore $MB^O$, slides along its inner wall at least in the entrance region thereof.
34. The process according to any one of embodiments 1 to 33, wherein the center pin MF narrows conically in the upward direction within the longitudinal section II.
35. The process according to any one of embodiments 1 to 34, wherein the upper end of longitudinal section II of the die bore, the upper end face of the center pin MF and the upper end face of the die conclude flush with one another.
36. The process according to any one of embodiments 1 to 35, wherein the process according to the invention is performed automatically with the aid of a rotary press.
37. The process according to any one of embodiments 1 to 36, wherein the mechanical compaction consists of a preliminary compaction and of a main compaction following thereafter, the axial starting distance A, in the course of the preliminary compaction, first being reduced to a preliminary end distance $E^V$, and the preliminary end distance $E^V$ being reduced to the end distance E in the course of the main compaction.
38. The process according to any one of embodiments 1 to 37, wherein the pulverulent aggregate comprises at least one metal oxide, metal hydroxide, metal carbonate, metal hydrogencarbonate, metal hydrogenphosphate and/or metal nitrate.
39. The process according to any one of embodiments 1 to 38, wherein the pulverulent aggregate comprises at least one metal nitrate from the group consisting of cobalt nitrate, iron nitrate, bismuth nitrate, nickel nitrate, cesium nitrate, copper nitrate, calcium nitrate and magnesium nitrate.
40. The process according to any one of embodiments 1 to 39, wherein the die is manufactured from a material composite which consists of a hard metal on its side in contact with the die bore and of a tool steel on its side facing away from the die bore, said tool steel having the following element composition:
   1.50 to 1.80% by wt. of C,
   0.10 to 0.40% by wt. of Si,
   0.10 to 0.50% by wt. of Mn,
   $\geq 0$ to 0.05% by wt. of P,
   $\geq 0$ to 0.05% by wt. of S,
   10 to 13% by wt. of Cr,
   0.50 to 0.80% by wt. of Mo,
   0.10 to 1.10% by wt. of V,
   $\geq 0$ to 0.60% by wt. of W, and
   $\geq 0$ to 0.10% by wt. of one or more rare earth metals, and apart from these Fe and impurities resulting from the production.
41. The process according to embodiment 40, wherein the hard metal consists of tungsten carbide to an extent of $\geq 90\%$ by weight and of nickel or of nickel and chromium to an extent of at least 5% by weight.
42. The process according to embodiment 40, wherein the hard metal consists of
   90 to 95% by wt. of WC
   $\geq 0$ to 1% by wt. of TiC and/or TaNbC, and
   5 to 10% by wt. of Ni or Ni and Cr.
43. The process according to any one of embodiments 1 to 42, wherein the pulverulent aggregate comprises nitric acid, an ammonium salt and/or a nitrate salt.
44. The process according to any one of embodiments 1 to 43, wherein the mean roughness $R_a$ of the inner wall of the die bore is $\leq 0.2$ µm.
45. The process according to any one of embodiments 1 to 43, wherein the mean roughness $R_a$ of the inner wall of the die bore is $\leq 0.1$ µm.
46. The process according to any one of embodiments 1 to 45, wherein, at the end distance E, the two punches exert a pressure which is in the range from 50 to 5000 kg/cm².
47. The process according to any one of embodiments 1 to 45, wherein, at the end distance E, the two punches exert a pressure which is in the range from 500 to 2500 kg/cm².
48. The process according to any one of embodiments 1 to 47, wherein the process for thermal treatment of the ringlike shaped precursor bodies produced is effected at a temperature of $\geq 200°$ C.
49. The process according to any one of embodiments 1 to 47, wherein the process for thermal treatment of the ringlike shaped precursor bodies produced is effected at a temperature of $\geq 300°$ C.
50. The process according to any one of embodiments 1 to 49, wherein the thermal treatment of the ringlike shaped precursor bodies is accompanied by a weight loss of from 0.5 to 40% by weight based on its starting weight.
51. The process according to any one of embodiments 1 to 50, wherein the at least one gaseous compound which forms in the course of thermal treatment is ammonia, $H_2O$, CO, $CO_2$ and/or a nitrogen oxide.
52. The process according to any one of embodiments 1 to 51, wherein the pulverulent aggregate comprises at least one added substance from the group consisting of $NH_4OH$, $(NH_4)_2CO_3$, $NH_4HCO_3$, $NH_4NO_3$, $NH_4CHO_2$, $NH_4HSO_4$, $(NH_4)_2SO_4$, $NH_4CH_3CO_2$, ammonium oxalate and the hydrates of the aforementioned ammonium salts.
53. The process according to any one of embodiments 1 to 52, wherein the pulverulent aggregate comprises added graphite, starch, ground nutshell, fine polymer granule, cellulose, stearic acid, malonic acid, salt of stearic acid and/or salt of malonic acid.
54. The process according to any one of embodiments 1 to 53, wherein the subsequent process for thermal treatment of the ringlike shaped precursor bodies produced forms a multimetal oxide in the ringlike shaped precursor bodies which comprises the elements Mo and Fe, or the elements Mo, Fe and Bi, or the elements Mo and V, or the elements Mo, V and P, or the elements V and P.
55. The process according to any one of embodiments 1 to 54, wherein the subsequent process for thermal treatment of the ringlike shaped precursor bodies produced forms a multimetal oxide in which the element Mo, or the element V, or the element P is that element other than oxygen which, calculated in molar terms, is the numerically most common.
56. The process according to any one of embodiments 1 to 55, wherein the subsequent process for thermal treatment of the ringlike shaped precursor bodies produced forms a multimetal oxide of the general formula XII

 (XII)

where
   $X^1$=nickel and/or cobalt,
   $X^2$=thallium, samarium, an alkali metal and/or an alkaline earth metal, $X^3$=zinc, phosphorus, arsenic, boron, antimony, tin, cerium, lead, vanadium, chromium, niobium and/or tungsten, $X^4$=silicon, aluminum, titanium and/or zirconium, a=0.2 to 5,
b=0.01 to 5,
c=0 to 10,
d=0 to 2,
e=0 to 8,
f=0 to 10, and
n=a number which is determined by the valency and frequency of the elements in XII other than oxygen.

57. The process according to any one of embodiments 1 to 55, wherein the subsequent process for thermal treatment of the ringlike shaped precursor bodies produced forms a multimetal oxide of the general formula XIII

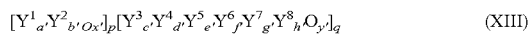

$$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \quad (XIII)$$

where
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum or tungsten, or molybdenum and tungsten,
a'=0.01 to 8,
b'=0.1 to 30,
c'=0 to 4,
d'=0 to 20,
e'>0 to 20,
f'=0 to 6,
g'=0 to 15,
h'=8 to 16,
x', y'=numbers which are determined by the valency and frequency of the elements in XIII other than oxygen, and
p, q=numbers whose p/q ratio is from 0.1 to 10.

58. The process according to any one of embodiments 1 to 55, wherein the subsequent process for thermal treatment of the ringlike shaped precursor bodies produced forms a multimetal oxide of the general formula XIV

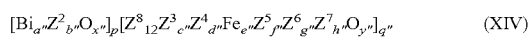

$$[Bi_{a''}Z^2_{b''}O_{x''}]_p[Z^8_{12}Z^3_{c''}Z^4_{d''}Fe_{e''}Z^5_{f''}Z^6_{g''}Z^7_{h''}O_{y''}]_{q''} \quad (XIV)$$

where
$Z^2$=molybdenum or tungsten, or molybdenum and tungsten,
$Z^3$=nickel and/or cobalt,
$Z^4$=thallium, an alkali metal and/or an alkaline earth metal, preferably K, Cs and/or Sr,
$Z^5$=phosphorus, arsenic, boron, antimony, tin, cerium, vanadium, chromium and/or Bi,
$Z^6$=silicon, aluminum, titanium and/or zirconium, preferably Si,
$Z^7$=copper, silver and/or gold,
$Z^8$=molybdenum or tungsten, or molybdenum and tungsten,
a''=0.1 to 1,
b''=0.2 to 2,
c''=3 to 10,
d''=0.02 to 2,
e''=0.01 to 5, preferably 0.1 to 3,
f''=0 to 5,
g''=0 to 10, preferably >0 to 10, more preferably 0.2 to 10 and most preferably 0.4 to 3,
h''=0 to 1,
x'', y''=numbers which are determined by the valency and frequency of the elements in XIV other than oxygen, and
p'', q''=numbers whose p''/q'' ratio is from 0.1 to 5.

59. The process according to any one of embodiments 1 to 55, wherein the subsequent process for thermal treatment of the ringlike shaped precursor bodies produced forms a multimetal oxide of the general formula XV

$$Mo_{12}P_aV_bX_c^1X_d^2X_e^3Sb_fRe_gS_hO_n \quad (XV)$$

where
$X^1$=potassium, rubidium and/or cesium,
$X^2$=copper and/or silver,
$X^3$=cerium, boron, zirconium, manganese and/or bismuth,
a=0.5 to 3,
b=0.01 to 3,
c=0.2 to 3,
d=0.01 to 2,
e=0 to 2,
f=0 to 2, preferably 0.01 to 2,
g=0 to 1,
h=0 to 0.5, preferably 0.001 to 0.5, and
n=a number which is determined by the valency and frequency of the elements in XV other than oxygen.

60. The process according to any one of embodiments 1 to 55, wherein the subsequent process for thermal treatment of the ringlike shaped precursor bodies produced forms a multimetal oxide of the general formula XVI

$$V_1P_bFe_cX^1_dX^2_eO_n \quad (XVI)$$

where
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b=0.9 to 1.5,
c=0 to 0.1,
d=0 to 0.1,
e=0 to 0.1, and
n=a number which is determined by the valency and frequency of the elements in XVI other than oxygen.

61. The process according to any one of embodiments 1 to 53, wherein the subsequent process for thermal treatment of the ringlike shaped precursor bodies produced forms an oxide which is solid under standard conditions and in which no transition metal of transition group 5 to 11 nor phosphorus is that element other than oxygen which, calculated in molar terms, is the numerically most common.

62. The process according to any one of embodiments 1 to 53, wherein the pulverulent aggregate comprises at least one metal oxide from the group consisting of aluminum oxide, tungsten oxide, antimony oxide, zirconium oxide, bismuth oxide, molybdenum oxide, silicon oxide, magnesium oxide and mixed oxides which comprise at least two of the metal elements present in the aforementioned metal oxides.

63. The process according to any one of embodiments 1 to 62, wherein, already at the starting distance A, both the upper end face of the lower punch and the lower end face of the upper punch are in the longitudinal section II of the die bore.

64. A ringlike oxidic shaped body obtainable by a process according to any one of embodiments 1 to 63.

65. A process for heterogeneously catalyzed partial gas phase oxidation of at least one organic compound over a fixed catalyst bed, wherein the fixed catalyst bed comprises a ringlike oxidic shaped body according to embodiment 64.

66. The process according to embodiment 65, wherein the heterogeneously catalyzed partial gas phase oxidation is that
   a) of propylene to acrolein and/or acrylic acid or
   b) of acrolein to acrylic acid, or
   c) of methacrolein to methacrylic acid, or
   d) of isobutene to methacrolein and/or methacrylic acid, or
   e) of propane to acrolein and/or acrylic acid, or
   f) of isobutane to methacrolein and/or methacrylic acid, or
   g) of at least one $C_4$ hydrocarbon and/or benzene to maleic anhydride, or
   h) of methanol to formaldehyde or
   i) the oxychlorination of ethylene to 1,2-dichloroethane.

67. A tube bundle reactor whose reaction tubes comprise at least one ringlike oxidic shaped body according to embodiment 64.

EXAMPLES AND COMPARATIVE EXAMPLES

I. Production of Ringlike Shaped Support Precursor Bodies 220 kg of fine γ-$Al_2O_3$ (Puralox® SCF a-230 from Sasol in D-25534 Brunsbüttel), 148 kg of fine pseudoboehmite (Pural® SCF 55 from Sasol), 12 kg of magnesium stearate (from Peter Greven Fett-Chemie GmbH, melting point 145-160° C., bulk density 200-300 g/h, ash 6.8-8.3% by weight, moisture <2.0% by weight) and 4.0 kg of fine graphite (Timrex®) T44 from Timcal AG Ltd., 6743 Bodio, Switzerland, with $d_{10}$=6.4 µm, $d_{50}$=20.8 µm, $d_{90}$=56.8 µm) were used to obtain a homogeneous pulverulent aggregate with the aid of a mixer.

The specification of the Puralox was:
specific surface area=212 $m^2$/g,
$Al_2O_3$ content=99.3% by weight,
Apparent density=0.61 g/ml,
Bulk density=0.80 g/ml,
Si content=45 ppm by weight,
Fe content=96 ppm by weight,
Na content=19 ppm by weight,
>12 µm=85.5% by weight,
<25 µm=34.2% by weight,
<45 µm=68.5% by weight,
>64 µm=12.6% by weight,
<90 µm=96.9% by weight,
$d_{50}$=33.8 µm.

The specification of the Pural was:
specific surface area=239 $m^2$/g,
$Al_2O_3$ content=75.1% by weight,
Apparent density=0.62 g/ml,
Bulk density=0.90 g/ml,
Carbon=0.14% by weight,
>12 µm=72.6% by weight,
<25 µm=68.1% by weight,
<45 µm=95.5% by weight,
>48 µm=3.0% by weight,
<90 µm=100% by weight,
$d_{50}$=18.8 µm.

Subsequently, the pulverulent aggregate was compacted in accordance with the invention with the aid of a Kilian Synthesis 700 rotary press (single mold, 77 dies). The fundamental apparatus construction was as in FIG. 6. The diameter of the preliminary pressure roller was 210 mm and the diameter of the main pressure roller was likewise 210 mm. The distance between two dies opposite one another on the die plate was 720 mm.

The dies used were dies with a congruent double frustocone as shown schematically in FIGS. 3a, 3b.

The length I of longitudinal section I was 6.2 mm.

The length II (the length II*) of longitudinal section II (of longitudinal section II*) was 8 mm.

The outline of circular cylinder I and of circular cylinder II was 15.7 mm.

The diameter DD of the top face of the frustocone KS was 5.1 mm.

The diameter DG of the bottom face of the frustocone KS was 5.0 mm.

The length of the outline of the circular cylinder Z (of the continuous circular cylindrical center pin) was 2.5·π mm. The upper planar end face of the center pin MF concluded flush with the planar upper die end face.

Both center bores, $MB^U$ and $MB^O$ (the latter was connected to two gas-permeable outlets (cf. FIG. 4d)), had, in the entrance region into the corresponding end face, a circular cylindrical geometry with identical radius. The contact of their inner walls to the outer surface of the center pin MF was sliding against one another in the area of possible contact.

Only ringlike shaped precursor bodies $F^{LII}$ were manufactured, and the end distance E was always 5 mm.

The upper end face of the lower punch and the lower end face of the upper punch, in accordance with EP-A 184790, had a concave configuration in an identical (congruent) manner. The bore axis B ran at right angles to both punch cross sections. The channel depth was 0.8 mm.

The individual die was manufactured from a material composite. This consisted, on its side in contact with the die bore, of the hard metal G 10-Ni (wall thickness from 6.9 to 7.0 mm) where $R_a$=0.1 µm and, on its side facing away from the die bore, of DIN tool steel 1.2379 (wall thickness 6 mm) where $R_a$=0.8 µm. The upper punch and the lower punch were manufactured from DIN material 1.2601. The center pin MF which was circular cylindrical over its entire length was manufactured from DIN tool steel 1.2343 ($R_a$=0.4 µm). $R_a$ of the two end faces was likewise 0.4 µm.

The amount of pulverulent aggregate introduced into the fill chamber was 118 mg. At the start of the process, the lower face of the upper punch, in the state of the starting distance A, concluded flush with the upper end of longitudinal section II. With increasing wear on the inner wall of the upper part of longitudinal section II of the die bore, in the state of the starting distance A, the positions of the two end faces within longitudinal section II were shifted downward.

The initial pressing force applied was 0.5 kN for each of the two punches; the main pressing force applied was 8.5 kN for each of the two punches (pressing force data are always based on the state of the end distance E).

The side crushing strengths of the resulting ringlike shaped support precursor bodies were in the range from 19 to 23 N.

The rotation rate of the rotary press was from 25 to 30 rpm.

With regard to the material of die table tongue, die table brow and die table chin, the statements in the description apply.

Subsequently, the resulting ringlike shaped support precursor bodies were treated thermally on a belt calciner (cf. DE-A 10046957 and WO 02/24620). The bulk material height on the circulating belt was 80 mm. The temperature in the first calcination chamber was 690° C.; that in the second calcination chamber was 700° C. The coarse-mesh belt was flowed through from the bottom with forced air, which was sucked in by means of rotating ventilators such that the deviation of the temperature from the target value in terms of time and space was always ≦2° C. The residence time in the first chamber was 2 h and the residence time in the second chamber was likewise 2 h.

Subsequently, the ringlike shaped support bodies formed were subjected to screening. The screens used were screens with elongated holes. In the screening off of oversize, its straight edge length was 20 mm and the distance between the two edges was 8 mm. In the subsequent undersize screening, its straight edge length was 4 mm and the distance between the two edges was 2 mm.

Based on the weight of all of the screening material introduced to the screening, the undersize fraction obtained was 2% by weight.

When the procedure was the same as described above, except that the compaction of the pulverulent aggregate was performed with a die whose die bore was an ideal circular cylinder (diameter=5 mm; the diameter of the upper and of the lower end face was 4.95 mm), the undersize fraction obtained in the screening was 7% by weight.

Alternatively to the described inventive compaction with the aid of a Kilian Synthesis 700 rotary press, the inventive compaction can also be performed with a Kirsch PH 800 rotary press. In this case, compaction is effected without preliminary pressure. The main pressing force employed may, for example, be 8.2 kN for each of the two punches.

The ringlike shaped support bodies produced as described are suitable, for example, for the end use described in WO 99/48606.

II. Production of Ringlike Shaped Multimetal Oxide Unsupported Catalyst Precursor Bodies where the Active Multimetal Oxide has the Stoichiometry

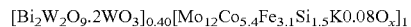

1. Production of a Starting Composition 1

214.7 kg of tungstic acid at 25° C. (74.1% by weight of W, H.C. Starck, D-38615 Goslar, purity >99.9% by weight of $WO_3$ after ignition at 750° C., 0.4 μm<$d_{50}$<0.8 μm) were stirred (70 rpm) in portions into 780 kg of an aqueous bismuth nitrate solution in nitric acid at 25° C. (11.2% by weight of Bi; free nitric acid 3 to 5% by weight; apparent density: 1.22 to 1.27 g/ml, prepared with nitric acid from bismuth metal from Sidech S. A., 1495 Tilly, Belgium, purity: >99.997% by weight of Bi, <7 mg/kg of Pb, <5 mg/kg each of Ni, Ag, Fe, <3 mg/kg each of Cu, Sb, and <1 mg/kg of Cd, Zn) at 25° C. within 20 min. The resulting aqueous mixture was subsequently stirred at 25° C. for another 3 h and then spray-dried.

The spray-drying was effected in a rotary-disk spray tower in hot air concurrent at a gas inlet temperature of 300±10° C., a gas outlet temperature of 100±10° C., a disk speed of 18 000 rpm and a throughput of 200 l/h. The resulting spray powder had an ignition loss of 12.8% by weight (calcine under air for 3 h at 600° C. in a porcelain crucible (which had been calcined to constant weight at 900° C.)) and had (at a dispersion pressure of 1.1 bar absolute) a $d_{50}$ of 28.0 μm ($d_{10}$=9.1 μm, $d_{90}$=55.2 μm). FIG. 9 shows the particle diameter distribution of the resulting spray powder as a function of the dispersion pressure employed.

The abscissa shows the particle diameters in a logarithmic plot in μm.

The ordinate shows the proportion by volume in % of the total particle volume that has the appropriate particle diameter as a function of the dispersion pressure employed:

▲: Dispersion pressure=2 bar abs.
■: Dispersion pressure=1.5 bar abs.
●: Dispersion pressure=1.2 bar abs.
◆: Dispersion pressure=1.1 bar abs.

The table which follows gives an overview of representative $d_x$ values as a function of the absolute dispersion pressure employed:

|  | 2 bar | 1.5 bar | 1.2 bar | 1.1 bar |
| --- | --- | --- | --- | --- |
| $d_{10}$ (μm) | 0.91 | 1.17 | 3.4 | 9.1 |
| $d_{50}$ (μm) | 5.8 | 8.5 | 19.7 | 28.0 |
| $d_{90}$ (μm) | 27.5 | 34.3 | 47.2 | 55.2 |

The resulting spray powder was subsequently converted to a paste with 16.7% by weight (based on the powder) of water at 25° C. in a kneader (20 rpm) for 30 min and extruded by means of an extruder (torque: ≦50 Nm) to extrudates of diameter 6 mm. These were cut into sections of 6 cm, dried on a 3-zone belt dryer with a residence time of 120 min per zone at temperatures of 90-95° C. (zone 1), 115° C. (zone 2) and 125° C. (zone 3) under air, and then treated thermally at a temperature in the region of 830° C. (calcined; in a rotary tube oven with air flow (reduced pressure 0.3 mbar, internal volume 1.54 m³, 200 m³ (STP)/h of air, 50 kg/h of extrudate, speed: 1 rpm, 7 cm inclination of the rotary tube with length 4 m)). What is important in the precise setting of the calcination temperature is that it has to be oriented to the desired phase composition of the calcination product. The $WO_3$ (monoclinic) and $Bi_2W_2O_9$ (orthorhombic) phases are desired; the presence of y-$Bi_2WO_6$ (russellite) is undesired. Should, therefore, after the calcination, the compound y-$Bi_2WO_6$ still be detectable on the basis of a reflection in the X-ray powder diffractogram at a reflection of 2Θ=28.4° (CuKα radiation), the preparation should be repeated and the calcination temperature within the temperature range specified or the residence time at the same calcination temperature should be increased until the disappearance of the reflection is achieved. The preformed calcined mixed oxide thus obtained was ground at 2500 rpm with a BQ500 Biplex mill, such that the $d_{50}$ value was 2.45 μm ($d_{10}$=1.05 μm, $d_{90}$=5.9 μm, measured at a dispersion pressure of 2 bar absolute) and the BET surface area was 0.8 m²/g.

The grinding material was then mixed in portions of 20 kg in an inclined mixer (VIS type, fill volume: 60 l, Aachener Misch- und Knetmaschinenfabrik) with mixing and cutting blades (mixing blade speed: 60 rpm, cutting blade speed: 3000 rpm) homogeneously within 5 min with 0.5% by weight (based on the grinding material) of fine $SiO_2$ from Degussa of the Sipernat® D17 type (tapped density 150 g/l; $d_{50}$ of the $SiO_2$ particles (laser diffraction to ISO 13320-1) was 10 μm, the specific surface area (nitrogen adsorption to ISO 5794-1, Annex D) was 100 m²/g).

2. Production of a Starting Composition 2

A solution A was prepared by metering 1.075 kg of an aqueous potassium hydroxide solution at 60° C. (47.5% by weight of KOH) and then, with a metering rate of 600 kg/h, 237.1 kg of ammonium heptamolybdate tetrahydrate (white crystals having a particle size d of <1 mm, 81.5% by weight of $MoO_3$, 7.0-8.5% by weight of $NH_3$, max. 150 mg/kg of alkali metals, H. C. Starck, D-38642 Goslar) at 60° C. with stirring (70 rpm) into 660 l of water at a temperature of 60° C. within one minute, and stirring the resulting slightly cloudy solution at 60° C. for 60 min.

A solution B was prepared by initially charging, at 60° C., 282.0 kg of an aqueous cobalt(II) nitrate solution at a temperature of 60° C. (12.5% by weight of Co, prepared with nitric acid from cobalt metal from MFT Metals & Ferro-Alloys Trading GmbH, D-41747 Viersen, purity: >99.6% by weight, <0.3% by weight of Ni, <100 mg/kg of Fe, <50 mg/kg of Cu) and metering thereto, with stirring (70 rpm), 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal). Subsequently, while maintaining the 60° C., the mixture was stirred for a further 30 minutes. Then, while retaining the 60° C., solution B was discharged into the initially charged solution A and the mixture was stirred at 60° C. for a further 15 minutes. Subsequently, 19.9 kg of silica gel from Grace GmbH in D-67547 Worms of the Ludox® TM-50 type (50% by weight of $SiO_2$; stabilizing counterion: $Na^+$; particle charge: negative; Si:Na ratio as the $SiO_2/Na_2O$ weight ratio: 225; $SiO_2$ content: 50% by weight; pH: 9.0; apparent density (25° C., 1 atm): 1.40 $g/cm^3$; sulfates (as $Na_2SO_4$): 0.08% by weight; titratable alkali (as $Na_2O$): 0.21% by weight; viscosity (25° C., 1 atm): 40 cP; specific surface area of the $SiO_2$ particles: 140 $m^2/g$) were added to the resulting aqueous mixture which was then stirred at 60° C. for a further 15 minutes.

Subsequently, the product was spray-dried in a Niro FS-15 rotary-disk spray tower in hot air countercurrent (gas inlet temperature: 350±10° C., gas outlet temperature: 140±5° C., disk speed: 18 000 rpm, throughput: 270 kg/h). The resulting spray powder had an ignition loss of 30.5% by weight (calcine at 600° C. in a porcelain crucible (which had been calcined to constant weight at 900° C.) under air for 3 h) and, (at a dispersion pressure of 2.0 bar absolute) a $d_{50}$ of 23.6 μm ($d_{10}$=5.2 μm, $d_{90}$=49.5 μm). FIG. 10 shows the particle diameter distribution of the resulting spray powder as a function of the dispersion pressure employed.

The abscissa shows the particle diameters in a logarithmic plot in μm.

The ordinate shows the proportion by volume in % of the total particle volume that has the appropriate particle diameter as a function of the dispersion pressure employed:
▲: dispersion pressure=2 bar abs.
♦: dispersion pressure=1.1 bar abs.

The following table gives an overview of the representative $d_x$ values as a function of the absolute dispersion pressure employed:

|  | 2 bar | 1.1 bar |
|---|---|---|
| $d_{10}$ (μm) | 5.2 | 9.9 |
| $d_{50}$ (μm) | 23.6 | 28.5 |
| $d_{90}$ (μm) | 49.5 | 56.3 |

3. Production of the Shaped Multimetal Oxide Catalyst Bodies and Precursors Thereof 110 kg of starting composition 2 were then initially charged in an inclined mixer (VIL type, fill volume: 200 l, Aachener Misch- und Knetmaschinenfabrik) with mixing and cutting blades (mixing blade speed: 39 rpm, cutting blade speed: 3000 rpm) and premixed for 1 min. Within 10 min, with continued mixing, via a star feeder, starting composition 1 was metered thereto in the amount required for a multimetal oxide active composition of stoichiometry:

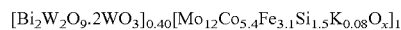
[$Bi_2W_2O_9 \cdot 2WO_3$]$_{0.40}$[$Mo_{12}Co_{5.4}Fe_{3.1}Si_{1.5}K_{0.08}O_x$]$_1$ within 10 min. The mixing operation was then continued for a further 15 min in order to achieve an intensive and complete homogenization (including the breaking apart of any agglomerates present) of the two starting materials (which is required to achieve a high activity and high acrolein selectivity). Based on the aforementioned overall composition, 1% by weight of TIMREX T44 graphite from Timcal AG was mixed in within a further 2 min.

The resulting mixture was then compacted in a K200/100 compactor from Hosokawa Bepex GmbH with concave, fluted smooth rollerers (gap width: 2.8 mm, rollerer speed: 9 rpm, target pressing force: approx. 75 kN). Integrated vibrating screens from Allgaier (oversize screen size: 1.5 mm, undersize screen size: 400 μm) with ball-type screening aids (diameter 22 mm) were used to isolate a compactate having a particle size for the most part between 400 μm and 1.5 mm.

For the tableting, a further 2.5% by weight of the TIMREX T44 graphite from Timcal AG were added to the compactate in a turbulent mixer from Drais over the course of 2 minutes.

Subsequently, the pulverulent aggregate obtained as described was compacted in accordance with the invention under an air atmosphere with the aid of a Korsch PH 865 rotary press (single mold, 65 dies). The fundamental apparatus construction was as in FIG. 6. The diameter of the preliminary pressure rollerer was 100 mm and the diameter of the main pressure rollerer was 300 mm. The distance between two dies opposite one another on the die table was 780 mm.

The dies used were dies with a congruent double frustocone as shown schematically in FIGS. 3a, 3b.

The length I of longitudinal section I was 6.22 mm.

The length II (length II*) of longitudinal section II (of longitudinal section II*) was 8 mm.

The outline of circular cylinder I and of circular cylinder II was 15.7 mm.

The diameter DD of the top face of the frustocone KS was 5.1 mm.

The diameter DG of the bottom face of the frustocone KS was 5.0 mm.

The length of the outline of the circular cylinder Z (of the continuous circular cylindrical center pin) was 2.5·π mm. The planar upper end face of the center pin MF concluded flush with the planar upper die end face.

Only ringlike shaped precursor bodies $F^{LII}$ were manufactured, and the end distance E was always 3 mm. The upper end face of the lower punch and the lower end face of the upper punch were both of planar configuration. The bore axis B was at right angles to both end faces.

Both center bores, $MB^U$ and $MB^O$ (the latter was connected to two gas-permeable outlets (cf. FIG. 4d)), had a circular cylindrical geometry with identical radius in the entrance region into the corresponding end face. The contact of their inner walls to the outer surface of the center pin MF was sliding on one another in the region of possible contact.

The individual die was manufactured from a material composite. This consisted, on its side in contact with the die bore, of the hard metal G 10-Ni (wall thickness from 6.9 to 7 mm) with $R_a$=0.1 μm and, on its side facing away from the die bore, of DIN tool steel 1.2379 (9 mm wall thickness) with $R_a$=0.8 μm. The upper punch and the lower punch were manufactured from DIN material 1.2601. The center pin MF, which was circular cylindrical over its entire length, was manufactured from DIN tool steel 1.2343 ($R_a$=0.4 μm). $R_a$ of the two end faces was likewise 0.4 μm.

The amount of pulverulent aggregate introduced into the fill chamber was 129 mg.

At the start of the process, the lower end face of the upper punch, in the state of the starting distance A, concluded flush with the upper end of longitudinal section II. With increasing wear on the inner wall of the upper part of longitudinal section II of the die bore, in the state of starting distance A, the positions of both end faces were shifted downward within longitudinal section II.

The preliminary pressing force employed was 0.3 kN for each of the two punches; the main pressing force employed was 4.2 kN for each of the two punches.

The side crushing strengths of the resulting ringlike shaped multimetal oxide unsupported catalyst precursor bodies were in the range from 21 to 23 N.

The rotation rate of the rotary press was from 35 to 45 rpm.

With regard to the material of die table tongue, die table brow and die table chin, the statements made in the description apply.

In order to prevent release of dust, the tableting machine was provided with an extractor system (300 to 400 m$^3$ (STP)/h). The extracted air was conducted through a filter which was cleaned periodically.

Subsequently, the ringlike shaped multimetal oxide unsupported catalyst precursor bodies produced were, as described in example 1 of DE-A 100 46 957 (except that the bed height in the decomposition (chambers 1 to 4) was 53 mm with a residence time per chamber of 1.23 h and, in the calcination (chambers 5 to 8) it was 153 mm with a residence time of 3.89 h), treated thermally by means of a belt calcining apparatus; the chambers had a base area (with a uniform chamber length of 1.40 m) of 1.29 m$^2$ (decomposition) and 1.40 m$^2$ (calcination), and were flowed through from below through the coarse-mesh belt by 50-210 m$^3$ (STP)/h of feed air preheated to 100° C. (decomposition) or 450° C. (calcination); in addition, the air was circulated by rotating ventilators (900 to 1450 rpm). Within the chambers, the deviation of the temperature from the target value in terms of time and location (typical values for zones 1 to 8 are: 140° C., 190° C., 220° C., 265° C., 380° C., 425° C., 460° C., 460° C.) was always ≦2° C. Beyond chamber 8, there followed a cooling zone of length 2 m, whose temperature was controlled to 70° C. Otherwise, the procedure was as described in example 1 of DE-A 100 46 957.

Subsequently, the ringlike shaped multimetal oxide unsupported catalyst bodies formed were subjected to undersize screening. The screens used were screens with elongated holes. Their straight edge length was 20 mm and the distance between the two edges was 1.8 mm. Based on the weight of all of the screening material introduced to the screening, the undersize fraction obtained was 0.4% by weight.

When the procedure was the same as described above, except that the compaction of the pulverulent aggregate was performed by means of a die whose die bore was an ideal circular cylinder (diameter=5 mm; the diameter of the upper and of the lower end face was 4.95 mm), the undersize fraction obtained in the screening was 2.1% by weight.

The ringlike multimetal oxide unsupported catalysts produced as described are suitable, for example, for the heterogeneously catalyzed partial gas phase oxidation of propylene to acrolein.

Alternatively to the inventive compaction with the aid of a Korsch PH 865 rotary press, the inventive compaction can also be performed with a Kilian Synthesis 700-77 A rotary press. In this case, the preliminary pressing force employed may be 0.6 kN for each of the two punches and the main pressing force 5.0 kN for each of the two punches. In addition, the inventive compaction can also be carried out in a nitrogen atmosphere.

III. Production of Ringlike Shaped Multimetal Oxide Unsupported Catalyst Precursor Bodies where the Active Multimetal Oxide had the Stoichiometry $Mo_{12}Co_7Fe_{2.94}Bi_{0.6}Si_{1.59}K_{0.08}O_x$ At 60° C., 213 kg of ammonium heptamolybdate tetrahydrate (81.5% by weight of MoO$_3$) were dissolved in 600 l of water. While maintaining the 60° C., 0.97 kg of a 46.8% by weight aqueous potassium hydroxide solution of 20° C. was stirred into this solution (to obtain a solution A).

A second solution B was prepared by adding, at 30° C., 116.25 kg of an aqueous iron(III) nitrate solution (14.2% by weight of Fe) at 20° C. with stirring to 333.7 kg of an aqueous cobalt(II) nitrate solution (12.4% by weight of Co). After the addition had ended, stirring was continued at 30° C. for another 30 min. Thereafter, 112.3 kg of an aqueous bismuth nitrate solution (11.2% by weight of Bi) at 20° C. were stirred in at 60° C. to obtain solution B. Within 30 min, solution B was stirred into solution A at 60° C. 15 min after the stirring-in had ended, 19.16 kg of silica sol (of the Ludox TM-50 type from Grace GmbH in D-67547 Worms) were added at 60° C. to the slurry obtained. While maintaining the 60° C., stirring was continued for another 15 min. The resulting slurry was then spray-dried in a hot air countercurrent process (gas inlet temperature: 400±10° C., gas outlet temperature: 140±5° C.) to obtain a spray powder whose ignition loss (3 h at 600° C. under air) was 30% of its weight. The spray powder had a d$_{50}$ of 20.3 μm, a d$_{10}$ of 3.24 μm and a d$_{90}$ of 53.6 μm (measured at a dispersion pressure of 2 bar absolute).

An additional 1.0% by weight (based on the amount of spray powder) of Asbury 3160$_{[g1]}$ graphite from Asbury Graphite Mills Inc., New Jersey 08802, USA, was mixed into the spray powder.

The dry mixture resulting in this case was coarsened by means of a K200/100 compactor from Hosokawa Bepex GmbH (D-74211 Leingarten) under the conditions of gap width 2.8 mm, screen width 1.0 mm, undersize screen width 200 μm, target pressing force 35 kN and screw speed 65 to 70 rpm, by preliminary compaction to an essentially uniform particle size of from 200 μm to 1 mm.

The compactate was subsequently mixed with, based on its weight, a further 2% by weight of the same graphite and then compacted with the aid of a Kilian RX73 rotary press from Kilian, D-50735 Cologne, under an air atmosphere to give ringlike shaped multimetal oxide unsupported catalyst precursor bodies F$^{LII}$ with an uncurved (i.e. with a planar) end face. The basic apparatus construction was as in FIG. 6. The mold used (die, punch, etc.) and the materials for die table tongue, die table brow and die table chin corresponded to those from example II. This is also true of the other compaction conditions including the end distance E of 3 mm. The side crushing strength of the resulting ringlike shaped multimetal oxide precursor bodies was from 19 to 21 N. For their subsequent thermal treatment, in each case 1900 g of the ringlike shaped unsupported multimetal oxide catalyst precursor bodies were poured into a heatable forced-air chamber (capacity 0.12 m$^3$) (2 m$^3$ (STP) of air/min). Subsequently, the temperature in the bed was changed as follows:

increased from 25° C. to 160° C. at 1° C./min;
then held at 160° C. for 100 min;
then increased from 160° C. to 200° C. at 3° C./min;
then held at 200° C. for 100 min;
then increased from 200° C. to 230° C. at 2° C./min;
then held at 230° C. for 100 min;
then increased from 230° C. to 270° C. at 3° C./min;
then held at 270° C. for 100 min;
then increased to 380° C. at 1° C./min;
then held at 380° C. for 4.5 h;
then increased to 430° C. at 1° C./min;
then held at 430° C. for 4.5 h;
then increased to 500° C. at 1° C./min;
then held at 500° C. for 9 h;
then cooled to 25° C. within 4 h.

This afforded ringlike shaped multimetal oxide unsupported catalyst bodies from the ringlike shaped multimetal oxide unsupported catalyst precursor bodies. These are suitable, for example, as catalysts for the heterogeneously catalyzed partial gas phase oxidation of propylene to acrolein.

These were subjected to the undersize screening according to example 11. Based on the weight of all of the screening material introduced to the screening, the undersize fraction obtained was 0.6% by weight.

When the procedure was the same as described above, except that the compaction of the pulverulent aggregate was performed with a die whose die bore was an ideal circular cylinder (diameter=5 mm; the diameter of the upper and of the lower end face was 4.95 mm), the undersize fraction obtained in the screening was 3.2% by weight.

IV. Production of Ringlike Shaped Multimetal Oxide Unsupported Catalyst Precursor Bodies where the Active Multimetal Oxide had the Stoichiometry $Mo_{12}P_{1.5}V_{0.6}Cs_{1.0}Cu_{0.5}Sb_1S_{0.04}O_x$ 537.5 kg of ammonium heptamolybdate tetrahydrate $((NH_4)_6Mo_7O_{24}\cdot 4H_2O$ (81% by weight of $MoO_3$, 8% by weight of $NH_3$, $\leqq$50 ppm by weight of Na and $\leqq$100 ppm by weight of K)) were metered with stirring (70 revolutions per minute (rpm)) into 619 l of water heated to 45° C. in a water-heated jacketed vessel. This lowered the temperature of the solution to 37° C. In order to ensure reliable dissolution of the ammonium heptamolybdate, stirring was continued for another 15 minutes after the end of the metered addition, while retaining the temperature of 37° C. With further stirring at the same temperature, 17.82 kg of ammonium metavanadate ($NH_4VO_3$, 77% by weight of $V_2O_5$, 14.5% by weight of $NH_3$, $\leqq$150 ppm by Neight of Na and $\leqq$500 ppm by weight of K) were metered in within 3 minutes. Stirring was continued for 2 minutes. Then a colorless clear solution of 49.6 kg of cesium nitrate ($CsNO_3$ with 72% by weight of $CS_2O$ and $\leqq$50 ppm by weight of Na, $\leqq$100 ppm by weight of K, $\leqq$10 ppm by weight of Al and $\leqq$20 ppm by weight of Fe) in 106 l of water at 60° C., prepared in a separate dissolution vessel, was stirred in within one minute. In the course of this, the temperature of the resulting suspension rose to 39° C. After continuing to stir for one minute, 31.66 l of 75% by weight phosphoric acid (density at 25° C. and 1 atm: 1.57 g/ml, viscosity at 25° C. and 1 atm: 0.147 cm$^2$/S) were metered in within a further minute with continued stirring. Owing to the exothermic reaction, the temperature rose to 42° C. Stirring was again continued for 1 minute. Then 1.34 kg of ammonium sulfate ($(NH_4)_2SO_4$ (>99% by weight)) were stirred in within one minute and the mixture was stirred for a further 1 minute. With continued stirring at identical temperature, 37.04 kg of antimony trioxide ($Sb_2O_3$, particle diameter $d_{50}$=approx. 2 μm, crystal structure according to XRD: >75% senarmontite, <25% valentinite, purity: >99.3% by weight, $\leqq$0.3% by weight of $As_2O_3$, $\leqq$0.3% by weight of PbO and $\leqq$300 ppm by weight of FeO) were added within 3 minutes (commercially available as Triox White, Code No. 639000 from Antraco, D-10407 Berlin). The stirrer speed was then reduced from 70 to 50 rpm. Subsequently, the stirred suspension was heated to 95° C. in a linear manner within 30 minutes by means of steam in the jacket. At this temperature and 50 rpm, 51.64 kg of copper nitrate solution (aqueous $Cu(NO_3)_2$ solution with 15.6% by weight of Cu) were added within 4 minutes. After continuing to stir at 95° C. for 56 minutes$_{[g2]}$, the stirrer speed was reduced further from 50 to 35 rpm. Subsequently, the entire suspension was discharged within 4 minutes into a nitrogen-blanketed spray tower reservoir vessel heated to 85° C. and stirred at 35 rpm, and was flushed in with 20 l of water (25° C.). From this vessel, the suspension was spray-dried in a Niro FS-15 rotary disk spray tower in hot air concurrent (gas inlet temperature: 285±10° C., gas outlet temperature: 110±5° C., disk speed: 18 000 rpm, throughput: 270 kg/h), and the resulting spray powder had an ignition loss (1 h at 500° C. in air) of 17.2% by weight and a $d_{50}$ of 35.9 μm ($d_{10}$=14.3 μm, $d_{90}$=65.6 μm, measured at a dispersion pressure of 2 bar absolute).

The spray powder was mixed homogeneously with 1.5% by weight of Timrex 44 graphite from Timcal and compacted (K200/100 compactor with concave, fluted, smooth rollerers from Hosokawa Bepex GmbH, D-74211 Leingarten, gap width: 2.8 mm, screen width: 1.25 mm, undersize screen width: 400 μm, screw speed: 65 to 70 rpm). For the tableting, a further 1% by weight of the same graphite was mixed into the compactate.

Subsequently, the pulverulent aggregate obtained as described was compacted in accordance with the invention under an air atmosphere with the aid of a Korsch PH 865 rotary press single mold, 65 dies). The basic apparatus construction was as in FIG. 6. The diameter of the preliminary pressure rollerer was 100 mm and the diameter of the main pressure rollerer was 300 mm. The distance between two dies opposite one another on the die table was 780 mm.

The dies used were dies with a congruent double frustocone as shown schematically in FIGS. 3a, 3b. The length I of longitudinal section I was 2.2 mm. The length II (the length II*) of longitudinal section II (of longitudinal section II*) was 10 mm.

The outline of circular cylinder I and of circular cylinder II was 22 mm. The diameter DD of the top face of the frustocone KS was 7.1 mm. The diameter DG of the bottom face of the frustocone KS was 7.0 mm. The length of the outline of the circular cylinder Z (of the continuous circular cylindrical center pin) was 3.0·π mm. The planar upper end face of the center pin MF concluded flush with the planar upper die end face.

Only ringlike shaped precursor bodies $F^{LII}$ were manufactured, and the end distance E was always 7 mm. The upper end face of the lower punch and the lower end face of the upper punch were both of planar configuration. The bore axis B was at right angles to both end faces.

Both center bores, $MB^U$ and $MB^O$ (the latter was connected to two gas-permeable outlets (cf. FIG. 4d)) had, in the entrance region into the corresponding end face, a circular cylindrical geometry with an identical radius. The contact of their inner walls to the outer surface of the center pin MF was sliding on one another in the region of possible contact.

The individual die was manufactured from a material composite. This consisted, on its side in contact with the die bore, of the hard metal G10-Ni (wall thickness 2.5 to 2.6 mm) with $R_a$=0.1 μm, and, on its side facing away from the die bore, of DIN tool steel 1.2379 (wall thickness 9 mm) with $R_a$=0.8 μm. The upper punch and the lower punch were manufactured from DIN material 1.2601. The center pin MF, which was circular cylindrical over its entire length, was manufactured from DIN tool steel 1.2343 ($R_a$=0.4 μm). $R_a$ of the two end faces was likewise 0.4 μm.

The amount of pulverulent aggregate introduced into the fill chamber was 576 mg.

At the start of the process, the lower end face of the upper punch concluded flush with the upper end of longitudinal section II in the state of starting distance A. With increasing wear on the inner wall of the upper part of longitudinal section II of the die bore, the positions of both end facets within longitudinal section II in the state of starting distance A were shifted downward. The preliminary pressing force applied in each of the two punches was 0.3 kN; the main pressing force applied in each of the two punches was 3.5 kN.

The side crushing strengths of the resulting ringlike shaped multimetal oxide unsupported catalyst precursor bodies was in the range from 33 to 37 N. The rotation speed of the rotary press was from 20 to 25 rpm. With regard to the material of die table tongue, die table brow and die table chin, the statements made in the description apply.

Subsequently, 8 kg of the ringlike shaped multimetal oxide unsupported catalyst precursor bodies were distributed uniformly in a wire vessel of base area 33.0 cm x 49.5 cm, giving a bed height of 4 cm. The wire vessel was disposed in a chamber oven (from Elino Industrie-Ofenbau, Carl Hanf GmbH & Co, D-52355 Düren, model KA-040/006-08 EW.OH, dimensions: length=57 cm, width=57 cm, height=80 cm) such that the bed of the tablets could be flowed through uniformly. 2 $m^3$ (STP)/h of fresh air were supplied and the air circulation in the oven was adjusted such that the bed was flowed through at a speed of 0.9 m/s (determined by means of Aerometer, from Testo, model 445). The oven was then heated to 380° C. with the following temperature ramp: heat to 180° C. within 40 min, hold for 30 min, heat to 220° C. within 10 min, hold for 30 min, heat to 270° C. within 13 min, hold for 30 min, heat to 340° C. within 25 min and then to 380° C. within 40 min. This temperature was then held for 390 min. During this, the $NH_3$ content in the thermal treatment atmosphere sucked out was monitored continuously by FTIR spectroscopy ("Impact" spectrometer from Nicolet, stainless steel IR cell with $CaF_2$ window, path length 10 cm, heating to 120° C., determination of the concentration with reference to the intensity of the band at 3.333 $cm^{-1}$). The $NH_3$ content remained $\leq 2.4\%$ by volume over the entire thermal treatment. This maximum value was attained at 220° C.

The resulting ringlike shaped multimetal oxide unsupported catalyst bodies are suitable, for example, as catalysts for the heterogeneously catalyzed partial gas phase oxidation of methacrolein to methacrylic acid.

Thereafter, the ringlike shaped multimetal oxide unsupported catalyst bodies formed were subjected to undersize screening. The screens used were screens with elongated holes. Their straight edge length was 20 mm and the distance between the two edges was 6 mm. Based on the weight of all of the screening material introduced to the screening, the undersize fraction obtained was 14% by weight.

When the procedure was the same as described above, except that the compaction of the pulverulent aggregate was carried out with a die whose die bore was an ideal circular cylinder (diameter=7 mm; the diameter of the two end faces was 6.95 mm), the undersize fraction obtained in the screening was 21.7% by weight.

V. Production of Ringlike Shaped Multimetal Oxide Unsupported Catalyst Precursor Bodies where the Active Multimetal Oxide Comprises Vanadium, Phosphorus, Iron and Oxygen A nitrogen-inertized 8 $m^3$ steel/enamel stirred tank which was externally heatable by means of pressurized water and had baffles was initially charged with 4602 kg of isobutanol. After the three-level impeller stirrer had been started up, the isobutanol was heated to 90° C. under reflux. At this temperature, the addition of 690 kg of vanadium pentoxide was then commenced by means of a conveying screw. After about ⅔ of the desired amount of vanadium pentoxide had been added after approx. 20 minutes, the pumped introduction of 805 kg of polyphosphoric acid having a $P_2O_5$ content of 76% by weight (corresponds to 105% by weight of $H_3PO_4$) at a temperature of 50° C. was commenced with further addition of vanadium pentoxide. After the addition of the phosphoric acid had ended, the reaction mixture was heated under reflux to about 100 to 108° C. and left under these conditions for 14 hours. Thereafter, the hot suspension was cooled to 60° C. within 70-80 minutes and 22.7 kg of Fe(III) phosphate (29.9% by weight of Fe) were added. After heating to reflux again within 70 minutes, the suspension boiled under reflux for a further hour. Subsequently, the suspension was discharged into a pressure suction filter which had been inertized with nitrogen and heated beforehand, and filtered at a temperature of about 100° C. at a pressure above the suction filter of up to 0.35 MPa abs. The filtercake was blown dry by constantly introducing nitrogen at 100° C. with stirring with a height-adjustable stirrer disposed in the middle within about one hour. The blowing to dryness was followed by heating to approx. 155° C. and evacuation to a pressure of 15 kPa abs (150 mbar abs). The drying was carried out down to a residual isobutanol content of <2% by weight in the dried catalyst precursor composition.

The Fe/V ratio was 0.016.

Subsequently, the dried powder was treated in a rotary tube with a length of 6.5 m, an internal diameter of 0.9 m and internal spiral helices (for mixing purposes) under air for 2 hours. The speed of the rotary tube was 0.4 rpm. The powder was conveyed into the rotary tube in an amount of 60 kg/h. The air feed was 100 $m^3$/h. The temperatures, measured directly on the outside of the externally heated rotary tube, of the five heating zones of equal length were, in the direction from "outlet of the powder" to "inlet of the powder" into the rotary tube, 250° C., 300° C., 345° C., 345° C. and 345° C.

The precursor composition withdrawn from the rotary tube was mixed intimately and homogeneously with 1% by weight of Timrex T44 graphite from Timcal AG. The resulting mixture was then compacted and subsequently mixed with a further 2% by weight of the same graphite.

Subsequently, the pulverulent aggregate obtained as described was compacted in accordance with the invention with the aid of a Korsch PH 865 rotary press under a nitrogen atmosphere (single mold, 65 dies). The fundamental apparatus construction was as in FIG. 6. The diameter of the preliminary pressure rollerer was 100 mm and the diameter of the main pressure rollerer was 300 mm. The distance between two dies opposite one another on the die table was 780 mm.

The dies used were dies with a congruent double frustocone as shown schematically in FIGS. 3*a*, 3*b*. Length I of the longitudinal section I was 6.2 mm. The length II (the length II*) of longitudinal section II (of longitudinal section II*) was 8 mm.

The outline of circular cylinder I and of circular cylinder II was 17.3 mm. The diameter DD of the top face of the frustocone KS was 5.5 mm. The diameter DG of the bottom face of the frustocone KS was 5.6 mm. The length of the outline of the circular cylinder Z (of the continuous circular cylindrical center pin) was 3.0·π mm. The planar upper end face of the center pin MF concluded flush with the planar upper die end face.

Only ringlike shaped bodies $F^{LII}$ were manufactured, and the end distance E was always 3.2 mm. The upper end face of the lower punch and the lower end face of the upper punch were both of planar configuration. The bore axis B was at right angles to both end faces.

Both center bores, $MB^U$ and $MB^O$ (the latter was connected to two gas-permeable outlets (cf. FIG. 4*d*)), had, in the entrance region into the corresponding end face, a circular cylindrical geometry with identical radius. The contact of their inner walls to the outer surface of the center pin MF was sliding on one another in the region of possible contact.

The individual die was manufactured from a material composite. This consisted, on its side in contact with the die bore, of the hard metal G10-Ni (wall thickness 3.2-3.3 mm) with $R_a$=0.1 µm, and, on its side facing away from the die bore, of DIN tool steel 1.2379 (wall thickness 9.1 mm) with $R_a$=0.8 µm. The upper punch and the lower punch were manufactured from DIN material 1.2601. The center pin MF, which was circular cylindrical over its entire length, was manufactured from DIN tool steel 1.2343 ($R_a$=0.4 µm). $R_a$ of the two end faces was likewise 0.4 µm.

The amount of pulverulent aggregate introduced into the fill chamber was 90 mg.

At the start of the process, the lower end face of the upper punch concluded flush with the upper end of longitudinal section II in the state of starting distance A. With increasing wear on the inner wall of the upper part of longitudinal section II of the die bore, the positions of both end faces within longitudinal section II were shifted downward in the state of starting distance A. The preliminary pressing force applied to each of the two punches was 0.3 kN; the main pressing force applied to each of the two punches was 4.2 kN.

The side crushing strengths of the resulting ringlike shaped multimetal oxide unsupported catalyst precursor bodies were in the range from 9 to 11 N. The rotation speed of the rotary press was from 20 to 30 rpm. With regard to the material of die table tongue, die table brow and die table chin, the statements made in the description apply.

From the resulting ringlike shaped precursor multimetal oxide unsupported catalyst precursor bodies, thermal treatment as described in WO 03/78059, page 39 in example 9, generated the resulting ringlike multimetal oxide unsupported catalysts. These are suitable, for example, as catalysts for the heterogeneously catalyzed partial gas phase oxidation of n-butane to maleic anhydride.

Thereafter, the ringlike shaped multimetal oxide unsupported catalyst bodies formed were subject to undersize screening. The screens used were screens with elongated holes. Their straight edge length was 4 mm and the distance between the two edges was 4 mm. Based on the weight of all of the screening material introduced to the screening, the undersize fraction obtained was 0.3% by weight.

When the procedure was the same as described above, but the compaction of the pulverulent aggregate was performed by means of a die whose die bore was an ideal circular cylinder (diameter=5.5 mm; the diameter of the two end faces was 5.45 mm), the undersize fraction obtained in the screening was 1.2% by weight.

U.S. Provisional Patent Applications Ser. No. 61/077,601, filed Jul. 2, 2008, and No. 61/077638, likewise filed Jul. 2, 2008, are incorporated into the present patent application by literature reference. With regard to the abovementioned teachings, numerous changes and deviations from the present invention are possible. It can therefore be assumed that the invention, within the scope of the appended claims, can be performed differently from the way described specifically herein.

The invention claimed is:

1. A process for producing a ringlike oxidic shaped body comprising the mechanical compaction of a pulverulent aggregate which has been introduced into the fill chamber of a die and is composed of constituents which comprise at least one metal compound which can be converted to a metal oxide by thermal treatment at a temperature of $\geq 100°$ C., or at least one metal oxide, or at least one metal oxide and at least one such metal compound, to give a ringlike shaped precursor body, in which the fill chamber is disposed in a die bore conducted through the die material from the top downward with a vertical bore axis B and is delimited by the inner wall of the die bore, the upper end face of a lower punch introduced from below along the bore axis B into the die bore so as to be liftable and lowerable, on which the pulverulent aggregate introduced into the fill chamber rests, the lower end face, disposed along the bore axis B at an axial starting distance A above the upper end face of the lower punch, of an upper punch mounted so as to be liftable and lowerable along the bore axis B, whose lower end face is in contact with the pulverulent aggregate introduced into the fill chamber from above, and the outer face of a center pin MF conducted from the bottom upward in the die bore along the bore axis B from the geometric center of the upper end face of the lower punch, said center pin MF extending at least up to the geometric center of the lower end face of the upper punch, comprising reducing the axial starting distance A of the two end faces along the bore axis B to an axial end distance E predefined for the compaction by lowering the upper punch while maintaining the position of the lower punch or additionally lifting the lower punch, where the geometric shape of the outer face of the lower punch corresponds to that of the outer face of a circular cylinder I;

the geometric shape of the outer face of the upper punch corresponds to that of the outer face of a circular cylinder II;

in the geometric center of the upper end face of the lower punch, a center bore $MB^U$ conducted through the lower punch from the top downward is formed;

at the starting distance A of the two end faces, the center pin MF projects from below through the center bore $MB^U$ at least up to the geometric center of the lower end face of the upper punch;

the center pin MF, from the bottom upward, has the geometric shape of a circular cylinder Z with a circular cylindrical outer face MZ;

the length of the outline of the circular cylinder Z is less than the length of the outline of the circular cylinder I and less than the length of the outline of the circular cylinder II;

the position of the center pin MF and the position of the die including the die bore along the bore axis B are fixed relative to one another during the process;

in the geometric center of the lower end face of the upper punch, a center bore $MB^O$ which is conducted into the upper punch and is connected to at least one outlet from the upper punch is formed, said center bore $MB^O$ being capable of accommodating the center pin MF to the necessary degree in the event of reduction of the starting distance A to the end distance E, and the center pin MF being able to project into it even at the starting distance A;

the axes of symmetry of the die bore, of the circular cylinder I, of the circular cylinder II, of the center bore MB $MB^O$, of the center pin MF and of the center bore $MB^U$ are on a common straight line L running vertically through the die bore;

the die bore, along its bore axis, has a longitudinal section I over whose length I the geometric shape of the inner wall of the die bore corresponds to that of the outer face of a circular cylinder KZ, and which is adjoined at its upper end directly by a longitudinal section II of the die bore which is directed upward and has the length II;

the dimensions of the longitudinal section I of the die bore and of the circular cylinder I are such that the lower punch, during the process, is always conducted in each case sliding into the die bore at least for part of the length of the longitudinal section I with its outer face on the inner wall of the die bore; and the dimensions of the center bore $MB^U$ and of the circular cylinder Z are such that the lower punch, during the process, is always conducted sliding into the die bore at least in the region of the entrance of its center bore $MB^U$ into its upper end face with the inner wall of the center bore $MB^U$ on the circular cylindrical outer face MZ of the center pin MF; and on completion of compaction, the upper punch is lifted from the ringlike shaped precursor body formed and the ringlike shaped precursor body is removed from the die bore by lifting the lower punch, and a subsequent process for thermal treatment of the ringlike shaped precursor body at a temperature of $\geq 100°$ C., in which at least a portion of its constituents is decomposed and/or converted chemically to form at least one gaseous compound and the ringlike oxidic shaped body forms, wherein the geometric shape of the inner wall of the die bore, over the length II of the longitudinal section II, from the bottom upward, corresponds to that of the outer face of a frustocone KS which widens from the bottom upward, whose cross-sectional area, at its lower end, corresponds to the cross-sectional area of the circular cylinder KZ at its upper end, with the proviso that, on attainment of the end distance E, the lower end face of the upper punch is in the longitudinal section II and the upper end face of the lower punch is not below the longitudinal section I, such that the ringlike shaped precursor body formed by the mechanical compaction of the pulverulent aggregate between the two end faces is at least partly in the longitudinal section II on attainment of the end distance E.

2. The process according to claim 1, wherein, on attainment of the end distance E between the upper end face of the lower punch and the lower end face of the upper punch, at least 20% of the distance between the two end faces is within the longitudinal section II.

3. The process according to claim 1, wherein, on attainment of the end distance E between the upper end face of the lower punch and the lower end face of the upper punch, at least 60% of the distance between the two end faces is within the longitudinal section II.

4. The process according to claim 1, wherein, on attainment of the end distance E between the upper end face of the lower punch and the lower end face of the upper punch, at least 90% of the distance between the two end faces is within the longitudinal section II.

5. The process according to claim 1, wherein, on attainment of the end distance E between the upper end face of the lower punch and the lower end face of the upper punch, all of the ringlike shaped precursor body formed by the mechanical compaction of the pulverulent aggregate between the two end faces is within the longitudinal section II.

6. The process according to claim 1, wherein the outline of the circular cylinder II is longer than or is equal in length to the outline of the circular cylinder I.

7. The process according to claim 1, wherein the upper end face of the lower punch and the lower end face of the upper punch are in planes parallel to one another, to which the bore axis B is at right angles.

8. The process according to claim 1, wherein the end distance E is from 2 to 10 mm.

9. The process according to claim 1, wherein the end distance E is from 2 to 8 mm.

10. The process according to claim 1, wherein the end distance E is from 3 to 8 mm.

11. The process according to claim 1, wherein the end distance E is from 3 to 7 mm.

12. The process according to claim 1, wherein the quotient Q of the length of the outline of the circular cylinder Z as the numerator and the outline of the circular cylinder I as the denominator is from 0.3 to 0.7.

13. The process according to claim 1, wherein the quotient Q of the length of the outline of the circular cylinder Z as the numerator and the outline of the circular cylinder I as the denominator is from 0.4 to 0.6.

14. The process according to claim 1, wherein the difference formed by subtracting the radius of the outline of the circular cylinder Z from the radius of the outline of the circular cylinder I is from 1 to 3 mm.

15. The process according to claim 1, wherein the diameter of the outline of the circular cylinder I is from 2 to 10 mm.

16. The process according to claim 1, wherein the diameter of the outline of the circular cylinder I is from 2 to 8 mm.

17. The process according to claim 1, wherein the diameter of the outline of the circular cylinder I is from 4 to 8 mm.

18. The process according to claim 1, wherein the frustocone KS is such that the following relationship between the diameter DD of the top face, the diameter DG of the bottom face and the height H of the frustocone KS is satisfied:

$$0.003 \cdot H \leq DG - DD \leq 0.050 \cdot H.$$

19. The process according to claim 1, wherein the frustocone KS is such that the following relationship between the diameter DD of the top face, the diameter DG of the bottom face and the height H of the frustocone KS is satisfied:

$$0.005 \cdot H \leq DG - DD \leq 0.025 \cdot H.$$

20. The process according to claim 1, wherein the frustocone KS is such that the following relationship between the diameter DD of the top face, the diameter DG of the bottom face and the height H of the frustocone KS is satisfied:

$$0.007 \cdot H \leq DG - DD \leq 0.015 \cdot H.$$

21. The process according to claim 1, wherein both the upper end face of the lower punch and the lower end face of the upper punch have the geometric shape of a circular ring.

22. The process according to claim 1, wherein both the upper end face of the lower punch and the lower end face of the upper punch have the geometric shape of a circular ring curved inward into the interior of the punch.

23. The process according to claim 1, wherein the die bore has only the longitudinal sections I and II.

24. The process according to claim 1, wherein the die bore of the die is such that its longitudinal section I is not only adjoined at its upper end directly by a longitudinal section II directed upward, but also at its lower end directly by a longitudinal section II* of length II* directed downward, and the geometric shape of the inner wall of the die bore, over the length II* of the longitudinal section II*, corresponds to the outer face of a frustocone KS* whose cross-sectional area at its upper end corresponds to the cross-sectional area of the circular cylinder KZ at its lower end.

25. The process according to claim 24, wherein the die bore has only the longitudinal sections I, II and II*.

26. The process according to claim 24, wherein the geometric dimensions of longitudinal section II correspond to those of longitudinal section II*.

27. The process according to claim 1, wherein the following relationship between the height H of the frustocone KS and the end distance E is satisfied:

$$4 \cdot \text{end distance } E \geq H \geq 1 \cdot \text{end distance } E.$$

28. The process according to claim 1, wherein the following relationship between the height H of the frustocone KS and the end distance E is satisfied:

$$3 \cdot \text{end distance } E \geq H \geq 1 \cdot \text{end distance } E.$$

29. The process according to claim 1, wherein the following relationship between the height H of the frustocone KS and the end distance E is satisfied:

$$3 \cdot \text{end distance } E \geq H \geq 1.5 \cdot \text{end distance } E.$$

30. The process according to claim 1, wherein the length of longitudinal section I is greater than the length II of longitudinal section II.

31. The process according to claim 1, wherein the length of longitudinal section I is less than the length II of longitudinal section II.

32. The process according to claim 1, wherein the length of longitudinal section I is not more than three times and not less than 0.1 times the length of longitudinal section II.

33. The process according to claim 1, wherein at least the entrance into the center bore $MB^O$ is configured in circular cylindrical form such that the outer face of the circular cylinder Z, when it is accommodated into the center bore $MB^O$, slides along its inner wall at least in the entrance region thereof.

34. The process according to claim 1, wherein the center pin MF narrows conically in the upward direction within the longitudinal section II.

35. The process according to claim 1, wherein the upper end of longitudinal section II of the die bore, the upper end face of the center pin MF and the upper end face of the die conclude flush with one another.

36. The process according to claim 1, wherein the process according to the invention is performed automatically with the aid of a rotary press.

37. The process according to claim 1, wherein the mechanical compaction consists of a preliminary compaction and of a main compaction following thereafter, the axial starting distance A, in the course of the preliminary compaction, first being reduced to a preliminary end distance $E^v$, and the preliminary end distance $E^v$ being reduced to the end distance E in the course of the main compaction.

38. The process according to claim 1, wherein the pulverulent aggregate comprises at least one metal oxide, metal hydroxide, metal carbonate, metal hydrogencarbonate, metal hydrogenphosphate and/or metal nitrate.

39. The process according to claim 1, wherein the pulverulent aggregate comprises at least one metal nitrate from the group consisting of cobalt nitrate, iron nitrate, bismuth nitrate, nickel nitrate, cesium nitrate, copper nitrate, calcium nitrate and magnesium nitrate.

40. The process according to claim 1, wherein the die is manufactured from a material composite which consists of a hard metal on its side in contact with the die bore and of a tool steel on its side facing away from the die bore, said tool steel having the following element composition:

1.50 to 1.80% by wt. of C,
0.10 to 0.40% by wt. of Si,
0.10 to 0.50% by wt. of Mn,
$\geq 0$ to 0.05% by wt. of P,
$\geq 0$ to 0.05% by wt. of S,
10 to 13% by wt. of Cr,
0.50 to 0.80% by wt. of Mo,
0.10 to 1.10% by wt. of V,
$\geq 0$ to 0.60% by wt. of W, and
$\geq 0$ to 0.10% by wt. of one or more rare earth metals, and apart from these Fe and impurities resulting from the production.

41. The process according to claim 40, wherein the hard metal consists of tungsten carbide to an extent of $\geq 90\%$ by weight and of nickel or of nickel and chromium to an extent of at least 5% by weight.

42. The process according to claim 40, wherein the hard metal consists of 90 to 95% by wt. of WC
$\geq 0$ to 1% by wt. of TiC and/or TaNbC, and
5 to 10% by wt. of Ni or Ni and Cr.

43. The process according to claim 1, wherein the pulverulent aggregate comprises nitric acid, an ammonium salt and/or a nitrate salt.

44. The process according to claim 1, wherein the mean roughness $R_a$ of the inner wall of the die bore is $\leq 0.2$ µm.

45. The process according to claim 1, wherein the mean roughness $R_a$ of the inner wall of the die bore is $\leq 0.1$ µm.

46. The process according to claim 1, wherein, at the end distance E, the two punches exert a pressure which is in the range from 50 to 5000 kg/cm$^2$.

47. The process according to claim 1, wherein, at the end distance E, the two punches exert a pressure which is in the range from 500 to 2500 kg/cm$^2$.

48. The process according to claim 1, wherein the process for thermal treatment of the ringlike shaped precursor bodies produced is effected at a temperature of $\geq 200°$ C.

49. The process according to claim 1, wherein the process for thermal treatment of the ringlike shaped precursor bodies produced is effected at a temperature of $\geq 300°$ C.

50. The process according to claim 1, wherein the thermal treatment of the ringlike shaped precursor bodies is accompanied by a weight loss of from 0.5 to 40% by weight based on its starting weight.

51. The process according to claim 1, wherein the at least one gaseous compound which forms in the course of thermal treatment is ammonia, $H_2O$, CO, $CO_2$ and/or a nitrogen oxide.

52. The process according to claim 1, wherein the pulverulent aggregate comprises at least one added substance from the group consisting of $NH_4OH$, $(NH_4)_2CO_3$, $NH_4HCO_3$, $NH_4NO_3$, urea, $NH_4CHO_2$, $NH_4CH_3CO_2$, $NH_4HSO_4$, $(NH_4)_2SO_4$, ammonium oxalate and the hydrates of the aforementioned ammonium salts.

53. The process according to claim 1, wherein the pulverulent aggregate comprises added graphite, starch, ground nutshell, fine polymer granule, cellulose, stearic acid, malonic acid, salt of stearic acid and/or salt of malonic acid.

54. The process according to claim 1, wherein the subsequent process for thermal treatment of the ringlike shaped precursor bodies produced forms a multimetal oxide which comprises the elements Mo and Fe, or the elements Mo, Fe and Bi, or the elements Mo and V, or the elements Mo, V and P, or the elements V and P.

55. The process according to claim 1, wherein the subsequent process for thermal treatment of the ringlike shaped precursor bodies produced forms a multimetal oxide in which the element Mo, or the element V, or the element P is that element other than oxygen which, calculated in molar terms, is the numerically most common.

56. The process according to claim 1, wherein the subsequent process for thermal treatment of the ringlike shaped precursor bodies produced forms a multimetal oxide of the general formula XII $$Mo_{12}Bi_aFe_bX^1_cX^2_dX^3_eX^4_fO_n \qquad (XII)$$

where
$X^1$=nickel and/or cobalt,
$X^2$=thallium, samarium, an alkali metal and/or an alkaline earth metal,
$X^3$=zinc, phosphorus, arsenic, boron, antimony, tin, cerium, lead, vanadium, chromium, niobium and/or tungsten,
$X^4$=silicon, aluminum, titanium and/or zirconium,
a=0.2 to 5,
b=0.01 to 5,
c=0 to 10,
d=0 to 2,
e=0 to 8,
f=0 to 10, and
n=a number which is determined by the valency and frequency of the elements in XII other than oxygen.

57. The process according to claim 1, wherein the subsequent process for thermal treatment of the ringlike shaped precursor bodies produced forms a multimetal oxide of the general formula XIII $$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \qquad (XIII)$$

where
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum or tungsten, or molybdenum and tungsten,
a'=0.01 to 8,
b'=0.1 to 30,
c'=0 to 4,
d'=0 to 20,
e'>0 to 20,
f'=0 to 6,
g'=0 to 15,
h'=8 to 16,
x', y'=numbers which are determined by the valency and frequency of the elements in XIII other than oxygen, and
p, q=numbers whose p/q ratio is from 0.1 to 10.

58. The process according to claim 1, wherein the subsequent process for thermal treatment of the ringlike shaped precursor bodies produced forms a multimetal oxide of the general formula XIV $$[Bi_{a''}Z^2_{b''}O_{x''}]_{p''}[Z^8_{12}Z^3_{c''}Z^4_{d''}Fe_{e''}Z^5_{f''}Z^6_{g''}Z^7_{h''}O_{y''}]_{q''} \qquad (XIV)$$

where
$Z^2$=molybdenum or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium, vanadium, chromium and/or Bi,
$Z^6$=silicon, aluminum, titanium and/or zirconium,
$Z^7$=copper, silver and/or gold,
$Z^8$=molybdenum or tungsten, or molybdenum and tungsten,
a''=0.1 to 1,
b''=0.2 to 2,
c''=3 to 10,
d''=0.02 to 2,
e''=0.01 to 5,
f''=0 to 5,
g''=0 to 10,
h''=0 to 1,
x'', y''=numbers which are determined by the valency and frequency of the elements in XIV other than oxygen, and
p'', q''=numbers whose p''/q'' ratio is from 0.1 to 5.

59. The process according to claim 1, wherein the subsequent process for thermal treatment of the ringlike shaped precursor bodies produced forms a multimetal oxide of the general formula XV $$Mo_{12}P_aV_bX^1_cX^2_dX^3_eSb_fRe_gS_hO_n \qquad (XV)$$

where
$X^1$=potassium, rubidium and/or cesium,
$X^2$=copper and/or silver,
$X^3$=cerium, boron, zirconium, manganese and/or bismuth,
a=0.5 to 3,
b=0.01 to 3,
c=0.2 to 3,
d=0.01 to 2,
e=0 to 2,
f=0 to 2,
g=0 to 1,
h=0 to 0.5, and
n=a number which is determined by the valency and frequency of the elements in XV other than oxygen.

60. The process according to claim 1, wherein the subsequent process for thermal treatment of the ringlike shaped precursor bodies produced forms a multimetal oxide of the general formula XVI $$V_1P_bFe_cX^1_dX^2_eO_n \qquad (XVI)$$

where
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b=0.9 to 1.5,
c=0 to 0.1,
d=0 to 0.1,
e=0 to 0.1, and
n=a number which is determined by the valency and frequency of the elements in XVI other than oxygen.

61. The process according to claim 1, wherein the subsequent process for thermal treatment of the ringlike shaped precursor bodies produced forms an oxide which is solid under standard conditions and in which no transition metal of transition group 5 to 11 nor phosphorus is that element other than oxygen which, calculated in molar terms, is the numerically most common.

62. The process according to claim 1, wherein the pulverulent aggregate comprises at least one metal oxide from the group consisting of aluminum oxide, tungsten oxide, antimony oxide, zirconium oxide, bismuth oxide, molybdenum oxide, silicon oxide, magnesium oxide and mixed oxides which comprise at least two of the metal elements present in the aforementioned metal oxides.

63. The process according to claim 1, wherein, already at the starting distance A, both the upper end face of the lower punch and the lower end face of the upper punch are in the longitudinal section II of the die bore.

64. A process for producing a ringlike oxidic shaped body comprising the mechanical compaction of a pulverulent aggregate which has been introduced into the fill the geometric shape of the outer face of the upper punch corresponds to that of the outer face of a circular cylinder II;

in the geometric center of the upper end face of the lower punch, a center bore $MB^U$ conducted through the lower punch from the top downward is formed;

at the starting distance A of the two end faces, the center pin MF projects from below through the center bore $MB^U$ at least up to the geometric center of the lower end face of the upper punch;

the center pin MF, from the bottom upward, has the geometric shape of a circular cylinder Z with a circular cylindrical outer face MZ;

the length of the outline of the circular cylinder Z is less than the length of the outline of the circular cylinder I and less than the length of the outline of the circular cylinder II;

the position of the center pin MF and the position of the die including the die bore along the bore axis B are fixed relative to one another during the process;

in the geometric center of the lower end face of the upper punch, a center bore $MB^O$ which is conducted into the upper punch and is connected to at least one outlet from the upper punch is formed, said center bore $MB^O$ being capable of accommodating the center pin MF to the necessary degree in the event of reduction of the starting distance A to the end distance E, and the center pin MF being able to project into it even at the starting distance A;

the axes of symmetry of the die bore, of the circular cylinder I, of the circular cylinder II, of the center bore $MB^O$, of the center pin MF and of the center bore $MB^U$ are on a common straight line L running vertically through the die bore;

the die bore, along its bore axis, has a longitudinal section I over whose length I the geometric shape of the inner wall of the die bore corresponds to that of the outer face of a circular cylinder KZ, and which is adjoined at its upper end directly by a longitudinal section II of the die bore which is directed upward and has the length II;

the dimensions of the longitudinal section I of the die bore and of the circular cylinder I are such that the lower punch, during the process, is always conducted in each case sliding into the die bore at least for part of the length of the longitudinal section I with its outer face on the inner wall of the die bore; and the dimensions of the center bore $MB^U$ and of the circular cylinder Z are such that the lower punch, during the process, is always conducted sliding into the die bore at least in the region of the entrance of its center bore $MB^U$ into its upper end face with the inner wall of the center bore $MB^U$ on the circular cylindrical outer face MZ of the center pin MF; and on completion of compaction, the upper punch is lifted from the ringlike shaped precursor body formed and the ringlike shaped precursor body is removed from the die bore by lifting the lower punch, and a subsequent process for thermal treatment of the ringlike shaped precursor body at a temperature of $\geq 100°$ C., in which at least a portion of its constituents is decomposed and/or converted chemically to form at least one gaseous compound and the ringlike oxidic shaped body forms, wherein the geometric shape of the inner wall of the die bore, over the length II of the longitudinal section II, from the bottom upward, corresponds to that of the outer face of a frustocone KS which widens from the bottom upward, whose cross-sectional area, at its lower end, corresponds to the cross-sectional area of the circular cylinder KZ at its upper end, with the proviso that, on attainment of the end distance E, the lower end face of the upper punch is in the longitudinal section II and the upper end face of the lower punch is not below the longitudinal section I, such that the ringlike shaped precursor body formed by the mechanical compaction of the pulverulent aggregate between the two end faces is at least partly in the longitudinal section II on attainment of the end distance E, wherein, on attainment of the end distance E between the upper end face of the lower punch and the lower end face of the upper punch, at least 90% of the distance between the two end faces is within the longitudinal section II, wherein the outline of the circular cylinder II is longer than or is equal in length to the outline of the circular cylinder I, wherein the end distance E is from 2 to 10 mm, wherein the quotient Q of the length of the outline of the circular cylinder Z as the numerator and the outline of the circular cylinder I as the denominator is from 0.3 to 0.7, wherein the difference formed by subtracting the radius of the outline of the circular cylinder Z from the radius of the outline of the circular cylinder I is from 1 to 3 mm, wherein the frustocone KS is such that the following relationship between the diameter DD of the top face, the diameter DG of the bottom face and the height H of the frustocone KS is satisfied:

$$0.003 \cdot H \leq DG - DD \leq 0.050 \cdot H,$$

and wherein the following relationship between the height H of the frustocone KS and the end distance E is satisfied:

$$4 \cdot \text{end distance } E \geq H \geq 1 \cdot \text{end distance } E.$$

65. The process according to claim 64, wherein the pulverulent aggregate comprises at least one metal oxide, metal hydroxide, metal carbonate, metal hydrogencarbonate, metal hydrogenphosphate and/or metal nitrate.

66. The process according to claim 64, wherein the pulverulent aggregate comprises at least one metal nitrate from the group consisting of cobalt nitrate, iron nitrate, bismuth nitrate, nickel nitrate, cesium nitrate, copper nitrate, calcium nitrate and magnesium nitrate.

67. The process according to claim 64, wherein the die is manufactured from a material composite which consists of a hard metal on its side in contact with the die bore and of a tool steel on its side facing away from the die bore, said tool steel having the following element composition:

1.50 to 1.80% by wt. of C,
0.10 to 0.40% by wt. of Si,
0.10 to 0.50% by wt. of Mn,
$\geq 0$ to 0.05% by wt. of P,
$\geq 0$ to 0.05% by wt. of S,
10 to 13% by wt. of Cr,
0.50 to 0.80% by wt. of Mo,
0.10 to 1.10% by wt. of V,
$\geq 0$ to 0.60% by wt. of W, and
$\geq 0$ to 0.10% by wt. of one or more rare earth metals, and apart from these Fe and impurities resulting from the production.

* * * * *